(12) United States Patent
Andersson et al.

(10) Patent No.: US 6,528,268 B1
(45) Date of Patent: Mar. 4, 2003

(54) REAGENTS AND METHODS FOR DETECTION OF HEART FAILURE

(75) Inventors: Maria Kristina Andersson, Uppsala (SE); Lars Gunnar Ture Berglund, Uppsala (SE); Rikard Henry Reneland, Uppsala (SE); Gail Isabel Reid Adam, Knivsta (SE)

(73) Assignee: Sequenom-Gemini Limted, Stockport (GB)

( * ) Notice: Subject to any disclaimer, the term of this patent is extended or adjusted under 35 U.S.C. 154(b) by 0 days.

(21) Appl. No.: 09/922,445

(22) Filed: Aug. 3, 2001

(51) Int. Cl.$^7$ .................. C12Q 1/68; C07H 21/04
(52) U.S. Cl. .................. 435/6; 536/23.1; 536/23.5; 536/24.31; 536/24.33
(58) Field of Search ............... 435/6; 536/23.1, 536/23.5, 24.31, 24.33

(56) References Cited

U.S. PATENT DOCUMENTS

2001/0051712 A1   12/2001   Drysdale et al. ........... 536/23.5

FOREIGN PATENT DOCUMENTS

| EP | 1033401 | 9/2000 |
|----|---------|--------|
| WO | WO 99/58675 | 11/1999 |
| WO | WO 00/56766 | 9/2000 |
| WO | WO 00/76530 | 12/2000 |
| WO | WO 01/66753 | 9/2001 |
| WO | WO 01/74860 | 10/2001 |

OTHER PUBLICATIONS

GenBank Accession No. AC004923, Dec. 21, 1999.
GenBank Accession No. AJ271326, Jan. 4, 2001.
GenBank Accession No. AA632247, Oct. 28, 1997.
GenBank Accession No. AJ272060, Feb. 11, 2000.
GenBank Accession No. AJ272061, Feb. 11, 2000.
GenBank Accession No. AC034259, May 4, 2000.
GenBank Accession No. AC012661, Mar. 14, 2000.
GenBank Accession No. AC067827, Jun. 6, 2000.
GenBank Accession No. AC073648, Nov. 7, 2001.
GenBank Accession No. AC011744, Jan. 9, 2002.
GenBank Accession No. AY007125, Aug. 31, 2000.
GenBank Accession No. AAD15416, Dec. 21, 1999.
Kashuba et al., Gene (2002) 283(1–2):209–217.

*Primary Examiner*—Kenneth R. Horlick
*Assistant Examiner*—Alexander H. Spiegler
(74) *Attorney, Agent, or Firm*—Morrison & Foerster LLP

(57) ABSTRACT

The invention provides novel reagents, kits, and methods for diagnosis of predisposition to left ventricular heart failure, based on analysis of polymorphic variants of the genomic nucleic acid set forth in SEQ ID NO:1

2 Claims, 14 Drawing Sheets

| | |
|---|---|
| gatccacctgatctgtatgactcccgtactcaaccagcctatgtttcctaccagcgaatt | 60 |
| ttttttttttttttttttttttctttttttgagacaatctggctctgtggctcaggctg | 120 |
| gaatgcagtggtgcgatctcggctcactgcagcctcgacctcccaggctcgggtgatcct | 180 |
| cacttctcagcctcccgagcagctggaaccacagtcgcctgccaccaccaggctcggcta | 240 |
| atttttgtattttttgtagagacggggtctcgccatgttgcccaggctggtctggaactc | 300 |
| ctggactcaggcgatcctcctgcctcggcctgccaaagtgctgggattacaggcgtgagc | 360 |
| caccacgccgggcctttccccgggaatgctgtggtagagggacccgcagaggccccgagg | 420 |
| ctgcctgcatgtgtgtgttgggaggatctgcgctgagggtaggtaggagttgggcaggcc | 480 |
| aggacaggaaggaggcagagggcatgtcccatgcccgtgcagagggaggacacgcatggt | 540 |
| agaccaggacgaggacaagggcaggctcagtgtgtgcaaaggggacagtggtttgggatt | 600 |
| tgcatgcagatgcccgagcctccaaaggacctgtgggccacagggagaccctgggggagt | 660 |
| tcaagctgaggagtggagagggctttgggctggtcagcaggtgctcagaggagagggct | 720 |
| ggccctagagagaagggaggtcttgggatggtggcccacacctgaccctggcccttcatc | 780 |
| aggtgattcctgcgtggatgcctgcggggattcctgcgtggattggggaagtcctgcagc | 840 |
| attacagaattgttacccaacgccagggccttggtccagagtcctgttgctagatgcaca | 900 |
| gaaagcaaatcactgagatgtaagtattgccagggaagaaggctttattcaggtgacatc | 960 |
| agccagagagacaggagacgaaactcaggtccacccctgtccctcttcccgactaaagtt | 1020 |
| gtaggttgatatagtctaaaaagaaagcaggagccaaggaagaggaggtggcccgcaggc | 1080 |
| cgcaggagcagcctctcattgtccaaatgtaggtttctcaagcatccggcttgttaggaa | 1140 |
| attgggccagtttcagaatcatcagcttgttcaaaagtgggacttgggaggtgagaaggg | 1200 |
| ttgtcaggcaggaaaccctgcattctgctttggctgagtggatggggcccaggaggatga | 1260 |
| gcagcatggggaagagtatgactcgtagtgggcaccatgaggataaagagttacaagctc | 1320 |
| ctctggcatgggctggagggaagggagaccctatcgcataaccacagcccacctgcctg | 1380 |
| gagagaagaggggaggcggccccgctccgtgccaccccactgagaaagataggacacctgg | 1440 |
| agctccagctcagcaatccctcaatccctcaatccttcatttcatccttgcaacagtccc | 1500 |
| aggaggtttttttttttttttttttaaggcagagcctccttctgtcacccaggccggag | 1560 |
| ttcagtgacgcaatctcagctcacggcaacctccacctcccggggttcaagcgattctcct | 1620 |
| gccttagcctcctgagtagctgggattacaggcatgcgccaccacgccaggctaattttt | 1680 |
| gtattttagtagagacggggtttcgccatgttagccaggctgatcttgaactcctgatt | 1740 |
| tcaggtgatccgcctgcctcggcctcccaaagtgctgggattacaggtgtgagccgcctc | 1800 |
| acccagccaggaggtatcaatggttaattctctccactgaacaaatggaaaaactgagac | 1860 |
| tcagagagggcaggaatggccttggatgcagtgattccatggtgtggcctgagtcagatg | 1920 |
| ccagggcccctcggacgcccgctccacaggagagggtgactcagaggtgccgtgtctgt | 1980 |
| cctcttctcctgaatatgggtggttggtgcggggcaggggtgagtcactgcactgttt | 2040 |
| cccatgcctcccacctcggctctcatggttgggagcggctgagggaggaggctgaggcag | 2100 |
| ggagagggaagacccaggagggaggaggcaggcgctgctttgaggggtgccctggagcct | 2160 |
| tggcaatccttttcctcctcgggcccgggagcccaggccccgtctccaccagccgcaggc | 2220 |
| gacagctgtcatggtggtctacagcctgggcctggggaagggctcagagcagtgtgcagc | 2280 |
| tgcagccttggcctccatgccaccagcagcatcctcaggcggcgcggcgattgcggcgg | 2340 |
| gtagcggagggcgttgagcttctccatccccgggctgcgcaggaggcaggcgcgatggtg | 2400 |
| ggagaaggtgtcgaaggagaacttgccatggtaccggcccatcccactggcacctgtaca | 2460 |
| gtggcacagaacacaggtggtcaggcgctgggggtctcctagtcacagacagtggggcct | 2520 |
| aggcgggctacttctcccctctgagcctcagtttccccatctgtccagtgggctgatcat | 2580 |
| gaggcactgtgtgtaaagggcttggccccgagcttggcaccagctcagtaagccctgggg | 2640 |
| atgccagatgccagggcaagataggcgggtggtggtcaagggcatggattccagagtcag | 2700 |
| actgccgggggttaaactctggccctgctgcaaacaatccatgtcaccttggactgtgcc | 2760 |
| tcagtctcctctgtcgtggggtgacaagggtacctccctcctaaggttgtggtggggatt | 2820 |
| gagggatgttgagacccctggacccagtaggtgctatgtgcagtgaactctcctcagcg | 2880 |
| tctaggttgggaggcagacgaggcccaggccagggcgttcagagcacagcctgggtgga | 2940 |
| gtggggttggctgggggcttcctgcagtgagtgagctccaaggatatgcagttaataag | 3000 |
| acgaagagagtgggtgggggcaagagggacccaggcttggggagccttagaggtgggtgc | 3060 |
| catgcggtgtgttagggacctggcagagctcaggctgtgggagcagcaggtggggaagc | 3120 |
| cggggtggggccacggccaccaagaagggtcagctcgggggcctgggagctggggaggc | 3180 |
| tttcttgagggagcagcagggtcagatgtgcccacagacagccccgactctcctccaggg | 3240 |
| cagggaggcgggttgaggaggctggggctggggctggggaggcagctaggtggggtcggg | 3300 |

FIGURE 1A

```
ggcagccgcccaaactcgagccgagccaggacagcagcacaggcactgttgtgccctgg    3360
ctgccctccaggaagggcatggacccacctgaggcagcttgcctggccctgccatcgttc    3420
actgtggtgctgagtgtggacaggtggcgggactgcctgtcacctgctcggggcctactg    3480
ttctctgaggaggaagtgggctcagaaaggggagatgtcacctgggccacagggccttca    3540
gcgtgttgctaggaccatctctgaggcttcctgactcagaggccaggactctgcagtggc    3600
atcggggctgctctgggggtggaggattggcactcatccgggcctctcagggtggggag    3660
gtgttgtactgagagctggagggggatggggttagaggagcagctgccctggagtaaag    3720
gacaccggcggcattgctgctgaggggcagacaccaggtcatgctgttggggagaagagc    3780
aaatagcatcgcagtgggcagtgtgatcatagttgtgtggtattttttaaaaattcactaa    3840
attgtgtgtctgtgcagagatggtctagaaggttccaccacagacttttttttgagatgg    3900
ggtcttactgtgttgcccagattggactcagaccctctggggtggggagcaggatgcggg    3960
ttctggggtgaggcctccttgcctgtccctctacattgaggtggggctggggtgctttgg    4020
cagaaatgtatgcaggtaacactattgcaatttgaccaaatggtaacagaagggcaggt    4080
agcaggcacctacccactcctccaaaaggcaggctggccagggtcatgtgcatgaagccg    4140
tcgttcccacagaagcccccgctgctggtctgggtcagcacccgcttgaccacctgggag    4200
agaacaggatgtgcgtgaggctgccttgagccccatcaggatcctcaggacccagagcct    4260
gttccatgctggactctgtgacactgatcttgcctcagaaagggtctgaggccaccatgt    4320
cagctgaagggcctgtgatggtacaggtggggcaggggttgtgtagcagctcctcatga    4380
agcttccaacttgggacatgtttcctggacatctgctcatgtgtggtccatgctgatggc    4440
acagactcttagggctgggggtaggggcaggaaacctagtgttgcttggggacatggagg    4500
gtgtagtggcagcagggcagtactggacagtagggaggcatcccaggagagggtgtcat    4560
gtgcctgctgagtggagggactggggagggacagaagttgttcaggcaagagggcactgc    4620
agacagagtggaggctgaagagctgtgtggtgtgaacacagggacatgaaaacataatga    4680
tgtggtcagatttgcactttagaaacagaagcttggcccttgcttgaaggtccttgagaa    4740
ggaccttcttcctcaatctgtagacttatttgaagactgaaaggaaaaaaagattggtag    4800
acactaaatagttgctgcacaaaaacttcagtatatttagttgcaatcaccgtgaacctc    4860
tgatcacagctgggtcagggcttgtctgatgtggggaaagcggactgcccccagtggatt    4920
cagacgtcacttcatggcatgagaccagcattacccacaatggcagtggcagcagatgga    4980
ggagatggagcagaaggcagcagagggcgtcccaggtagtacgggcaagccaccttgtgc    5040
atgacttgtgtcttaggtgtgactgtgtgtcctgggatcagttctgggtggtcagaaaag    5100
tttgaagccagatgactccactgtcaaaaaacctctgtagagttttctaaaggtgaaagt    5160
atccagatgaagcagggctccttgaaggaatggctgcttctggagttggagcaggggaga    5220
tacaagatgagcctggagctgcttgtagcaccagaggggaaggaggtggtcacaacccaa    5280
gaggctgggacatcttacatgggcttctgagcccgagcctcagacaaaccacacgacctt    5340
ggattacagcccctggagtcaaataaatatacctgagtccgtagtgacctaaataaacaa    5400
ttcaagagatgaatctttcttacagaattccaggaaatagatgtagatactgctgttagc    5460
caagaatacggtatccagctaagactatgcttcgtagatgaagaaataaagcctttccca    5520
gacaagcaaaggctgggggaatttatcactactagatcagtcctgcaagaaatgctcaaa    5580
ggagtcttaacataaaaacaagttggtatttgccataatacacacaaaagtacaaaactc    5640
acaggccctataaaacaatcatacaaaggaggaagagaaaggtatcaaatggcaatacaa    5700
caaaattccaccaaaccacaaatggaataagaaaagaatgtataaaataactagataata    5760
actaacaatatgatagagcagcatacagcttaattacctccacctggtgagggtgggta    5820
ggcttagagacttgcttccaaataataaagaaacaaacaatagtagcttcccagggaaac    5880
cctggcagataccgtcctgacccggtagtgaaggttccactcactagccacgtgtgcatc    5940
tcaggtgccccagatgtggtgtgagaggcaggctcacctctgtgggattctctcctaaaa    6000
ccagtaacctttctttaatcatgagaaatacaccagatgacctgaggctggggatgttct    6060
acaggagacctgtccagcactccttaagctgagagggttattaatgcaaggtgggaccct    6120
ggcttggatcctggggccgaaagaggatgtcagtggaaaaacagcaaatccaaataaag    6180
tctagagtgtagttaatagtaaagcactgctgtcacttttttttttttttatgggtcag    6240
gagatccttccacctcagcctcccgagcagctggcattacaggtgtgcgccactatgcgc    6300
aactaatcttaaaaaatgtttcatagagacggggttttgctatattgccagcgctggtc    6360
tcaaactcatgagctcaagcaatcctcccaccttggcctcccaaagtgctgagattacag    6420
gtgtgagccaccgcgcccagccctgccatcacttttttagttttgacccatctaagcacc    6480
attaaatgggggaaattaggtgtggggtacatgggaactctctgtaccattttggcaact    6540
tttctgtaaatctaaaagtatttcccaatacaaagtttatttaaaaaaagttcaagtggc    6600
```

FIGURE 1B

```
cgggcacggtggctcatccctgtaatcccagcactttgggaggccgaggcaggtggatca       6660
cctgaggtcagcagttcaagactagcctgaccaatgtggcaaaacccatctctactaaa       6720
aatacaaagaattagccgggcatagtggcacacgcctgtaatcccagctacacaggagt       6780
tgaggcaggagaatcgcttgaacccgggaggcagaggttgcagtgagccaagactgtgct      6840
actgcactccagcctgggtgacagagtgagactctgtctcaaaaaaaaaaaaaaaaagt      6900
tcaagtggagggaatcgaggaactggctgagggccggggaaggggcggggtgggtaggg      6960
actgctggtacctcttggtgttttttaatctgaggactctggccttgggcctcccaggct     7020
gcctctgcagcttaagcaggggtaggggatcagggctcattcttggacctgcacctttgg     7080
gtcatccccgacacgttgcctgtgccttcagagccaggcttgaggggtcatgtggccacc     7140
aggccccgatgtgtaagaaggacaaaggcagggctgacctagaggaaacactggaccct     7200
agagaaggcccatacccaggaagctgcccactgaaggcctaggagagtggggcccagac     7260
tggggacagggttggggtgggtgaggctcagctgcttccaggagagtgggcagagacaga     7320
gccaagaggtccaccatcccaaagtcctgaagccactggattttggtgccccccctgctg    7380
ccaccacttgtgctgcccactgcgggctcctgaccctgcccagcccggccgcaccccac    7440
ctggctgctgttggagaaggcgtacagggccaggggcttctcccgccggttgatgaactc   7500
gatggcctcgtccaagctctgcacgttcacgatgggcaggatgggcccgaagatctcctc   7560
ctgcatcacaggctccatctcctgcacatccaccagcaccgtggggctgcaggcaccag   7620
agacagctcagccctggggccacagtcaggaccgcccccagggtgggggtagaggtgggg   7680
acagggccacaggccagggctctaggccaggatcccaaggtctgacttcccaaggcttca   7740
ggctttggagtgtttagggaagaaagtctccccacagcccccagaagggactctagagc   7800
ttccccagcctgctcagggcctgtgggacacagagaatcccccgaccttggtctcacagt   7860
cagggggtgatgggatcttagaacccttggagttcatgaggcaacagcgtcccagaatgtt   7920
ggcgccgcagtgtcccatgagctgctgagccgtacggcccaggagactgggggctcagga   7980
cgggactctcggagtttagaacctggggattgtgggctcggagaatctgaggttacagcc   8040
tttcaggatagccagtggtgggatgggagttcatcttagcacgctgagccctggagccct   8100
gggatctgagctcagcgaatccaaggtgagggaccagagtttggcctcatagggccacag   8160
acttagaagcacagagacggaatcatggcactggagctgtggctcaaggccgggctctgg   8220
cagtggggccaggtttcaggcgcgggtccagagttgtggcccagccttgggccctccagt   8280
gaggaggggtcttggcccaggtgggctgtggtaggggcagcaggactcaccgatgtagcg   8340
atcgctctcatcgctctggcccccaatggccacacgccgcagcccagcaatgcccgcagc   8400
cgctggaactgtttctggttgatgatgcggcccaggtttggggagctctgggggtcgtcg   8460
ccatagaaacgggtgatggtgctctgcagggcaggcagcagcctctcctgcatctcaggg   8520
ctgcataggacgtagtcgggggccacgcaggtctggccggcgttgaagtagcggaaccag   8580
gccacgcggttggccacggtctggggtcgcagttgtcgtccacgtagcaagggttcttg   8640
cccccagctccagggtgacaggtgtcaggtgcttggcggcagcagtcataacaatcttg   8700
cccacacgagggctccctgggcatggaaggaaaccagagtggccgttcagtgacctggac   8760
caggcgggatggcccagcccacggccccgctcctccctggagaggtggtggagtcagcgg   8820
gcagcagccctcgcctggccttttccttgttcctcactgccaccctgcagcccagggccct   8880
gctcatccttcatcaggaccagcccctaagcacagagtctcaggagggaatggtgcacgg   8940
ctgctatcggcccccagggtcccctgctgagccaaacccttggctcctcccgcctctg   9000
cttgtgaccctggctgaccctgcaggggactctttgcaaaatgctgcatggaaccctcc   9060
ccacccatctcctttggaaacttcggggatcccttatcacccaaggatggagtccagctc   9120
tgtctacggcattcaggtctctcttctctaaacctaaacctggaagttctgccacctgcc   9180
cagcccttttttttctgacccttgaggtggactgtcccaggctgatgcaggcgtccccatg   9240
tcctgcctggcttggcctcacctctcctctgtgctggcctccaggggcccagcagtctcc   9300
gcatgcacacagccttctctgcccctagccctgtctgggcctcaaggcctcctctccagac   9360
ctgactcggggaccacgctgctgcgtctgtgggatggccctggcatttctccccttgt    9420
ggtcaaggattaaagccggcaggagccactgtgccttctctactctcacccctgcccat    9480
cctggcacagtgcttcctgggctctgtggttccttccagggctccttttgcctttgctggg   9540
aggcggccaggtcaatcctgccaggccctttcccacgactgcctcgacctgtaaggcgca   9600
gactcgcctgccagcaccactgtcttcctctcgctcccctctgcccctccctagctcaaaa  9660
actcgaagccgggtgtggtggctcatgcctgtgatccctgcacttaggagaccaaggca    9720
ggaggactggttgaggccaagagttcgagaccagcctgagcaacagagtgagaccctgtc   9780
tttactaaaaatacaaaaaattagccgggcgtggtggtacatgcctgtcaccccagctac   9840
ttgggaagctgaggcatgagcatcacttgaacccaggaggcgcagaggttgcagtgagcc   9900
```

FIGURE 1C

```
aagattgtgccaagattgtgccactgcctgggtgacagagcaagactctgtctcaaaaaa      9960
aaagaaaaaaaagtgacctctggcgtggatttctccaagggcttgtgtgcacattccag     10020
cctgtccccatcctggccagcagggtgaccctgggcaggacactgaggcccagtccctca    10080
tctgcctgcagagagggctgtgggcaccagtagggtggtgtctaagagcctgggggcag     10140
cagggtcacgtatgagggtctggggacagtgggggcagaggctatggttcctgacgctgt    10200
ggttggcacagtgggctggccctggacatggactccatcccttcctaaggggtcctggg     10260
ggtccaggactgctcccagcctggtccagagagagagagaggagaattcagtctcct       10320
gtggactcccagagttagggacaggacccctgagcagctgtcctcccgaccccagcctg     10380
tcccgaccctcgtcccggcctcacctgtgaagaagatgtagtcgaacctgtgctctagca    10440
gctgccccgtctcctggggcccgcccagcaccacagcaaagcagctctgcaaggcgggat    10500
gggtgaggctccttctggggaccccagctccgagaacacaagggagcagcccgccctgcct  10560
ggaccctgccctgcctccaccccgcctggcctgacccagccagggctctaggagggttgg   10620
gtggaggcaaagtggggagaagggagctccccaaggttggctggcattggcaggcccagc   10680
ttggagtccagctggcgctggaggggctgatgccagggccaggtggaggcagacacggaa   10740
cccctgggcaacaggctgccctcgctgctcctcagagggaaactgaggctgacaggggcg   10800
gtgacttggtcaagtttacacaactcagaagaggcaggattgaggtggggactcgggtct   10860
gactgacaggcccttccatgccaggggctgcccagcccttgagccttgcctgttcccgct   10920
ctacctgcccggcagccctgctcacctggtccacgtattggggcagcacctcggccagga   10980
tcttctcgacgttcttgctaatctccgatggcttcagcaccacacagttccctgcagggc   11040
agtgcagggagagagctggaggaggcgtagccagctcctggtctccacacacctgcaggg   11100
caggcatcagcctcacccactttcagatgcagaacctggttcagagaggtaacatgacgg   11160
gcccagggccacacagcccggggacggtggaccagacagtcctctttgccacctgggcca   11220
gttctcccatgtcctcctgggatccatgggtggccctgaggcctcgagcggagaagggtg   11280
accggaaggggcaggcccagctctcacctgcagcgagggctcccacgaggggcaccagcg   11340
tcaggttcagcggatagttccagggcgcaatgatgaggaccaggccaaaggggctccttcc  11400
ggatgaaggcggagtccagctgcgtggcctgggccggggagccggggatgaaattaagtgc  11460
tcagcaccccggcccctcagcagcagctcccacccagaggggccaccctgtgggagcaa    11520
atatcccctgagcccctgcccgcctcagcccggccggctcaccaggttcttgggcacac    11580
gctcgtccttcatccaggcccggagttcctgagggccagggtgacctcgccctggctgat   11640
ggcaacctcagacacctccgactcgaaggctgactgcaggaagtgggtggggtcagggtg   11700
ggccaggattcccagagttggcaggagggcacagcctcctccaggcagggcctgcttcca   11760
caactcattcattcattttcattcattcgttcactcactcactccatgttcagtgcgtgc   11820
ttcctgtgtgaggtgctgtctctgtgccaaacagagggaccggccctgaggccgaccttg   11880
caggggcagtcgttccatgtgaaagtgagaacgctgacggctccattaggacgtggctg    11940
tgctagggaaatcatggagcagggtgggggtggagactgctggagcgtgtggctgtgggc   12000
gtgcacaggtgtgcacatgtatacatccacatgagcatgtgtgtgtgtgctgttttaca    12060
aagcggtcagtgcaggtctccaggcggcggtcacattggagcagtgacctgaagtcaagg   12120
aacaagcaagtcgtgggtactgggaggcggcatactttgggcagaggccctggcggctgc   12180
aaaggccccgaggtggctgtgcgcttgctctgctcctgtttagcaagaagcagagtgggc   12240
aaggtgaggggccaggcagccaggcaaggactcctgagaagagcagggatgggatctga    12300
cttagggttttgttttttttaatttcaaaaaagtttgttttgattttttgcagagtgc     12360
cttgctgtgttgcctaggtaggtcttgaactcctggcctcaaacaatcctcccacctcag   12420
tctcccaaagagcagggtggagattggtccacaggagacacaggcacagccaccctagg    12480
taaatgctgtcagttcccacagcccaggggccagggccactgtcaggcttctaagcagga   12540
gtgaggagacccgaatcaatagggacattgtcctgctctcggctagccagtgctccctgc   12600
cctctgcgccccaagggaggagagaccagccaggcagcaggctgcaggccgctggagaac   12660
aggtcagggacactggggccaggctggctccctggctgaggcagcgcctgaggttatggg   12720
gtgcaggctctcccgggtcagggcagaggggacgggccagtggggtgctggatgggcca   12780
gaggaccagcgaagcccagagaaggagatgcctgcctgaggtcactcagcgaaccaggg    12840
gcaaggccagggctacagctgagccccaagagggaggaagacgccacgcccactggcacc   12900
tcctagccactgaggctgggggaaggtgccttccacacggactttcccacagcctgtgct   12960
ctggccccatgagcctggtggcctgcccgccacacctcctaggtcacctgggacctgact   13020
ttgggagactgggctattttgagccaggttcaaactctggctctgctcttcctggctgca   13080
tgcccttgggcaagaacacactctctctgagcctcttctgggggccactgggtgtggttg   13140
cccaaccagattcaccaaaggggttaactgagagggtgcacgtgacgctgggcagatgctg  13200
```

FIGURE 1D

```
cctgctgagggtggggacagggggggtgaccaggtccagagggagggaccaggttgaatgt    13260
tctgggctactgctgcctttgtagggccccgctcctgcagctgggatgggaaggcaggag    13320
gtggaatcagagccgaagggagaaaagggaccagacagacgtcaggtcaagtctcatgaa    13380
ggccggcaggcggccggtggcagaagctcagtggtggcgggggagtcagtccccagggag    13440
cccaatgggctgggggaaggtctgaacactacagccttcaaggcaaagggaggagatatt    13500
ttgtccagagaataggagccgggggcagccctggggcagatgtgctgaggcaggggcag    13560
gtggtgtcctgaggcagggcaggtgtcctgaggcaggggcaggcaggtgcatgggccct    13620
gatgggtgagggggttgggggaagtgtgtttcttggggttctgccttggctgccactggga    13680
ttgggaggggctgaggccccaagccttcagggtctagacagaggccatgatgcctgctgt    13740
acccagagagaaggccaaggcctcacggcctccgagccctacatagtgtggcccatacc    13800
ccagacctcatctttgctgtttcttcctctccaccccgacagctatgctggcctcctt    13860
gctgctcctcaagcagaaacacccagcacctcctgcctcagggcctttgcacgtgctgtg    13920
cccgctgccatctccccagcatccatggggagcctcccctccatcttcacgtctctgctc    13980
taaagccccccttctcagagaaaccttccctgaccccacatatacaacagcaccctgatc    14040
ctggccccctctctcccctttcaccctgggtgtgtctccagggcacatatttcaacccaat    14100
atgctgtgtaattattatctttattattattttttgagatggagtctcactgtgttgccca    14160
agctggagtgcagtggtgtgaccttggctcactgcaacctccacctcccaggttcaagcg    14220
attctcatgcctcagcctcctgagtagctgggattacaggtgcccaccaccacatccagc    14280
taattttttgtattgttagtagagacggggtttcgccatgttggccaggatggtcttgaac    14340
tcctggcctcaagcgatccgcccacctcggcctcccaaagtgctgggactacaggtgtga    14400
gccaccatgcccggccttgctgtgcaattatttatttgctgttttattgtctccgataga    14460
aggtcatcttcgtaggcatgggaactgtgttttattctctgctatatccccagagcctag    14520
aacagtacctggcacatagtaggtgctcagcaaatagttgctgcatgaatacagaaataa    14580
gtgactggatgaatgtgcaagggtggctctggcctaggggaggagctgcttttagccccg    14640
cttcatggagggcgcaggtgtcttcatccctgctgtcccagctgccctccatgcccccc    14700
tgccccagtgcaccctctcatacccccaaccccagcccaccttgtgcaggtcctgggcca    14760
gtgcgtcgtgcagaagctgcttgttttcttcaggaagcggcccaggccttggagctgcg    14820
cagcccggaactcagctggccgcgtgcgccccgcgtggaaggcctcccgcagtcgccgca    14880
gcgtgtccccaaggggtccatcctgccagatgggtggcatgaactgggtggccagggc    14940
tgccctccttcatgggcaccacccagccgccccagggtctgggcaccctgacctgcct    15000
gcacccacaggggcttgcagacacctctaccttatacacacagggacccactcagatg    15060
accccacagggactgaggctgcctgcaaccccttcacccaacagtgagcactcccagac    15120
acacatgaagaccctcgcaccactcccctctgccatggacctggaggcggctgcaggact    15180
gggtgtgggcttggggacagctgctccaccacagcccccgagggtgagcaggcaggcaga    15240
gcgccatgcttcttcctgccgcacagaaattaaccccaagccatggcctctgccctgccc    15300
tgatgcccctcctggaggcggggcagcctcaccctgccagtctgaatggtgtaagcagg    15360
agcttgatgagtagaggggtgactcactgccaccatggccaccaccttggagcactcca    15420
gacacagaattctccgtcttcctctgtcccagcctggggcactgcccagggaggccag    15480
gccagtgggcaatagcctcttctccctgtgcctcagcttcctcaggaagaggggagaac    15540
acctcgggcctcctggaggccctgctgcccaccctgccggggctgtggtgctgggaggca    15600
gaaacagctgtgggggagaggatcagggcggggagagggcgttcctgcctccgtgctgg    15660
tgccagccagagctggcaggcagggtaggggcctagacattccccgagccctgcctgtt    15720
tacttgaagttcatcggaggagcactctgacgcactcgttcctcggcctggtgccaagga    15780
cccgtggtgacccttcctccttccctctccgagtcccttcctccagatctcagcttgg    15840
ctgatgcttcctccaggcagcccacccagattatgccctcatccactgtcacagtggccc    15900
cttgactctgctcccagcgttctgagttgtgccatgtgataaatgtctggttacactct    15960
acccacctcccaaccctgtccacatctcccttatttccccctcattagactgggaggcag    16020
gccctctgtgcctacttatttgagacctagtgcttgaagcctctcatgttaccggtgta    16080
atgatggcacctgccagctaatgatgagaccacacagtcggttctgagcccagggcccag    16140
catcggtgagcgcaaggctgtgggtgattgttaagtggccaccttgagggcgggacctgc    16200
tccggtctgcaggatggccctgctggaccagtgtgctactgagagcctggtcaggagccc    16260
caggccagccctcagctggagtgattgtggggccaggctgaacccaccatcttcctgctc    16320
tgattgggagaagctgggcagtggcccgcacacaggacaggcaccatggtccccataggg    16380
gatggctcgtcacgggagcaggactgagacccaggagccaagaacgagcctctcgagcca    16440
ccatcaggcctgtctccgggctctgcctcttactggttgtgggaccttgggcaaatcact    16500
```

FIGURE 1E

| | |
|---|---|
| caccttctctgcctcggtttcctcatctgtgaaatggggatgctaatggcacctggtgtc | 16560 |
| attgtgaggattaaatgacatcacgctgcataaaacatttgctgttgtgcccacagaaag | 16620 |
| tactcgacaaaggtcagctctgggtgttttgctaagtagcctgcaaatatttatctccct | 16680 |
| caactccgcactctcctgggtccttctccattctactctcaccttcagacttctgccagt | 16740 |
| ggtcaaaggcaaaccacgcctgtgcctctctcacccttgtaagaatctctgcagaaacc | 16800 |
| acaaaaatgcaaggcacgtaacgtgaatggtggactgtgggcgggagctctgtggggga | 16860 |
| tggagttctgcagggaacattccagcaaccctcctagcaacgctgaaaccaactcaccag | 16920 |
| ggccacaggacacatctctcccacagggcaaccagccctggcattgccctacgggtcac | 16980 |
| tcactctggactgaggcccccagggagtgcccagggcaggaccctggcaagcggagaagc | 17040 |
| caaggccgccttctgcctgagattgggggatcctgggcctgttatctcccgagggtgct | 17100 |
| gggcagccattgtggacacacagaatagggaactcctgaatcaggcactgggctggggtc | 17160 |
| ccccaagcccaccccgcggcactcatcccacagtgtgaggttgtaaggagtgtgatccc | 17220 |
| catgcctgccctcgctcatttcaccaccacggccgcccactgagggaccactattcaccc | 17280 |
| cactgaaggagatggaggctgaggctcagagagggccagagcttgcctgataccacccag | 17340 |
| ctcctcacattggaaaacccaaatccagaagagcagaaggctatccacctcagctcccac | 17400 |
| ctccctcacagtccctggggatgggcagccaagtccttggggaagggacactgggctg | 17460 |
| gggcctggacggcagacccaaggctgggtggactccggtaggccagctgtgggaggggtg | 17520 |
| accggtgaggggaggtctcttgctgtttggattccatttcctcggcctccctcctcacta | 17580 |
| ttgctgccactcccacactgcttaggttgtggggtctgagactgcctcttgcctcctgc | 17640 |
| ggctgagccactgaggtccaggggctgatgggcccaagggtctctgggcgtggccccc | 17700 |
| atcacaggttgaggtgcatttggcccagacctgcagcttctggggtgggggggagttgcc | 17760 |
| acatcatttggtgatgaagatagcggctgtttcctctggcctggggccagggcaggacc | 17820 |
| agccacttcctctcaaggccacgggcctctaaaaacaatactcaggtgcccatgtgctgg | 17880 |
| gcactatgccagcctgggtgctcgctgtgggtgcccacaggctccgggaacagagtgggg | 17940 |
| aggaacggggctgacatatcacagggagtgaatggctggccgagccgctgcccccaacct | 18000 |
| cacagcagggaccgtccctgggcaggactccctgctcgttcacaccctggcctatcaag | 18060 |
| tgggttggattccagggaaacggaggctctgcccgttctctcattcttcctgcctcagtt | 18120 |
| tcctcatctacaccatgggccttctaagagcatcctcccagcatggcatggtctggggc | 18180 |
| ccaatgacctgggtttaaactgcagcaaccacatgtgtgagtggggagaccttgggcagg | 18240 |
| ttgcttgacctctttgtattcacgtttcccatctgtaaaattgggcactgcctgtggcac | 18300 |
| ccataccactgtcgggagaattcaagcactgggaccccgggaagtgctcagtatccatgg | 18360 |
| aggacggatgtaccagaggagggctcagggaggagacccctggggcaggggcctgaaggg | 18420 |
| gccttgatccaaggtgggtgttggggagacaaggacatcaccctgagacccaactgagga | 18480 |
| cagggatgtggtgacagagggactgaacatggtgggtagagggcctgggggaccccatc | 18540 |
| agggcagccagaaggcggggatcactaggccaacttcaggggacccacaggcccaatacc | 18600 |
| gcagggtctccgattctgatctcctgcagtgtagcttcattaaacaaacatgatgagagg | 18660 |
| ctgtgattttgaactgagctcctgtactaggccccaacagaccagaccaaaccaaaatgg | 18720 |
| aggcactcatgccaaatgccacatcatcaaaccgaagctttaaggaagcagacagagccc | 18780 |
| aaaaccacagaccagtttctccgggaagcaggagattccagtccacctgagccggcatca | 18840 |
| tcaggtcccctctgccttaccccttagaaaaaagcagtccgcttagaaaaaagcagtctg | 18900 |
| cagcgatccggtattaggcggtttggtgtttcctattttctgtttcctcctttctgcct | 18960 |
| tatgaaccccctgctctgccactgcctggtgggagctctcactccattttgtagaatgga | 19020 |
| ggctgtccggattcacgaatcatgaatagaagccaatttgatctataactaaatgtgttg | 19080 |
| tcattttgtcttttgatggccttaagctggattttcatgaggcctcccaaagctcagcag | 19140 |
| cccctcccttggggagccagggaccagcgtatcccctcattggtggctcgggccaaccca | 19200 |
| gccccgggtcacaaagaggctgaacagcctcggctccctgatgggcacagttcccggga | 19260 |
| tgagaagtgcctcctgcaggcggggcggggctggctggccactcctttcttggaccctga | 19320 |
| caaagtccattgctaagaatgattctttcccagagtcattcatggccacatccctgcatc | 19380 |
| agcactgggcatgcaggctggtgcccaggaaacggctgttgctggaagggatacttgacc | 19440 |
| cctgtggggaaggggcgcacagtccttcctggggcagctggacccagagctgttcccttg | 19500 |
| gttcccttggagggtgtccgggaatccaggaaaaggaggcggtggcaacccagctcgga | 19560 |
| caacggaagggtgcctgctggccagggggtgcccgggacctcgctgccactccccagat | 19620 |
| ctgcctctcctccttccgctttctcccccagcaggcaggcagatgagctcagccaggaca | 19680 |
| cagtggcctctgagtgcagctgccggtggctaggcccgcctgggctgcctgtaacccgga | 19740 |
| gttgctgagctggactctggcccgactgctggcccactacagccccagcctccccgggat | 19800 |

FIGURE 1F

```
actctacctgaggctctgccaagctgcccttcctcctggctgtcccgctctgcctggtgg      19860
ccctgctgttaagaaatgtccaacgcagggccagtccccggggagggtggggcggagt       19920
tgccctagcctcgtgcctgactctggctctgggcgggctggaggctgcaagccaagattt     19980
caccaccgcctccctcgggggcctcgacatctcctcccagaccacagagaagaagtcaac     20040
gcccagagggcgccaggctagagccacacagcagggctgagctccgagctgaggggcagc     20100
ctgaggaggaggaggagaggctgtgcagcagggctgagcactgagctgagggccagcctg    20160
aggaggaggagtggggcagtgggccctgggaatcccggtgtggggtggggaactattatt    20220
gtattaattatattctattataatattatgtggaatgttatggcccagaatagcaaggaa    20280
gtctcgaccccccactcccagccttccctcaatgcctcccctaaggaataagaccactac   20340
tactcctgctgccctcctcctaccaccttgcctggtttacaagacaggaggaaagagaga    20400
aggcaaaaagttagaaaaaaacagaagtaagagaaatagccagaagaccttggcgccacc   20460
acctggccctggtagttaaaaaaaagtgataataatatcaacccctgacctaaactactt   20520
gtgttatctgtaaattccagacattgtatgagaaagcactgcaaaactttctgttctgtt   20580
agctgacgcatgcagccccggtcacgttccccgagcttgctcgatttatcacgaccctt    20640
tcacgtggaccccttaaagttgtaagcctttaaaaaggccaagaatgtctttttcagga   20700
gctcggctcttgacgcaagtctgctgatgctcccagctgaataaacctcttccttcttta   20760
atccagtgtctgaggtgttttgtctgtggcttgtcttgctacaccctacccaagactcag   20820
tttccccttctgcaaaacaaagaggtcagacccaaaggtggctggagtctagaaatacca   20880
tcttagggaccatacctcatgcctgctcctctcccagcgccctgtgcttccgtgttcctc   20940
cacaccaccccatgggccgccccattcatagagcctgtctttctgcagatctaacatttt   21000
acaaacgaggaagtgggggcagagaggggtgggatgtgaacatggggcgtgtgtgtggc   21060
agagcttcttgctccagagctggggctgcacccgttcggatgtcccctctgcctcccag    21120
gaggagtgcctgcctctctgcttaggaccgtggtcatgatgccacgtgtcgccttggtgg   21180
ttcctgtagtcccgatcttcctcaagttcggcacaggcagctgtgcctaagcctgtccct    21240
gcctgcccccagcccgccccggatacacctgtcagagccagcgtgctgtggggatgatgt    21300
gcaagctgctgtgggtgtggacaggcagggacagggtgacaggtgtggaggaagagcct    21360
cctctatgccccttcctgggcctgccgctgctaccatctccctggtgccctgggcctccg    21420
tagctcccggccccggggcctctgggccaacgtggcacctgggaggtgctcatcatggcc   21480
ccccccacccgccagctccctgcctacctgggagggcggtgaggtcttctggaccatgcc   21540
cacaccggtggcccgтgaттagatagттaggгtgggggтgaaggactgcagagccсctgт  21600
cctctgtgtgggatggagcccccagccactgccagtcacgtggctcagcatgtgacagcc   21660
cagccctgccattctctggagctcagccagattgagcgggtgccaggcagggctgggcag   21720
gggctgagcctgtaggtctcagctgggagtgaggcccagagagggcagccactggtctaa   21780
ggccacacagcaaatcagggacccatcttggcgggtactggcaggtgggaggggtgtttc  21840
aggatcccgagggtcccctccctggccagggagctgttgaagaatttcccccaactcaca   21900
ggggccgaacttgtcatgaatgcaggagcaacctgggaggaggcccccgaagaggcctgt  21960
cctcccgggacagaactcctagccttccctgggagtgaggctccccccaagggaggccac   22020
acacctcccaggagggctgggccctccccactctgggttgggtgcccctcactactcctc   22080
aaagctccagaggctcagtagggcctgggagtcccatctttgttgaggagcccagggtaa  22140
atggggagccctctgggtagggcaccaggaggactcattttggagccagctctggggtg   22200
aggtctgccaaggcccaggccagccaggggagtgggtggaggggttgctcagggctccg    22260
ggccagacagctgcggccccgcctgccctgcctcctccttgctgggctgacgcttcgcct    22320
ctttgggcctcagtgttcccatgtgagaatggggctgactacagtcccggggcatctgt   22380
gggtgaatgagagggttcggcaggcatggatctcagcacctggcatggagggcgttaagt   22440
gtgaggtctgggctcaaatcctggtcctgtcacttacctgtgtgacctaggttagtgtct   22500
taacccccgtgcctctgccttcccatctgtaaaatgggacataagtgattgtgaggctg   22560
aaacaagttattccatgcacgtgggcccggaactgtgaccattccaagtgcccggccccc   22620
tctggaagggtctgagagctaccttccagactctaggacaggagtgtgggcagggcatga  22680
gcatggcatcaggtggaatcattcatccattcataattcattcattcattccctcacttc  22740
tcagaaacacgcccctgagcctggctcacagggcctcagacctgcccaagagcatctcac  22800
tgcctcatctgcccacgagtgaccttgaaaagaaacgtcccctcactgggcctcagtttc  22860
cccagctgtaaaatgggggctgactctgcctgcctcacatggctactgcgagggtgaaac   22920
gagagccgacctgaaggcaccgacagggcacctggttctcagtaggcgctcagagcatgt   22980
gaatgtcctcctgcccctctccttgccctcctgaggaagtggctgccccaggccttggcc   23040
ctgaggccctggccctgcctcccaccccctccctggcagtcttgaaggctggacccaccc   23100
```

FIGURE 1G

```
tggctccttgaagaggcaaagttagaggctgtaggggcccagggcccaggacacagtcag    23160
aactcacgggcaacggtgaatgcgggtcacttgttcatttacgcactcaacaaaccttta    23220
ctgagcacctactgtgtgcagacacttcacacaattttcacaattcccagacattattga    23280
ccatgctttccagctgggccacacagtgacaaggactcatggggatccacaaccagcctg    23340
gcctggctccccggcccacggtgcttccaaggtgcctggagccctcgcacaggaatgggc    23400
tggagtcttcagctctgggtgagccctttgccaccaactctcaggagcctcaagtctcag    23460
tggaaagcagcagccacctgggcatttgctgtgccaggcactgggcagagcctttggcac    23520
accccaacctggggacctcccaccatcctgtgagccagactcagtgatcatcatccccat    23580
tggctttaatgtttaaaatattgtggaatcacatccatgccagggaagtggtgtgaaggg    23640
aatcacgtgggctgcccagcacgctcctgtgtcagtgcaatgcggggcaacaatattcca    23700
agaggttgtttcagggagttccagttgagagcaatatttattctcttctgcttgcttttc    23760
tgcaaggaacatcgattattttcataatgagaactgaaagtaaaggcttattatagagaa    23820
aagcattggcaaacagtgagcacggggggatctggccaccccttcctggggatgtgactg    23880
tgcactgttgcaacctggatggggttggtggaggtgctggccctgctcagatctctgtcc    23940
gcaggtcaccctggtgtgtttatctgggccaccctatcagcctcttagatagtctccagg    24000
ctccccaagagcagctccataaaccacctaaaaaaaaaaatcctttctggagagaggagg    24060
tgtatcagtcagggtttagtgcctccagggctgttttttgttttttttgttttttgtttg    24120
tttgtttgtttgagaggtctcactctgtcacccacgctggaatgcagtggcacaatctca    24180
gctcactgcagcctcatcctcctgggctcaagcaattctcccacctcagcctcctgagta    24240
gctggggctacaggtgtccaccatcacaccaggctagtttttgtatttttgtagagatg    24300
ggttggggggggggtttgtctcactttgttgaggctggtcttgaactcctgagctcaag    24360
tgatcctccttggccagccaaagtgctgggattgcaggcgtgagccacagcgcccgaccc    24420
tctccaggtgttttgagtaggagacattgagtgcagggaattggtggtacagcacaggtg    24480
atggaagagcccaggatgggcaaccatagcaaccgccacaaccccaggcccagaggaac    24540
aaggggaggaagagattgcaccaggccccagaagtttggggtccctcagggaaattgaga    24600
agctcgggggcccactcccagcactttgggggctaaggcgggtacatcacttgaggtca    24660
ggagttcgagaccagcctgggccaatatggtgaaaccccatctctactaaaaatacaaaa    24720
atcagctgggtgtaggggcacacgcctgtaattccagctactcaaggctgagtcagga    24780
gaattgcactttctcatcat**A/G**ctgtgtaatgatgctggtgtctgccatctgagaacggcc    24840
cccgccatagccatactctcccacctcctccctgcccctgcgcctcgggccctgccctct    24900
cttcggctcctttcctgtctcccacttccagccacccacc**T/C**gcatgaatccacctgtctg    24960
ttccccacatctgcacttgggcatcgtcacctggagaaagttctacctcctggaagcctg    25020
aagccactgcagattcacgcctccccccaccttcccagcaatccttgcgggtgggaggt    25080
gtttgtcatccagtcactcatgcacccatccagtcacaagtattgatcactcagtaggtg    25140
cccaatgccatcctctgcatttgggagaggatgtacctaaagagcagtgggtggaggggg    25200
gtgcacagggagggcatggaaaaccagaagggaagtgaagggactgcattctctgcaggg    25260
atggtctcttgttctgagagctgagtgggaaggaagccacctggaggcgcagcaggaag    25320
agcattcaaaccagaaggaacccaggggagagaatctggatattttcaaaagtggccccg    25380
tggctccagccaggtcggtggtagccagtgctttggagtgtcggccccaccacaggctcc    25440
cgctgcagcccgggatccagtgcccagcaggatgggggcaggtggctctgggccccacta    25500
catggttgtggcagggtcccccatgtagttcagtggggatcacaatctccacctcccagg    25560
acccactcaagctcccatttgcacagcccaaactggagcaggatggggacatgggaggtg    25620
ggctctggctgtagcgtccggtggtgggaggtggggtccaggtggtgacgctactgtccc    25680
tgcagtgctctttgatgagctgtaacagcaggcttggaggtggggctggggacgacccag    25740
gcaaccctgaggggagcttaagggagccaggcaaccctggcacttttccaaggctttgca    25800
ttaactcaatagttccgccatggccccggggtagtgccatgtatttctgttttaccgtc    25860
gaggaaacggaggaaaccgaggcacaaagaaatggagttaattcctaaagtcacagggcc    25920
aggaggtggctgagtgggattcgaactcacaccccagagggcacacacaggcaggcccc    25980
tgcacacacgcgcgcgcgcgcgcacacacacatacacacacgtgtcctggaggagg    26040
cggcccgcagggcgggacagggcggggcggggcaggtcccggccgccgggaggaagtgg    26100
ccggggcggtcgcagg*gactccggggcgaccgccgcgagtccgcagtagttcgggcc***atgg**    26160
aggcggagccgccgctctacccgatggcgggggctgcggggccgcagggcgacgaggacc    26220
tgctcggggtcccggacgggcccgaggcccggtgagcggggacccggagtgcgaggcgc    26280
gggcgtccctgtgggccagggtcccccggcggggcggggcgggccggggcggcgg    26340
gcaccgggggacacgggttcggggcgcgatcgcgggtgcgagcggcgtgcgtggctcgca    26400
```

FIGURE 1H

```
gctggacgagctggtgggcgcgtaccccaactacaacgaggaggaggaggagcgccgcta      26460
ctaccgccgcaagcgcctgggcgtgctcaagaacgtgctggctgccagcgccgggggcat      26520
gctcacctacggcgtctacctgggtaggtgccgctcggggacccggggccgccccgcccg      26580
ctcccagcccggcccgggaaacagaaaccgcgggccgccgcctcccgcccgctctcactt      26640
cccctccgctgccctcgcagctgcagccacggcccccgcggcgggggtggggttggggg       26700
gtcaagtagcgcagcgtccccgggtccagccagagcctcggtgtgggtgggggacgggg       26760
gtccgggctccggacagacctgccaccgtcagaattggaggccggcggagcaaggcggg       26820
tgggggtctggcttagctggccaagtggccgcgggctggcagaaggcgtggcgcagccc       26880
gggaacccgctgtcctgaggggcgctgtcagcgggaatgccttcggtgattggagctcc       26940
ctgcgaggcctgcatgccgtcttctgctcggtggcgcccaaagctaggctgctccctgca      27000
cgccgctctctgtcctgtcccaggcctcctgcagatgcagctgatcctgcactacgacg      27060
agacctaccgcgaggtgaagtatggcaacatggggctgcccgacatcgacagcaaaatgc     27120
tgatgggcatcaacgtgactcccatcgccgccctgctctacacacctgtgctcatcaggt     27180
gggcgcggctgctcctgtgggatgctgcggtactcccatttcggaggggtacagaggccg      27240
gcgggccaggaggtgtccatctgccggggtgtttgtggggcgagggaacaagggagaggt      27300
ttttttctacccggaagcctgagagtgaaggggtgaaactcggatttggggaaggaaac      27360
aggaactttgcctcagggcacatttggtttccagcaacagattcacacgggctgagctcc     27420
ctcccagcttgcctgggcctcacgtggcaccctcctcgtggcctccttggaggcctccca     27480
gagccactgtggccttcaggttggggctgtagagttagggggtttctgatcggtcagcaa    27540
agtccaggcacccatgcctggcccagtcgctgtgactggtgctgaggggggtgtttctcac    27600
agacaggcatggctgggcaggtgccccagagctctccccagatC/Gtgagccctggaggta    27660
tgtggttcagcctccccatcaccggtccacagtgccctccctgatgggacctggagacca    27720
gtggacaaattaggtgaatttgagctccctcatctttaaaacaaacaaacaaacaaaaca    27780
acaagagaaaactccatttaaacaaaaatttgaaatttaaaacatctcccgttgcacag    27840
gcaggattagaataactgaaatcataaaaaagaaacccatctaagccctccaggaaatc     27900
ggctacccatgctgtcccaccagcatgcatggattacattcacatccttgtcccagagc    27960
acgtgtgtggacgtgcccgtgtgtgtgtgtgtgtgtgtgtgtgtgtgtgtgtatgcaa     28020
gcgggctatgtttgcttttgcttgcttacttttttttttttgagacagatacttgctctg     28080
tcacctagactgcagtgcagtggtgtgatctcggctcactgcaacctctgcctcccaggc    28140
tcaagcgattctcctacttcagcaccctgagtagctgggattacaggcgcctgccacccg    28200
gttaatttttgtacttttagtagagatgggggtttcactatgttgaccaggctggtcttaa     28260
actcctgacctcaagtgattctcctgccttggcctcccaaagtgctgggattacaggcat    28320
gagccacagtgcccagagcttgcttccttcttttcactgagcatatcttagcctactcta    28380
cagccttcacagttacgactttgcaatggtagcatcttctgcagatacggtggcactgaa    28440
cagtggcttggaattggacactgcagttccttctgtgcttacatctgtttccttgttttt    28500
ttttttttaaattatgtgtttatttattttattattattattatttgagacagagtctcac     28560
tctgtcacccaggttagagtgcagtggcacgaacacagctcactgcctcctcaacccca     28620
cacactgggctcaagcaatcctcccacctcagcctcccgagtagctgggcctacaggcgc     28680
acgccatcacatctggctgattttttaaagtatttgtagcgatggggagttgctatgttgc    28740
tcaggccagtctcaaattcacccgccccagccccacaaagtgttgggattacaggtgtga     28800
gccaccacatccagcactcccccaattttttaaacaattattttttcctaggatacatttt    28860
caacaatgtctttactaggtccaagccatacaaaggctttatggcttttgaaacctatc     28920
acttctactaatagcagtgaactcttgtctcctgtctgcccgacactctattttatttat    28980
ttatttttattttttacttttttttttgaaatggagtctcactctatcaccaggctggagtg    29040
caatggcacaatctcggctcactccaacctctgcctcccaggttcaagcgattttcctgc    29100
ctcagcctcctgagtagctgggattacaggcgcccgccaccacgctcagctaatttttg    29160
tatttttagtaaagacggggtttcaccatgttggccaggctggtctcaaacttctgacct    29220
caggtgatctgcccacctccacctcctaaagtgctgggattacaggcacgagccaccacg     29280
cccggccgtgctgggcactttataagcgcaatttcattcccaataatttgaggaagctgc     29340
tccagtcttagacatgaagaaaccatggtgttaaacaacttgcccaggtcccacaggcag    29400
taactggcagactgaaggcttgaaccccagtagagggactcaaatccacatgttcacccc    29460
ctgccaaaactaccaggctgctttcccaaagggttatgccagtgtgtgtgaccactggct    29520
atatgtgccactttttttttgagcaatcttgctgttgcccaggctggagtgcggtgacgc   29580
gatctcagctcacggcaacctccacctcctgggttcaagcgattctcctgcctcagcctc   29640
ccaagtagatgggattacaggtgtgcaccaccacacccggctaattttttgtatttttagt   29700
```

FIGURE 1I

| | |
|---|---:|
| agaggtggggtttcaccatgttggccaggctggtctcaaacttctgacctcaggtgatct | 29760 |
| gcccacctccacctcctaaagtgctggaattacagatgtgagccactgtgcctggcctat | 29820 |
| atgtgccactttcaaaccacatcctcaccagcagtgaatgcacattttactggcatttt | 29880 |
| tacttaaggagcataaatacagaaaacttgaagataccagtagtggttttggcctgatc | 29940 |
| agcctccatggtggttgagccctcatcctgtcactcaccaagccccttctattgtcact | 30000 |
| gtgtgaccttttcccagacccagagaggtggaaacttcctgactgaccaccatggttcat | 30060 |
| aaaagcaatggactggaggcagggGtgccgggactctggctctgctgctcccagcagtgg | 30120 |
| ggcctcttcctttctcttctcccagcctgagtcaagcccctgggccctacagacacagtg | 30180 |
| catgagcttgggaggagaaggggGaatgggagaatcagagagcccagaacacgcatgagg | 30240 |
| gctggttacacccatgggtcactctccatcctcacagtggtgatgagaggcctgtggttt | 30300 |
| gggctccgtgcccatattacagctgggaaaactgaggcacagtagcttgcctgaggccac | 30360 |
| tcagcaagtctgtgtatctgatattccatctcagtgccctcgactctctctacctcacaa | 30420 |
| agccctgtgagctgggacctgcggttgtggcccgtttggcttcaggccacagtggtcca | 30480 |
| gcaggctgtggtgccagcatctctcccactgtccgcaggttttttggaacgaagtggat | 30540 |
| gatgttcctcgctgtgggcatctacgccctctttgtctccaccaactactgggagcgcta | 30600 |
| ctacacgcttgtgccctcggctgtggccctgggcatggccatcgtgcctctttgggcttc | 30660 |
| catgggcaactacatcaccaggtgagcctggtgggcagcagggcaggaggctggagacct | 30720 |
| ggccaagcctccactttattgccaactttggctgggggaccacaggaagccccttccgcc | 30780 |
| ctctgggcctcagtttccccacaccggggctggtctgctcctagctctgggtgcaggaca | 30840 |
| cacaggagtggcacaggtcgggctggggagagccttctctcctttgtggtccaggatggc | 30900 |
| gcagaagtaccatgagtactcccactacaaggagcaggatgggcaggggatgaagcagcg | 30960 |
| gcctccgcggggctcccacgcgccctatctcctggtcttccaagccatcttctacagctt | 31020 |
| cttccatgtgagtgccacgtgggccattgttgggtggcaggggcagacccacgcattgga | 31080 |
| gcccatccacagtctcaaccctctagtcccactttctttcttttattattgttatttta | 31140 |
| agaggcctggtctcactatgttgcccagatggctttgaactcctgggctccagtgatcct | 31200 |
| cccaccttggcctcccaagtagctgggactacatgcgcacaccactgtatctgccccacc | 31260 |
| ttcatttctttttctttctttttttttggtgggggttggggcagggtcttgcac | 31320 |
| tgttgcccaggctggagtgcagtagtgcagtcacagctcactgcaaccttgaactgctgg | 31380 |
| gctcaagtgatcctcctacctcagccttctgagtagctggcatcatatgcgtgtgctacc | 31440 |
| acaccagctaatttttatttttgtagagataggatcttactatgttgcccaggctgc | 31500 |
| ccatcttcctttcttgagcccaccccagcttgctcatccatagagatagagatctcatct | 31560 |
| gcccttttccacaatgctggccaggaggaggtcttcctcattgggcggccctgtaaccac | 31620 |
| actactcccagaactggaaggcccctgttcccccaaggctgtgcctggacccctcccca | 31680 |
| gaccatgcctgtgtcccttgcctggctctgtgcctgagtctggtcccaactgcccttgtt | 31740 |
| tctgcagctgagcttcgcctgcgcccagctgccatgatttattccctgaaccactacct | 31800 |
| gtatgacctgaaccacacgctgtacaatgtgcagagctgcggttagtccttgttgggggt | 31860 |
| tggggaggagtccacaaagcctgcttacttccccagcagacactgggccctcactcacag | 31920 |
| gattcagggctggcagcccagtgccccacggctctggtgggcaagacacagggccctgta | 31980 |
| ggagtaagtagttaggacatctgacccagccaggagagtgggtgggcggggaagactgcc | 32040 |
| tggagaaggcaccatctgggctgaggctgccagtgggatctttcttggggccaggcaaac | 32100 |
| agtcagagctcaatcagtgcagggggtgtgcatggaaatgtgaggtccactgagccttgg | 32160 |
| ggA/CaataggggtgggaagcagggGaaagatgccccttcccggggaacacccagccccagt | 32220 |
| ggtccaaacccagccccagtggtccaaacctccaaactgctctctgaaggaactctgccc | 32280 |
| ttgctctcactctcccgccctccaccgctcctccgcggcctgcgtggctccaccctggtg | 32340 |
| gctggattgactgtgtgccctactctctgctcacggtgccctcaccccacccttcccag | 32400 |
| gcaccaacagccacgggatcctcagcggcttcaacaagacggttctgcggacgctccgc | 32460 |
| ggagcggaaacctcattgtggtggagagcgtgctcatggcagtggcttcctggccatgct | 32520 |
| gctggtgcggcccgggatggggcaggacagtcagtgaagcagagtgtggttctggggac | 32580 |
| cgagtctgcgagaaagggtctggatcggatggcA/Gtggcctgggtcgggttgtggcctcgg | 32640 |
| ggcaggccgtaggcctgggagcgcgatctgagttggggagctagggccgagtgctgcaga | 32700 |
| gcgggcatgaggctcggaggcgggctgaggcctgtggtccgaggcaggcgtgggcatcc | 32760 |
| agaggccaggggaaggagggaacaggcttggtccacagtttcgagctggagacaagatct | 32820 |
| tagaagactgactgagacctgtgaggggttggggacaggaccaagggtgagggctggaa | 32880 |
| ggtgtggctcaaactggaagtgatactggacggcagaactaaggcgttggcatgctgcag | 32940 |
| cctggcgatggagctggaggcaaggcccagtccgtggctgtgtcaggcggggcctagtg | 33000 |

FIGURE 1J

| | |
|---|---|
| ctgggacgcggggccgaagtctgtgggtgtgtccgaggggcggggactagcctggaaggc | 33060 |
| ggggctgaggtctggcgcggggctgagaaggaaggttgaagtctatggatttgtctgaat | 33120 |
| gtgagttgtgaagtgtgtgtatgtgagagagaggggatggggccttgggctggggaggcaa | 33180 |
| gaccaccgtctttcggagtgtggtggcgtggctttgtgctgagaggcggggccttgagct | 33240 |
| gggataaggcaagacctgggtctgtgggagtgtctcaggggcggggccctggtttgggag | 33300 |
| gcggggccgagctgggcaaggcccaggcacgtggtgcatctgaagggcggggctgaagc | 33360 |
| ctggaggccaggcctgggcctggctggccgccccttcaagtaatgggttcgcaggtgctg | 33420 |
| ggtttgtgcggagccgcttaccggcccacggaggagatcgatctgcgcagcgtgggctgg | 33480 |
| ggcaacatcttccagctgcccttcaagcacgtgcgtgactaccgcctgcgccacctcgtg | 33540 |
| cctttctttatctacagcggcttcgaggtgctctttgcctgcactggtatcgccttggta | 33600 |
| agtacagcctgcaaaggattgcccgacaaaagacaagatagccaggtaaatttgaattca | 33660 |
| agtaaacaaagaataattttttaattacatatgtaagtgtgtacatgtatatcccaaatat | 33720 |
| cccctcctgctttctcttccctctcttaccccgtccccctttaccttgggcaagtta | 33780 |
| ttttaacttctctgaatcgaaatgggatagcacccacagagtgtttagttccttgtgggg | 33840 |
| tacagcccacggtgtctagggacattccaagcattttcacacctgccctcagaaccttcc | 33900 |
| cctgagccttggagcgaggtcaggcagtccagggagggcagggtgtggcctaaggaacac | 33960 |
| ctcttgtggggagtaagagccagcccttctccccacctggctcttactccccgtatcgcg | 34020 |
| gggggcccctctccccaccctggctcttaggacccccatcgcaggggggtaaggcacccc | 34080 |
| cccgcgatgcggggagtaagagccaaccccctcttttccccccgactcttaggacccccat | 34140 |
| cgcaggggggtgaggcacccccacgatgcggggagtaagagccagaccctcttccccc | 34200 |
| tggctcttaggacccccatcgcaggggggtgaggcaccccgcgatgcgggagggctga | 34260 |
| gactgtggtctgggctgttccagacttcaacactcacccccttgtcccccgcagggctat | 34320 |
| ggcgtgtgctcggtggggctggagcggctggcttacctcctcgtggcttacagcctgggc | 34380 |
| gcctcagccgcctcactcctgggcctgctgggcctgtggctgccacgccggtgcccctg | 34440 |
| gtggccggagcaggggtgcacctgctgctcaccttcatcctcttttttctgggcccctgtg | 34500 |
| cctcgggtcctgcaacacagctggatcctctatgtggcagctgccctttggggtgtgggc | 34560 |
| agtgccctgaacaagactggactcagcagtgagtatagctgtggggcactgggggggggg | 34620 |
| ggcggggcagggggctttatggctatctgtgggtggttggcgagacatagacatcccagg | 34680 |
| gacagatatggggtcccatggtcacataggtcctgtggacatggcagaggcaggtgggg | 34740 |
| cttcctgtggacactccgggggtggaagggaagtcttatggacacactggggacagatgg | 34800 |
| gtagggtgtggacaccctggagacaggtatgggggttccatgccatggacattctgttaa | 34860 |
| taccccagagcgggcacagggccccatcaacactggagggtcagtgtgaagtctcgtggc | 34920 |
| tacatggggcaggtgtggggctctgtggacacccttagggacagtgtgaaaaacacatc | 34980 |
| aggattctccctttcataccaggggacagggcttaccctggcatagttttcatgacac | 35040 |
| ttggagcagatgttttggtctctgcttcacggagcatgtggtaggagcaagtggcctgtt | 35100 |
| gtacacccatggcatagatacagacatgggcctttgtatagagaggagcaggcctgcagc | 35160 |
| cccaacccagtctgctcagtaccagagtccaggccccaggtctgggctgctggggaacag | 35220 |
| ggccctgtttgcagaaggcagcgggtgggcccatgttcagctccaggatgctccctgacc | 35280 |
| acagatgggcacacgcagtgaaacacagctagcacacatgggcagtcctgccgggcatcc | 35340 |
| atgtcagtgtctgttctgatgggccgaagctgtgaacagttttgaacgtcatccttgggg | 35400 |
| gtgtggagtagccgaggtcatgcctgctgctggcagggcggaggctggctctgtgtctct | 35460 |
| gtctgtagcaggggctggagcctcatactgcaccacagtctcttggccgttttgcccaag | 35520 |
| gatagccaattctgggcagagtccagcctgggtatcttgaacccatgttgtgccctgtct | 35580 |
| ggtcctggcatcccctctgcccagctccatatcccatctcctccggtgaaccccgggggg | 35640 |
| tccttgtctcttcatagcagcactgtgggggtaaagtcaccctgcagggccccaaaacag | 35700 |
| gagtgttcatatcctgagtgcctggtgaaggtgttaatagtggccctatgatttggcag | 35760 |
| gtgccatgcccactttctcactttagaacttcagaacacagcacacaataggcataagct | 35820 |
| catctcaccattgggaaaagcagctctggggagttaagtacccaaatcacccacagagcc | 35880 |
| aacattacagccctgagaacgagcgtgcatcttctgactcccaatccattactcttgttg | 35940 |
| cccaccctgggaggactcactggaaaggaatccccctctccatgcttagcttcaggttt | 36000 |
| gatttgcagagttggcagctgcaaacagttcgatctctctagtcctggctgaggaggaga | 36060 |
| aacagcgcctgcaagcttggcactgcacacctgggttggggacaggacatgactaagcac | 36120 |
| agagctttcttcttttgaggccacgcatgtggtgcggagcgggaacacctgcatccacac | 36180 |
| agcccgaggcacctgctcctacttctgcttagcgtgtgagcagtgtggtgaccagggtct | 36240 |
| ccaccagggggcaggccaggaccgcctcacagcactttctaggcgctctctggtccgggg | 36300 |

FIGURE 1K

```
ctgggacccatacagggcttagtaaagttcgtagatggtagctcggtagccccaggcccc      36360
aggtgacacctctccctgcctgccctgtactgcctgcctgcagcactcctgggaatctt      36420
gtacgaagacaaggagagacaggacttcatcttcaccatctaccactggtggcaggctgt     36480
ggccatcttcaccgtgtacctgggctcgagcctgcacatgaaggtgagactgggcagggt    36540
tgggggccccatgcccaatgacaggtacttccttagcccctgccctggcttcacagcttc     36600
ctaaatgccaccccttcccaagccagtctctgggccaaggccccattcctgcagcccact    36660
gggtggcccccaactcagcaccccacttactggcccacctccagccagtctcagtttgcc    36720
catctctgaggggatttgtgggtgcatcacagccatcctgtgggctgtttggtaccttgt    36780
tctccagatgtgggtctgtctctcttcatggcctgaaggggagcaggctcctcatgctc    36840
tgctcacaaaaaatggtggctcggtctagcaagtcccagttgctaaacatttttaaaaa    36900
tagaactaaaggccgggcgcggtggctcacgcctgtaatcccagcactttgggaggccga   36960
ggcgagtggattgcctgaggtagggagtttgagaccagcctgaccgacatggtgaaacct   37020
cgtctctactaaaaatacaaaaattagccgggcgtggtggcaggtgcctgtaatcacagc   37080
tactcaggaggctgaggcaggagaatcacttgaactgggaggcggaggttgcagttagcc   37140
gagacggggcgttggcactccatccagcctaagcaacaagagcgaaactccgtctcaaaa   37200
taaaaataaaaatagaactaaaaatagcagggagtgggctggcagtagtggctcacgcct   37260
gtaatcccagcattttgagacgctgaggtgggggttctgagatctggagttcgagaccag   37320
cctgggtaacaggctgtgaaactctgtctctactaaaaacacaaaaattagctgggcatg   37380
gtggcacgtccctgtgatcccagctactctggaggctgaggcacaagaatggcttgaacc   37440
tgggagatggaggttgcagtgagccaagatcgcgccaccgcacttcagcctggaggacag    37500
agcgagactctgtcttccaaaaaaaaaaaaaggaaaaaaaaaaaagaaaagcagtgagt    37560
gggctgggcatggtggctcacgcctgtaatcccaacactttgggaggctgaggcaggagg    37620
attgcttgaggccaggagttcaagaccagcctgggcaacataggagaccctgtctctaca    37680
aaaaatttaaaaaatagctgggcgtagtggcgtgtgcctgtagttccagctacttgggag    37740
actgaagtgggaggatggcttgagcctggaagattgaggctgaagtgagcgtgccactgc    37800
gctccagcagtgggtgggggaagggagggaggggcgcggtggggaaacggagcgaccgt     37860
gtctggaaaaagaaaagagcaggaagtatgcatacagatatgtgtgtatgtactgggct    37920
atggtgtgaaatcattcctgactgcgggttatagtcaaaacccatgaaaagcatcacta    37980
cagcccacgggtgtgtcagggacacagtgttgtgagccctgggaaggcagggcctgtggc    38040
cagcactttatcaacactggcgcatgcacctatgaggcaaagggatttgcattgtcccc    38100
ttacagtgtgggacactgaggtcgccaggggcgtggcgactgtaagggacagtgctggat    38160
gtgagcctcgcctgcaggaggcggtccaggaagcatgggtggaggggctggagaagtta    38220
gggccgcgtggcccgggaggctcccggaggagggaagggcctatctcagcgagggcata    38280
ggcggggaaggtgcgggcgaggcggccgcgggtccctggcatccctctccttacgccca    38340
ggctaagctggcggtgctgctggtgacgctggtggcggccgcggtctcctacctgcggat   38400
ggagcagaagctgcgccggggcgtggccccgcgccagccccgcatcccgcggccccagca   38460
caaggtgcgcggttaccgctacttggaggaggacaactcggacgagagcgacgcggaggg   38520
cgagcatggggacggcgcggaggaggaggcgccgcccgcagggcccaggcctggccccga   38580
gcccgctggactcggccgccggccctgcccgtacgaacaggcgcaggggggagacgggcc   38640
ggaggagcagtga
```

FIGURE 1L

| Polymorphic Region | Sequence | SEQ ID NO: |
| --- | --- | --- |
| 24801 sense 5' | ttgcactttctcatcat | 2 |
| 24801 antisense 5' | catcattacacag | 7 |
| 24801 A variant | catcatActgtgt | 12 |
| 24801 G variant | catcatGctgtgt | 13 |
| 24801 antisense T variant | acacagTatgatg | 22 |
| 24801 antisense C variant | acacagCatgatg | 23 |
| 24801 sense 3' | ctgtgtaatgatg | 32 |
| 24801 antisense 3' | atgatgagaaagtcaa | 37 |
| 24941 sense 5' | ccagccacccacc | 3 |
| 24941 antisense 5' | aggtggattcatgc | 8 |
| 24941 T variant | cccaccTgcatga | 14 |
| 24941 C variant | cccaccCgcatga | 15 |
| 24941 antisense A variant | tcatgcAggtggg | 24 |
| 24941 antisense G variant | tcatgcGggtggg | 25 |
| 24941 sense 3' | gcatgaatccacc | 33 |
| 24941 antisense 3' | ggtgggtggctgg | 38 |
| 27645 sense 5' | gctctcccccagat | 4 |
| 27645 antisense 5' | cctcagggctca | 9 |
| 27645 C variant | ccagatCtgagcc | 16 |
| 27645 G variant | ccagatGtgagcc | 17 |
| 27645 antisense G variant | ggctcaGatctgg | 26 |
| 27645 antisense C variant | ggctcaCatctgg | 27 |
| 27645 sense 3' | tgagccctggagg | 34 |
| 27645 antisense 3' | atctgggggagagc | 39 |
| 32163 sense 5' | actgagccttgggg | 5 |
| 32163 antisense 5' | ttcccaccctatt | 10 |
| 32163 A variant | ttggggAaatagg | 18 |
| 32163 C variant | ttggggCaatagg | 19 |
| 32163 antisense T variant | cctattTccccaa | 28 |
| 32163 antisense G variant | cctattGccccaa | 29 |
| 32163 sense 3' | aatagggtgggaa | 35 |
| 32163 antisense 3' | ccccaaggctcagt | 40 |
| 32614 sense 5' | ggtctggatcggatggc | 6 |
| 32614 antisense 5' | ccgacccaggcca | 11 |
| 32614 A variant | gatggcAtggcct | 20 |
| 32614 G variant | gatggcGtggcct | 21 |
| 32614 antisense T variant | aggccaTgccatc | 30 |
| 32614 antisense C variant | aggccaCgccatc | 31 |
| 32614 sense 3' | tggcctgggtcgg | 36 |
| 32614 antisense 3' | gccatccgatccagacc | 41 |

FIGURE 2

| Polymorphic Region | Primer Sequence | SEQ ID NO: |
|---|---|---|
| 24801 and 24941 | aatacaaaaatcagctgggtgta | 42 |
| 24801 and 24941 | gatgtggggaacagacaggt | 43 |
| 27645 | tggtgctgagggggtgtt | 44 |
| 27645 | gatttcctggagggcttagat | 45 |
| 32163 | gctctggtgggcaagacac | 46 |
| 32163 | cactggggctgggtgttc | 47 |
| 32614 | gatgggggcaggacagtc | 48 |
| 32614 | ttgtctccagctcgaaactgt | 49 |

FIGURE 3

REAGENTS AND METHODS FOR DETECTION OF HEART FAILURE

The present invention relates to oligonucleotides, kits, microarrays, and methods for detection of cardiovascular disease, in particular, left ventricular heart failure.

BACKGROUND OF THE INVENTION

The World Health Organization has determined that cardiovascular disease (CVD) is the leading cause of death throughout the world and the leading cause of lost years of healthy life in Europe. In the U.S., CVD caused 41 per cent of all deaths in 1998 and is second only to all cancers combined in years of potential life lost. The annual number of deaths from CVD in the U.S. increased substantially between 1900 and 1970, peaking in 1963. Since 1963 the U.S. CVD death rate has changed from an increasing to a decreasing trend, and by 1995 the CVD death rate was similar to that in 1936.

The only exception to the CVD mortality decline in the U.S. is congestive heart failure (CHF). CHF is often the end stage of cardiac disease, and half of the patients diagnosed with CMF die within five years. Sudden death is common among CHF patients, occurring six to nine times more frequently than in the general population. Between 1968 and 1998, the number of deaths from CHF in the U.S. increased from approximately 10,000 to almost 50,000. Approximately five million Americans are currently living with heart failure, and 550,000 new cases are diagnosed in the U.S. each year. CHF occurs slightly more frequently among men than among women, and is twice as common among African Americans compared to Caucasian Americans, with mortality also doubled for African Americans. The number of CHF cases is expected to increase as the population ages, and as cardiac patients are able to survive and live longer with their disease. CMF has therefore become a major medical problem in the U.S.

As a symptom of underlying heart disease, heart failure is closely associated with the major risk factors of CVD: smoking, high cholesterol, hypertension, diabetes, abnormal blood sugar levels, and obesity, with hypertension and diabetes being particularly important. CMF is about twice as common for persons with hypertension as compared with normotensive individuals, and the degree of risk for heart failure appears to be directly related to the severity of high blood pressure. Persons with diabetes have a two- to eight-fold greater risk for heart failure than those without diabetes, and women with diabetes have a greater risk of heart failure than men with diabetes. The presence of coronary disease is one of the greatest risks for heart failure. Muscle damage and scarring caused by heart attacks create a fivefold increase in risk of developing CHF.

Heart failure occurs when one or more of the chambers of the heart cannot keep pace with the amount of blood flowing through an individual's body. Heart failure can involve either or both sides of the heart, but in general, the left side of the heart is affected first. Each side of the heart comprises an atrium (the upper chamber) which receives blood into the heart and a ventricle (the lower chamber) which pumps blood to the body. The left ventricle supplies most of the heart's pumping power and is larger than other heart chambers, pumping oxygen-rich blood from the left atrium to the rest of the body. When the left ventricle loses its ability to contract, the heart is unable to pump with sufficient force to push enough blood into circulation. This condition is known as systolic failure. When the left ventricle loses its ability to relax, usually because of stiffness from thickening (hypertrophy), the heart cannot fill properly with blood during the resting period between each heartbeat. This condition is known as diastolic failure. In either condition, blood entering the left atrium from the lungs may back up or regurgitate, causing fluid to leak into the lungs (pulmonary edema), and blood flow throughout the body slows down, causing fluid to build up in tissues (edema). The presence of excess fluid due to heart failure is termed congestive heart failure.

The symptoms of heart failure include shortness of breath (dyspnea), fatigue, fluid accumulation, and persistent coughing that produces mucus or pink, blood-tinged sputum. Heart failure develops slowly, and the heart compensates as its pumping capacity decreases. For example, the heart may enlarge, or muscle fibers within the heart may hypertrophy to allow the heart to contract with more force and pump more blood. The heart also compensates for loss of pumping capacity by contracting more frequently to increase circulation. However, eventually the heart can no longer compensate and symptoms only appear when the condition has progressed in severity.

Physicians currently diagnose heart failure through physical examination, to detect the observable symptoms indicated above. Electrocardiography is performed to determine whether the patient's heartbeat is abnormal and to identify the cause of the heart failure. In particular, an electrocardiogram with Q-waves and poor R wave progression indicates a previous myocardial infarction, with probable left ventrical systolic dysfunction. An electrocardiogram indicating left ventricular hypertrophy may show an etiology related to hypertension, aortic stenosis, hypertrophic cardiomyopathy or dilated cardiomyopathy, and may indicate either systolic or diastolic left ventricular dysfunction. A chest x-ray may indicate pulmonary edema, pulmonary venous engorgement, or cardiac enlargement. However, heart failure from left ventricular dysfunction may be present even when a patient has a normal chest x-ray. Physicians also perform an ultrasonic examination of the heart to generate an echocardiogram, which allows measurement of systolic and diastolic ventricular contractile function, chamber size, and wall thickness. When Doppler ultrasound is used for echocardiography, valvular stenosis and regurgitation can be detected and quantified.

Lifestyle changes such as weight reduction; moderate exercise; limiting fluid intake, including alcohol intake; and cessation of smoking, are indicated for individuals with chronic CHF. Left ventricular systolic heart failure can be treated using lifestyle changes, angiotensin converting enzyme inhibitors, diuretics, and/or digoxin. The optimal treatment for left ventricular diastolic heart failure has not been determined. Since left ventricular diastolic heart failure is frequently associated with hypertension, antihypertensive therapy is frequently prescribed, and congestion is relieved with diuretics.

A need remains for detection of predisposition to heart failure in individuals who may have the condition but who do not exhibit symptoms, so that lifestyle changes can be initiated early in the progression of disease. In addition, it is important to determine predisposition to heart failure in individuals who have experienced myocardial infarction, so that appropriate treatment modalities may be initiated to limit the effects of heart failure in such individuals.

SUMMARY OF THE INVENTION

The present inventors have found that predisposition to left ventricular heart failure may be detected by analysis of certain polymorphisms in the nucleic acid set forth in SEQ ID NO:1. Specifically, the presence of an A nucleotide at position 24801 of SEQ ID NO:1 (the sense strand), or a T nucleotide at the corresponding position of the complement of SEQ ID NO:1, is indicative of a predisposition to left ventricular diastolic heart failure. Furthermore, the presence of a T nucleotide at position 24941 of SEQ ID NO:1, or an A at the corresponding position in the complement of SEQ ID NO:1, is also indicative of predisposition to left ventricular diastolic heart failure. In addition, the presence of an A nucleotide at position 32614 of SEQ ID NO:1 (the sense strand), or a T nucleotide at the corresponding position of the complement of SEQ ID NO:1, is indicative of a predisposition to left ventricular systolic heart failure in individuals who have experienced a myocardial infarction.

Moreover, individuals who possess the SEQ ID NO:1 haplotype characterized by a G nucleotide at position 24801 of SEQ ID NO:1; a C nucleotide at position 24941 of SEQ ID NO:1; a C nucleotide at position 27645 of SEQ ID NO:1; a C nucleotide at position 32163 of SEQ ID NO:1; and a G nucleotide at position 32614 of SEQ ID NO:1 are at lower risk of developing left ventricular diastolic heart failure.

The nucleic acid of SEQ ID NO:1 (nucleotides 1-38653 of GenBank Accession No. AC004923) is the genomic sequence of a gene of unknown function currently described as hUNC93B1 (Kashuba, et al., submitted for publication). The hUNC93B1 gene is located on chromosome 11q13, and the mRNA (GenBank Accession No. AJ271326, SEQ ID NO:50) is expressed at high levels in cardiac tissue (Id.). Without wishing to be bound by any theory, it is believed that the hUNC93B1 gene may encode a twelve transmembrane transporter protein.

In one embodiment, the invention provides a sequence determination oligonucleotide complementary to a polymorphic region within a nucleic acid having a sequence as set forth in SEQ ID NO:1, wherein the region corresponds to a polymorphic site selected from the group consisting of position 24801 of SEQ ID NO:1, position 24941 of SEQ ID NO:1, position 27645 of SEQ ID NO:1, position 32163 of SEQ ID NO:1, and position 32614 of SEQ ID NO:1.

In yet another embodiment, the invention provides a microarray comprising at least one oligonucleotide complementary to a polymorphic region in the nucleic acid set forth in SEQ ID NO:1, wherein the region corresponds to a polymorphic site selected from the group consisting of position 24801 of SEQ ID NO:1, position 24941 of SEQ ID NO:1, position 27645 of SEQ ID NO:1, position 32163 of SEQ ID NO:1, and position 32614 of SEQ ID NO:1.

In another embodiment, the invention provides the oligonucleotide primer pairs useful for amplification of a polymorphic region in the nucleic acid of SEQ ID NO:1 from a biological sample, wherein the region corresponds to a polymorphic site selected 10 from the group consisting of position 24801 of SEQ ID NO:1, position 24941 of SEQ ID NO:1, position 27645 of SEQ ID NO:1, position 32163 of SEQ ID NO:1, and position 32614 of SEQ ID NO:1.

In another embodiment, the invention provides a kit comprising at least one oligonucleotide primer pair complementary to a polymorphic region of the nucleic acid of SEQ ID NO:1, wherein the region corresponds to a polymorphic site selected from the group consisting of position 24801 of SEQ ID NO:1, position 24941 of SEQ ID NO:1, position 27645 of SEQ ID NO:1, position 32163 of SEQ ID NO:1, and position 32614 of SEQ ID NO:1.

The invention is also embodied in a method of diagnosing predisposition to left ventricular diastolic heart failure in a human, said method comprising the steps of obtaining a nucleic acid sample from the human; detecting the presence or absence of at least one allelic variant of a polymorphic region in a nucleic acid having a sequence as set forth in SEQ ID NO:1 in the sample, wherein the polymorphic region corresponds to the polymorphic site at position 24801 of SEQ ID NO:1.

The invention is also embodied in a method of diagnosing predisposition to left ventricular diastolic heart failure in a human, said method comprising the steps of obtaining a nucleic acid sample from the human; and detecting the presence or absence of at least one allelic variant of a polymorphic region in a nucleic acid having a sequence as set forth in SEQ ID NO:1 in the sample, wherein the polymorphic region corresponds to the polymorphic site at position 24941 of SEQ ID NO:1.

In another embodiment, the invention provides a method of diagnosing predisposition to left ventricular systolic heart failure in a human who has experienced a myocardial infarction, said method comprising the steps of obtaining a nucleic acid sample from the human; and detecting the presence or absence of at least one allelic variant of a polymorphic region in a nucleic acid having a sequence as set forth in SEQ ID NO:1 in the sample, wherein the polymorphic region corresponds to the polymorphic site at position 32614 of SEQ ID NO:1.

In a further embodiment, the invention provides a method of diagnosing predisposition to left ventricular diastolic heart failure in a human comprising the steps of obtaining a nucleic acid sample from the human; and detecting the presence or absence of a haplotype of the nucleic acid having a sequence as set forth in SEQ ID NO:1, said haplotype being characterized by: a G nucleotide at position 24801 of SEQ ID NO:1; a C nucleotide at position 24941 of SEQ ID NO:1; a C nucleotide at position 27645 of SEQ ID NO:1; a C nucleotide at position 32163 of SEQ ID NO:1; and a G nucleotide at position 32614 of SEQ ID NO:1.

BRIEF DESCRIPTION OF THE DRAWINGS

FIG. 1 sets forth the sequence of the nucleic acid of SEQ ID NO:1, with the polymorphic sites at positions 24801, 24941, 27645, 32163, and 32614 in bold capital type. The transcription start site of the nucleic acid of SEQ ID NO:1 is indicated in italics, introns are depicted in lower case type, and exons are depicted in bold lower case type.

FIG. 2 sets forth the sequences of certain oligonucleotides of the invention, which are correlated with the polymorphic site the oligonucleotides are designed to detect. Polymorphic sites in these oligonucleotides are indicated in bold capital type.

FIG. 3 sets forth the sequences of certain oligonucleotide primer pairs designed to amplify polymorphic regions of the nucleic acid of SEQ ID NO:1.

DETAILED DESCRIPTION OF THE INVENTION

The U.S. patents and publications referenced herein are hereby incorporated by reference.

Examples 1 through 3 below demonstrate associations between certain polymorphic regions in SEQ ID NO:1 and measurements of physical parameters of left ventricular heart failure. One such parameter, the echocardiographic ratio of peak velocities of the early (E) and a trial (A) contributions to left ventricular filling (the "E/A ratio") is a measurement of left ventricular diastolic function.

The present inventors have observed a correlation between E/A ratio and polymorphic variants at position 24801 of SEQ ID NO:1. Specifically, an A nucleotide at position 24801 of SEQ ID NO:1 is associated with lower E/A ratio (p=0.04836). Thus individuals who exhibit a homozygous A/A genotype at position 24801 of SEQ ID NO:1 have a higher risk of developing left ventricular diastolic heart failure, as compared to individuals who are heterozygous A/G or homozygous G/G at position 24801.

In addition, the present inventors have discovered a correlation between E/A ratio and polymorphic variants at position 24941 of SEQ ID NO:1, wherein the presence of a T nucleotide at that position is associated with lower E/A ratio (p=0.00170). Individuals who exhibit a homozygous T/T genotype at position 24941 of SEQ ID NO:1 have a higher risk of developing left ventricular diastolic heart failure, as compared to individuals who are heterozygous T/C or homozygous C/C at position 24941.

Moreover, the haplotype characterized by a G nucleotide at position 24801 of SEQ ID NO:1; a C nucleotide at position 24941 of SEQ ID NO:1; a C nucleotide at position 27645 of SEQ ID NO:1; a C nucleotide at position 32163 of SEQ ID NO:1; and a G nucleotide at position 32614 of SEQ ID NO:1 is associated with increased E/A ratio (p=0.00020). Individuals who are homozygous for this haplotype have significantly lower risk of developing left ventricular diastolic heart failure.

Another echocardiographic test for heart failure is the ejection fraction, which measures the amount of blood pumped out when the heart contracts, thus indicating left ventricular performance. Example 3 indicates that for those individuals who have suffered a myocardial infarction, an association exists between the polymorphic variant at position 32614 of SEQ ID NO:1 and ejection fraction (p=0.0365). Specifically, the presence of an A nucleotide at position 32614 of SEQ ID NO:1 is correlated with a low ejection fraction or risk of left ventricular heart failure.

The various embodiments of the present invention for the first time allow physicians to determine predisposition to left ventricular heart failure in a human using a simple diagnostic test performed on a biological sample from the individual. In accordance with the present invention, the sequence of one or more polymorphic regions of SEQ ID NO:1 is determined and risk of left ventricular heart failure is assessed. Using this information, physicians can intervene in the disease process of heart failure at a much earlier time than was previously possible, advising lifestyle changes or prescribing drug modalities which will reduce or delay progression of the disease. This early intervention will result in decreased morbidity and mortality from heart failure, ultimately impacting on economic sequence of the disease such as hospitalization expenses and lost years of healthy life.

For the purposes of the invention, certain terms are defined as follows. "Oligonucleotide" means a nucleic acid molecule preferably comprising from about 8 to about 50 covalently linked nucleotides. More preferably, an oligonucleotide of the invention comprises from about 8 to about 35 nucleotides. Most preferably, an oligonucleotide of the invention comprises from about 10 to about 25 nucleotides. In accordance with the invention, the nucleotides within an oligonucleotide may be analogs or derivatives of naturally occurring nucleotides, so long as oligonucleotides containing such analogs or derivatives retain the ability to hybridize specifically within the polymorphic region containing the targeted polymorphism. Analogs and derivatives of naturally occurring oligonucleotides within the scope of the present invention are exemplified in U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929,226; 5,977,296; 6,140,482; WO 00/56746; WO 01/14398, and the like. Methods for synthesizing oligonucleotides comprising such analogs or derivatives are disclosed, for example, in the patent publications cited above and in U.S. Pat. Nos. 5,614,622; 5,739,314; 5,955, 599; 5,962,674; 6,117,992; in WO 00/75372, and the like. The term "oligonucleotides" as defined herein includes compounds which comprise the specific oligonucleotides disclosed herein, covalently linked to a second moiety. The second moiety may be an additional nucleotide sequence, for example, a tail sequence such as a polyadenosine tail or an adaptor sequence, for example, the phage M13 universal tail sequence, and the like. Alternatively, the second moiety may be a non-nucleotidic moiety, for example, a moiety which facilitates linkage to a solid support or a label to facilitate detection of the oligonucleotide. Such labels include, without limitation, a radioactive label, a fluorescent label, a chemiluminescent label, a paramagnetic label, and the like. The second moiety may be attached to any position of the specific oligonucleotide, so long as the oligonucleotide retains its ability to hybridize to the polymorphic regions described herein.

A polymorphic region as defined herein is a portion of a genetic locus that is characterized by at least one polymorphic site. A genetic locus is a location on a chromosome which is associated with a gene, a physical feature, or a phenotypic trait. A polymorphic site is a position within a genetic locus at which at least two alternative sequences have been observed in a population. A polymorphic region as defined herein is said to "correspond to" a polymorphic site, that is, the region may be adjacent to the polymorphic site on the 5' side of the site or on the 3' side of the site, or alternatively may contain the polymorphic site. A polymorphic region includes both the sense and antisense strands of the nucleic acid comprising the polymorphic site, and may have a length of from about 100 to about 5000 base pairs. For example, a polymorphic region may be all or a portion of a regulatory region such as a promoter, 5' UTR, 3' UTR, an intron, an exon, or the like. A polymorphic or allelic variant is a genomic DNA, cDNA, mRNA or polypeptide having a nucleotide or amino acid sequence that comprises a polymorphism. A polymorphism is a sequence variation observed at a polymorphic site, including nucleotide substitutions (single nucleotide polymorphisms or SNPs), insertions, deletions, and microsatellites. Polymorphisms may or may not result in detectable differences in gene expression, protein structure, or protein function. Preferably, a polymorphic region of the present invention has a length of about 1000 base pairs. More preferably, a polymorphic region of the invention has a length of about 500 base pairs. Most preferably, a polymorphic region of the invention has a length of about 200 base pairs.

A haplotype as defined herein is a representation of the combination of polymorphic variants in a defined region within a genetic locus on one of the chromosomes in a chromosome pair. A genotype as used herein is a representation of the polymorphic variants present at a polymorphic site.

A polymorphic region of the present invention comprises a portion of SEQ ID NO:1 corresponding to at least one of the polymorphic sites identified above. That is, a polymorphic region of the invention may include a nucleotide sequence surrounding and/or including any of the polymorphic sites at positions 24801, 24941, 27645, 32163, and 32614 of SEQ ID NO:1. Polymorphic regions in the antisense nucleic acid complementary to SEQ ID NO:1 are also encompassed in the present invention, wherein the region includes a nucleotide sequence surrounding and/or including any of the antisense positions corresponding to positions 24801, 24941, 27645, 32163, and 32614 in the complement of SEQ ID NO:1. For example, a polymorphic region corresponding to the polymorphic site at position 24801 of SEQ ID NO:1 may comprise a sequence as set forth in any of SEQ ID NO:2; SEQ ID NO:7; SEQ ID NO:12; SEQ ID NO:13; SEQ ID NO:22; SEQ ID NO:23; SEQ ID NO:32; or SEQ ID NO:37. A polymorphic region corresponding to the polymorphic site at position 24941 of SEQ ID NO:1 may comprise a sequence as set forth in any of SEQ ID NO:3; SEQ ID NO:8; SEQ ID NO:14; SEQ ID NO:15; SEQ ID NO:24; SEQ ID NO:25; SEQ ID NO:33; or SEQ ID NO:38. A polymorphic region corresponding to the polymorphic site at position 27645 of SEQ ID NO:1 may comprise a sequence as set forth in any of SEQ ID NO:4; SEQ ID NO:9; SEQ ID NO:16; SEQ ID NO:17; SEQ ID NO:26; SEQ ID NO:27; SEQ ID NO:34; or SEQ ID NO:39. A polymorphic region corresponding to the polymorphic site at position 32163 of SEQ ID NO:1 may comprise a sequence as set forth in any of SEQ ID NO:5; SEQ ID NO:10; SEQ ID NO:18; SEQ ID NO:19; SEQ ID NO:28; SEQ ID NO:29; SEQ ID NO:35; or SEQ ID NO:40. A polymorphic region corresponding to the polymorphic site at position 32614 of SEQ ID NO:1 may comprise a sequence as set forth in any of SEQ ID NO:6; SEQ ID NO:11; SEQ ID NO:20; SEQ ID NO:21; SEQ ID NO:30; SEQ ID NO:31; SEQ ID NO:36; or SEQ ID NO:41.

In certain embodiments of the invention, oligonucleotides are used as probes for the polymorphic regions in the nucleic acid having the sequence set forth in SEQ ID NO:1. Such regions include the regions believed to be the putative promoter, that is, the region 5' to the transcription start site (nucleotide 26116 of SEQ ID NO:1), intron 3 (nucleotide 27179 to 30519 of SEQ ID NO:1), intron 6 (nucleotide 31842 to 32400 of SEQ ID NO:1), and intron 7 (nucleotide 32529 to 33414 of SEQ ID NO:1), as depicted in FIG. 1. These oligonucleotides may also be termed "sequence determination oligonucleotides" within the scope of the invention, and may be used to determine the presence or absence of a particular nucleotide at a particular polymorphic site within the nucleic acid of SEQ ID NO:1. Specific oligonucleotides of the invention include any oligonucleotide complementary to any of the polymorphic regions described above.

Those of ordinary skill will recognize that oligonucleotides complementary to the polymorphic regions described herein must be capable of hybridizing to the polymorphic regions under conditions of stringency such as those employed in primer extension-based sequence determination methods, restriction site analysis, nucleic acid amplification methods, ligase-based sequencing methods, methods based on enzymatic detection of mismatches, microarray-based sequence determination methods, and the like. The oligonucleotides of the invention may be synthesized using known methods and machines, such as the ABI™ 3900 High Throughput DNA Synthesizer and the Expedite™ 8909 Nucleic Acid Synthesizer, both of which are available from Applied Biosystems (Foster City, Calif.).

The oligonucleotides of the invention may be used, without limitation, as in situ hybridization probes or as components of diagnostic assays. Numerous oligonucleotide-based diagnostic assays are known. For example, primer extension-based nucleic acid sequence detection methods are disclosed in U.S. Pat. Nos. 4,656,127; 4,851,331; 5,679,524; 5,834,189; 5,876,934; 5,908,755; 5,912,118; 5,976,802; 5,981,186; 6,004,744; 6,013,431; 6,017,702; 6,046,005; 6,087,095; 6,210,891; WO 01/20039; and the like. Primer extension-based nucleic acid sequence detection methods using mass spectrometry are described in U.S. Pat. Nos. 5,547,835; 5,605,798; 5,691,141; 5,849,542; 5,869,242; 5,928,906; 6,043,031; 6,194,144, and the like. The oligonucleotides of the invention are also suitable for use in ligase-based sequence determination methods such as those disclosed in U.S. Pat. Nos. 5,679,524 and 5,952,174, WO 01/27326, and the like. The oligonucleotides of the invention may be used as probes in sequence determination methods based on mismatches, such as the methods described in U.S. Pat. Nos. 5,851,770; 5,958,692; 6,110,684; 6,183,958; and the like. In addition, the oligonucleotides of the invention may be used in hybridization-based diagnostic assays such as those described in U.S. Pat. Nos. 5,891,625; 6,013,499; and the like.

The oligonucleotides of the invention may also be used as components of a diagnostic microarray. Methods of making and using oligonucleotide microarrays suitable for diagnostic use are disclosed in U.S. Pat. Nos. 5,492,806; 5,525,464; 5,589,330; 5,695,940; 5,849,483; 6,018,041; 6,045,996; 6,136,541; 6,142,681; 6,156,501; 6,197,506; 6,223,127; 6,225,625; 6,229,911; 6,239,273; WO 00/52625; WO 01/25485; WO 01/29259; and the like. Preferably, the microarray of the invention comprises at least one oligonucleotide complementary to a polymorphic region of SEQ ID NO:1, wherein the region corresponds to a polymorphic site selected from the group consisting of position 24801 of SEQ ID NO:1, position 24941 of SEQ ID NO:1, and position 32614 of SEQ ID NO:1. More preferably, the microarray of the invention comprises an oligonucleotide complementary to a polymorphic region corresponding to position 24801 of SEQ ID NO:1, an oligonucleotide complementary to a polymorphic region corresponding to position 24941 of SEQ ID NO:1, and an oligonucleotide complementary to a polymorphic region corresponding to position 32614 of SEQ ID NO:1. Most preferably, the microarray of the invention comprises an oligonucleotide complementary to a polymorphic region corresponding to position 24801 of SEQ ID NO:1, an oligonucleotide complementary to a polymorphic region corresponding to position 24941 of SEQ ID NO:1, an oligonucleotide complementary to a polymorphic region corresponding to position 27645 of SEQ ID NO:1, an oligonucleotide complementary to a polymorphic region corresponding to position 32163 of SEQ ID NO:1, and an oligonucleotide complementary to a polymorphic region corresponding to position 32614 of SEQ ID NO:1. In a specific embodiment, the oligonucleotides of the microarray of the invention are complementary to any or all of the polymorphic regions selected from the group consisting of SEQ ID NO:2; SEQ ID NO:7; SEQ ID NO:12; SEQ ID NO:13; SEQ ID NO:22; SEQ ID NO:23; SEQ ID NO:32; and SEQ ID NO:37 (corresponding to the polymorphic site at position 24801 of SEQ ID NO:1); the polymorphic regions selected from the group consisting of SEQ ID NO:3; SEQ ID NO:8; SEQ ID NO:14; SEQ ID NO:15; SEQ ID NO:24; SEQ ID NO:25; SEQ ID NO:33; and SEQ ID NO:38 (corresponding to the polymorphic site at position 24941 of SEQ ID NO:1); the polymorphic regions selected from the group consisting of SEQ ID NO:4; SEQ ID NO:9; SEQ ID NO:16; SEQ ID NO:17; SEQ ID NO:26; SEQ ID NO:27; SEQ ID NO:34; and SEQ ID NO:39 (corresponding to the polymorphic site at position 27645 of SEQ ID NO:1); the polymorphic regions selected from the group consisting of SEQ ID NO:5; SEQ ID NO:10; SEQ ID NO:18; SEQ ID NO:19; SEQ ID NO:28; SEQ ID NO:29; SEQ ID NO:35; and SEQ ID NO:40 (corresponding to the polymorphic site at position 32163 of SEQ ID NO:1); and the polymorphic regions selected from the group consisting of SEQ ID NO:6; SEQ ID NO:11; SEQ ID NO:20; SEQ ID NO:21; SEQ ID NO:30, SEQ ID NO:31; SEQ ID NO:36; and SEQ ID NO:41 (corresponding to the polymorphic site at position 32614 of SEQ ID NO:1).

The invention is also embodied in oligonucleotide primer pairs suitable for use in the polymerase chain reaction (PCR) or in other nucleic acid amplification methods. Each oligonucleotide primer pair of the invention is complementary to a polymorphic region of the nucleic acid of SEQ ID NO:1. Thus an oligonucleotide primer pair of the invention is complementary to a polymorphic region characteristic of at least one of the polymorphic sites at positions 24801, 24941, 27645, 32163, and 32614 of SEQ ID NO:1. Those of ordinary skill will be able to design suitable oligonucleotide primer pairs using knowledge readily available in the art, in combination with the teachings herein. Specific oligonucleotide primer pairs of this embodiment include the oligonucleotide primer pairs set forth in SEQ ID NO:42 and SEQ ID NO:43, which are suitable for amplifying the polymorphic region corresponding to the polymorphic sites at positions 24801 and 24941 of SEQ ID NO:1; the oligonucleotide primer pairs set forth in SEQ ID NO:44 and SEQ ID NO:45, which are suitable for amplifying the polymorphic region corresponding to the polymorphic site at position 27645 of SEQ ID NO:1; the oligonucleotide primer pairs set forth in SEQ ID NO:46 and SEQ ID NO:47, which are suitable for amplifying the polymorphic region corresponding to the polymorphic site at position 32163 of SEQ ID NO:1; the oligonucleotide primer pairs set forth in SEQ ID NO:48 and SEQ ID NO:49, which are suitable for amplifying the polymorphic region corresponding to the polymorphic site at position 32614 of SEQ ID NO:1. Those of skill will recognize that other oligonucleotide primer pairs suitable for amplifying the polymorphic regions of the nucleic acid of SEQ ID NO:1 can be designed without undue experimentation. In particular, oligonucleotide primer pairs suitable for amplification of larger portions of SEQ ID NO:1 would be preferred for haplotype analysis.

Each of the PCR primer pairs of the invention may be used in any PCR method. For example, a PCR primer pair of the invention may be used in the methods disclosed in U.S. Pat. Nos. 4,683,195; 4,683,202, 4,965,188; 5,656,493; 5,998,143; 6,140,054; WO 01/27327; WO 01/27329; and the like. The PCR pairs of the invention may also be used in any of the commercially available machines that perform PCR, such as any of the GeneAmpo Systems available from Applied Biosystems.

The invention is also embodied in a kit comprising at least one oligonucleotide primer pair of the invention. Preferably, the kit of the invention comprises at least three oligonucleotide primer pairs, wherein each primer pair is complementary to a different polymorphic region of the nucleic acid of SEQ ID NO:1. More preferably, the kit of the invention comprises at least four oligonucleotide primer pairs suitable for amplification of polymorphic regions corresponding to positions 24801, 24941, 27645, 32163, and 32614 of SEQ ID NO:1. Most preferably, the kit of the invention comprises at least five oligonucleotide primer pairs suitable for amplification of polymorphic regions corresponding to positions 24801, 24941, 27645, 32163, and 32614 of SEQ ID NO:1. This embodiment may optionally further comprise a sequence determination oligonucleotide for detecting a polymorphic variant at any or all of the polymorphic sites corresponding to positions 24801, 24941, 27645, 32163, and 32614 in SEQ ID NO:1. The kit of the invention may also comprise a polymerizing agent, for example, a thermostable nucleic acid polymerase such as those disclosed in U.S. Pat. Nos. 4,889,818; 6,077,664, and the like. The kit of the invention may also comprise chain elongating nucleotides, such as dATP, dTTP, dGTP, dCTP, and dITP, including analogs of dATP, dTTP, dGTP, dCTP and dfIP, so long as such analogs are substrates for a thermostable nucleic acid polymerase and can be incorporated into a growing nucleic acid chain. The kit of the invention may also include chain terminating nucleotides such as ddATP, ddTTP, ddGTP, ddCTP, and the like. In a preferred embodiment, the kit of the invention comprises at least one oligonucleotide primer pair, a polymerizing agent, chain elongating nucleotides, at least one sequence determination oligonucleotide and at least one chain terminating nucleotide. The kit of the invention may optionally include buffers, vials, microtiter plates, and instructions for use.

Methods of diagnosing predisposition to left ventricular heart failure in a human are also encompassed by the present invention. In the methods of the invention, the presence or absence of at least one polymorphic variant of the nucleic acid of SEQ ID NO:1 is detected to determine or diagnose such a predisposition. Specifically, in a first step, a nucleic acid is isolated from biological sample obtained from the human. Any nucleic-acid containing biological sample from the human is an appropriate source of nucleic acid for use in the methods of the invention. For example, nucleic acid can be isolated from blood, saliva, sputum, urine, cell scrapings, biopsy tissue, and the like. In a second step, the nucleic acid is assayed for the presence or absence of at least one allelic variant of any or all of the polymorphic regions of the nucleic acid of SEQ ID NO:1 described above. Preferably, the polymorphic regions on both chromosomes in the chromosome pair of the human are assayed in the method of the invention, so that the zygosity of the individual for the particular polymorphic variant may be determined.

Any method may be used to assay the nucleic acid, that is, to determine the sequence of the polymorphic region, in this step of the invention. For example, any of the primer extension-based methods, ligase-based sequence determination methods, mismatch-based sequence determination methods, or microarray-based sequence determination methods described above may be used, in accordance with the present invention. Alternatively, such methods as restriction fragment length polymorphism (RFLP) detection, single strand conformation polymorphism detection (SSCP), PCR-based assays such as the Taqman® PCR System (Applied Biosystems) may be used.

In accordance with one method of the invention, predisposition to left ventricular diastolic heart failure is diagnosed by determining the identity of the nucleotide at position 24801 of SEQ ID NO:1. In this method, an A nucleotide at position 24801 of SEQ ID NO:1, or a T nucleotide at the corresponding position of the complement of SEQ ID NO:1, is indicative of greater risk of developing left ventricular diastolic heart failure. Conversely, the presence of a G nucleotide at position 24801 of SEQ ID NO:1, or of a C nucleotide at the corresponding position of the complement of SEQ ID NO:1, is indicative of a lower risk of developing left ventricular diastolic heart failure. In a further step, the zygosity of the individual may be determined, wherein a homozygous A/A genotype at position 24801 of SEQ ID NO:1 or T/T at the corresponding position of the complement of SEQ ID NO:1, indicates greatest risk for developing left ventricular diastolic heart failure. A person whose genotype is homozygous G/G at position 24801 of SEQ ID NO:1 or C/C at the corresponding position of the complement of SEQ ID NO:1 is at least risk for developing left ventricular diastolic heart failure. An individual whose genotype is heterozygous A/G at position 24801 of SEQ ID NO:1 or T/C at the corresponding position of the complement of SEQ ID NO:1 is at intermediate risk for developing left ventricular diastolic heart failure.

Alternatively, predisposition to left ventricular diastolic heart failure is diagnosed by determining the identity of the nucleotide at position 24941 of SEQ ID NO:1. In this method, a T nucleotide at position 24941, of SEQ ID NO:1, or an A nucleotide at the corresponding position of the complement of SEQ ID NO:1, is indicative of greater risk of developing left ventricular diastolic heart failure. Conversely, the presence of a C nucleotide at position 24941 of SEQ ID NO:1, or of a G nucleotide at the corresponding position of the complement of SEQ ID NO:1, is indicative of a lower risk of developing left ventricular diastolic heart failure. In a further step, the zygosity of the individual may be determined, wherein a homozygous T/T genotype at position 24941 of SEQ ID NO:1 or A/A at the corresponding position of the complement of SEQ ID NO:1, indicates greatest risk for developing left ventricular diastolic heart failure. A person whose genotype is homozygous C/C at position 24941 of SEQ ID NO:1 or G/G at the corresponding position of the complement of SEQ ID NO:1 is at least risk for developing left ventricular diastolic heart failure. An individual whose genotype is heterozygous T/C at position 24941 of SEQ ID NO:1 or A/G at the corresponding position of the complement of SEQ ID NO:1 is at intermediate risk for developing left ventricular diastolic heart failure.

In another method of the invention, risk of left ventricular heart failure is assessed by determining the haplotype of the individual for various polymorphic positions within SEQ ID NO:1. For example, individuals who possess the SEQ ID NO:1 haplotype characterized by a G nucleotide at position 24801 of SEQ ID NO:1; a C nucleotide at position 24941 of SEQ ID NO:1; a C nucleotide at position 27645 of SEQ ID NO:1; a C nucleotide at position 32163 of SEQ ID NO:1; and a G nucleotide at position 32614 of SEQ ID NO:1 are at lower risk of development of left ventricular diastolic heart failure. This haplotype may alternatively be detected on the antisense strand, or complement of SEQ ID NO:1 as a C nucleotide at the position corresponding to position 24801 of the complement of SEQ ID NO:1; a G nucleotide at the position corresponding to position 24941 of the complement of SEQ ID NO:1; a G nucleotide at the position corresponding to position 27645 of the complement of SEQ ID NO:1; a G nucleotide at the position corresponding to position 32163 of the complement of SEQ ID NO:1; and a C nucleotide at the position corresponding to position 32614 of the complement of SEQ ID NO:1. Individuals who are homozygous for allelic variants comprising this haplotype are at particularly low risk of developing left ventricular diastolic heart failure.

In yet another method of the invention, risk of left ventricular systolic heart failure in individuals having suffered a myocardial infarction is assessed by determining the identity of the nucleotide at position 32614 of SEQ ID NO:1. An A nucleotide at position 32614 of SEQ ID NO:1 or a T nucleotide at the corresponding position of the complement of SEQ ID NO:1, is indicative of greater risk of developing left ventricular systolic heart failure. Conversely, the presence of a G at position 32614 of SEQ ID NO:1, or a C at the corresponding position of the complement of SEQ ID NO:1, is indicative of a lower risk of developing left ventricular systolic heart failure. In a further step, the zygosity of the individual may be determined, wherein a homozygous A/A genotype at position 32614 of SEQ ID NO:1 or T/T at the corresponding position of the complement of SEQ ID NO:1, indicates greatest risk for developing left ventricular systolic heart failure. A person whose genotype is homozygous G/G at position 32614 of SEQ ID NO:1 or C/C at the corresponding position of the complement of SEQ ID NO:1 is at least risk for developing left ventricular systolic heart failure. An individual whose genotype is heterozygous A/G at position 32614 of SEQ ID NO:1 or T/C at the corresponding position of the complement of SEQ ID NO:1 is at intermediate risk for developing left ventricular systolic heart failure.

The examples set forth below are provided as illustration and are not intended to limit the scope and spirit of the invention as specifically embodied therein.

EXAMPLE 1

Study Population

During the Uppsala Longitudinal Study of Adult Men (ULSAM) re-examination 1990–94 (n=1221) (www.pubcare.uu.se/ULSAM), a sub-study including a comprehensive echocardiographic assessment of cardiac morphology, systolic and diastolic function in 583 individuals was performed (Andren B, Lind L, Hedenstiema G, Lithell H. (1998) Echocardiography 5:433–450, "Left ventricular diastolic function in a population sample of elderly men", hereinafter Andren et al.). In 475 subjects the technical quality of the assessment was sufficient to calculate all indicators of cardiac function and morphology. The ECGs of this subset were analysed thoroughly and systematically, and biochemical markers of subclinical heart failure were also analyzed. Of these 475, DNA samples were available from 395 subjects. The results set forth in the Examples are based on 330 of these individual, from whom informed consent for genetic analysis was obtained.

Andren et al. performed a comprehensive echocardiographic examination using a Hewlett-Packard Sonos 1500 cardiac ultrasound unit with a 2.5 MHz transducer. Left ventricular dimensions (interventricular septum thickness, posterior wall thickness, end diastolic diameter) were measured in 2D-guided M-mode using a leading edge to leading edge convention. Left ventricular volumes including ejection fraction (EF) were calculated with the Teichholz formula. Left ventricular mass was determined from M-mode measurements according to the American Society of Echocardiography. Measurements of left ventricular filling were used to estimate diastolic function. Peak velocities of the early (E) and a trial (A) contributions to LV filling were recorded, and the E/A ratio was calculated.

Office blood pressure was measured in the right arm with the subject in the supine position after resting for 10 minutes, and then after the subject had been standing for 2 minutes. The values were recorded twice and to the nearest even figure. The means of the two values are given for each blood pressure. The cuff size was 12.35 cm or 15.45 cm depending on the arm circumference. Systolic (SBP) and diastolic (DBP) blood pressures were defined as Korotkoff phases I and V, respectively.

The ambulatory blood pressure measuring device Accutracker II (Suntech Medical Instruments, Raleigh, N.C.) was attached to the subjects' non-dominant arm by a skilled laboratory technician. Systolic and diastolic blood pressures were measured every 30 minutes during daytime (0600–2300) and every hour during the night over a 24 hour period. After November 1993, the blood pressure was measured every 20 minutes during the whole 24-hour period.

Data were edited to a limited extent. All readings of zero, all heart rate readings <30, diastolic blood pressure readings >170 mm Hg, systolic blood pressure readings >270 and <80 mmHg, and all readings where the difference between systolic and diastolic blood pressure was less than 10 mm Hg were omitted. Mean arterial blood pressure (MAP) was calculated over the whole measurement period according to the formula MAP=2/3*DBP+1/3*SBP.

A standard 12-lead ECG was recorded at 50 mm/s and 10 mm/mV and evaluated according to the Minnesota code by one experienced physician who was unaware of the other data collected from the subjects.

EXAMPLE 2

Power Calculation and Statistical Basis of Phenotypes

A power calculation was performed in which the objective was to estimate the power to detect a SNP/endpoint association using DNA samples and clinical information from the study population of Example 1. The power was estimated as a function of realistic combinations of percent phenotype variation, explained by a quantitative trait locus (QTL), that is, a hidden causative SNP, and the degree of linkage disequilibrium (LD) between an assumed number of five SNPs and the QTL. Assumed genetic effects of 10–25% were considered, and a range of LD's between the selected genetic positions was used in the power calculation. The result indicated that, in the case of high LD, an effect of 13% phenotypic variation could be detected with 80% power. In the case of lower LD, the effect would have to be 25% or higher for the study to achieve 80% power. The use of haplotype information was not considered in the power calculation. Primary and secondary end point variables (phenotypes) were selected based on clinical relevance, coverage, and inter-correlations. The ejection fraction (representing systolic function), E/A ratio (diastolic function), left ventricular mass index and relative wall thickness (left ventricular geometry) and Qt-max (arrhythmia) where chosen as primary endpoints. Table 1 shows that these variables have high coverage in the study population, and Table 2, depicting the Pearson correlation coefficients between primary endpoints, shows that their inter-correlations are low, even if the within-subject variability is taken into account. The E/A ratio was adjusted for heart rate at the time of measurement in all analyses. Also, the assumed effects of a QTL for the assumptions of 10 and 25 percent explained variance are shown, converted to a mean difference between two genotypes for each endpoint.

TABLE 1

| Variable | n | mean | Std | $R^2 = 10\%$ (1.1*sd) | $R^2 = 25\%$ (1.9*sd) |
|---|---|---|---|---|---|
| Ejection fraction (EF) | 296 | 0.65 | 0.10 | 0.11 | 0.19 |
| E/A ratio (E_A) | 298 | 0.96 | 0.33 | 0.36 | 0.63 |
| Left ventricular mass index (LVMI) | 329 | 135 | 28 | 31 | 53 |
| Relative wall thickness (RWT) | 329 | 0.40 | 0.06 | 0.07 | 0.11 |

TABLE 1-continued

| Variable | n | mean | Std | $R^2 = 10\%$ (1.1*sd) | $R^2 = 25\%$ (1.9*sd) |
|---|---|---|---|---|---|
| Qt-max (QETMAX) | 293 | 42.2 | 3.4 | 3.7 | 6.5 |

TABLE 2

| | EF | E_A | LVMI | RWT |
|---|---|---|---|---|
| E_A | 0.04 | | | |
| LVMI | −0.16 (−0.22) | 0.05 | | |
| RWT | 0.24 (0.39) | −0.16 (−0.22) | −0.00 | |
| QETMAX | −0.05 | −0.15 | 0.20 (0.25) | 0.15 (−0.18) |

The following variables were selected as secondary endpoints: N-atrial natriuretic peptide (ANP) and AV-plane displacement (representing systolic function), isovolumetric relaxation time (IVRT) (diastolic function), Cornell and Sokolow-Lyon ECG criteria for left ventricular hypertrophy (left ventricular geometry) and QT-dispersion (arrhythmia). IVRT values were adjusted for heart rate as with E/A ratio.

EXAMPLE 3

Genetic Analysis

To identify polymorphic positions in the nucleic acid characterized by SEQ ID NO:1, twenty-two (22) fragments covering selected regions of the gene were amplified (GeneAmp™ PCR Systems 9700, Applied Biosystems) using genomic DNA from 15–30 unrelated anonymous individuals. The 3'-end of the gene was avoided, since that region is extremely homologous to other sequences in the human genome and there is risk of unspecific amplification. After amplification, detection of genetic variation in the nucleic acid of SEQ ID NO:1 was performed using solid phase sequencing (AutoLoad™ Solid-Phase Sequencing kit, Amersham Pharmacia Biotech) and gel electrophoresis on ALFexpress™ sequencers (Amersham Pharmacia Biotech).

Six SNP's were detected with a minor allele frequency of $\geq 10\%$ in the investigated individuals and five of these were included in the main study, see Table 3. Fragments covering each of the five SNP's were amplified from genomic DNA from the 330 individuals. SNP detection was subsequently performed using the PSQ 96 platform (Pyrosequencing AB, Uppsala, Sweden).

TABLE 3

| Genomic Location | Position in SEQ ID NO: 1 | Minor allele frequency in anonymous population | Minor allele frequency in the study population |
|---|---|---|---|
| Promoter | 24801 | 43% | 37% |
| Promoter | 24941 | 27% | 16% |
| Intron 3 | 27645 | 43% | 27% |
| Intron 6 | 32163 | 33% | 43% |
| Intron 7 | 32614 | 36% | 43% |

Genotyping was successful and only a few samples for each SNP failed, as shown in Table 4. Three samples failed to give result in all five polymorphic positions. In order to detect any genotyping anomalies, Hardy-Weinberg, haplotype analysis and duplicate control genotyping were performed. No deviation in genotyping result could be seen in the 100 duplicates checked. Hardy-Weinberg calculations were performed and the frequency of the three different genotypes for each SNP did not differ significantly from expected values.

TABLE 4

| SNP Position in SEQ ID NO: 1 | Percent approved genotypes | Number of approved genotypes | Number of failed genotypes |
|---|---|---|---|
| 24801 | 98.8 | 326 | 4 |
| 24941 | 98.2 | 324 | 6 |
| 27645 | 96.1 | 317 | 13 |
| 32163 | 98.2 | 324 | 6 |
| 32614 | 98.5 | 325 | 5 |
| All | 97.9 | 1616 | 34 |

Haplotype analysis could be performed on a total of 310 individuals. This analysis was performed using software based on maximum likelihood methodology and using the EM algorithm of Excoffier et al. (1995), *Mol Biol Evol.* 12:921–927. In total 8 likely haplotype were identified by the program. Two of these occurred only once in the study population and may not be true haplotypes but the result of incorrect genotyping in one of the polymorphic positions in the two individuals. The characterization and frequency of each haplotype is presented in Table 5. From the haplotype information two different kinds of variables were created: one variable was formed as a haplotype combination variable (HTYPE). This variable has the value H1/H2 when the subject has haplotypes 1 ans 2, etc. Variables H1, H2, H3 and H4 are haplotype annotations that denote the number of copies of that particular haplotype for the subject, e.g., for a subject with haplotype H1/H2 the variables H1, H2, H3 and H4 will be 1, 1, 0 and 0, respectively. Each of these variables can thus take on the values 0, 1 or 2. Only the four most frequent haplotypes were considered when those variables were formed. In all, ten genotype variables were considered (five SNP variables and five haplotype variables).

A discrepancy was noted between the protein encoded by SEQ ID NO:1, which was derived from GenBank Accession No. AC004923, and the protein encoded by the mRNA of Kashuba et al. (GenBank Accession No. AJ271326, SEQ ID NO:50). Specifically, in exon 7 SEQ ID NO:50 contains an insertion of a cytosine nucleotide at position 928, which is not present in the corresponding position in exon 7 of SEQ ID NO:1 (between positions 32505 and 32506). The mRNA of SEQ ID NO:50 is believed to be the correct sequence.

TABLE 5

| Haplotype | 24801 allele | 24941 allele | 27645 allele | 32163 allele | 32614 allele | Frequency |
|---|---|---|---|---|---|---|
| H1 | A | T | C | A | A | 57.3 |
| H2 | G | T | G | C | G | 20.9 |
| H3 | G | C | C | C | G | 15.0 |
| H4 | A | T | G | C | G | 5.7 |
| H5 | A | T | C | C | G | 0.46 |
| H6 | G | T | C | C | G | 0.35 |

Table 6 sets forth the results of the genetic analysis of the five SNPs and the five haplotype variables for the primary endpoints selected as phenotypes. It can readily be seen that the E/A ratio indicator of left ventricular diastolic function is strongly associated with the polymorphic variant at position 24801 of SEQ ID NO:1; the polymorphic variant at position 24941 of SEQ ID NO:1, and haplotype H3.

Table 7 sets forth the results of the genetic analysis of the five SNPs and the five haplotype variables for the secondary endpoint phenotypes. It can readily be seen that Cornell ECG indicator of left ventricular hypertrophy is strongly associated with the polymorphic variant at position 24801 of SEQ ID NO:1 and with haplotype H3. Table 7 also indicates an apparent association between the QT dispersion indicator of cardiac arrhythmia and haplotype H4.

TABLE 6

| Phenotype | position or haplotype | P-value |
|---|---|---|
| EF | 24801 | 0.21818 |
| EF | 24941 | 0.57041 |
| EF | 27645 | 0.66887 |
| EF | 32163 | 0.24830 |
| EF | 32614 | 0.19217 |
| EF | htype | 0.90939 |
| EF | h1 | 0.46524 |
| EF | h2 | 0.36469 |
| EF | h3 | 0.66847 |
| EF | h4 | 0.64227 |
| LVMI | 24801 | 0.94320 |
| LVMI | 24941 | 0.63141 |
| LVMI | 27645 | 0.46696 |
| LVMI | 32163 | 0.87578 |
| LVMI | 32614 | 0.87631 |
| LVMI | htype | 0.77012 |
| LVMI | h1 | 0.88680 |
| LVMI | h2 | 0.95998 |
| LVMI | h3 | 0.89396 |
| LVMI | h4 | 0.17517 |
| QETMAX | 24801 | 0.22153 |
| QETMAX | 24941 | 0.87435 |
| QETMAX | 27645 | 0.42356 |
| QETMAX | 32163 | 0.31261 |
| QETMAX | 32614 | 0.11870 |
| QETMAX | htype | 0.24619 |
| QETMAX | h1 | 0.19874 |
| QETMAX | h2 | 0.51169 |
| QETMAX | h3 | 0.96929 |
| QETMAX | h4 | 0.73154 |
| RWT | 24801 | 0.25784 |
| RWT | 24941 | 0.78161 |
| RWT | 27645 | 0.41252 |
| RWT | 32163 | 0.30551 |
| RWT | 32614 | 0.43261 |
| RWT | htype | 0.35828 |
| RWT | h1 | 0.31506 |
| RWT | h2 | 0.07013 |
| RWT | h3 | 0.62573 |
| RWT | h4 | 0.93931 |
| E_A | 24801 | 0.04836 |
| E_A | 24941 | 0.00170 |
| E_A | 27645 | 0.44418 |
| E_A | 32163 | 0.06127 |
| E_A | 32614 | 0.11287 |
| E_A | htype | 0.03685 |
| E_A | h1 | 0.07887 |
| E_A | h2 | 0.54734 |
| E_A | h3 | 0.00020 |
| E_A | h4 | 0.43201 |

TABLE 7

| Phenotype | position or haplotype | P-value |
|---|---|---|
| EKG_SOKO | 24801 | 0.82219 |
| EKG_SOKO | 24941 | 0.92077 |
| EKG_SOKO | 27645 | 0.99220 |
| EKG_SOKO | 32163 | 0.65859 |
| EKG_SOKO | 32614 | 0.88507 |
| EKG_SOKO | htype | 0.46097 |
| EKG_SOKO | h1 | 0.85415 |
| EKG_SOKO | h2 | 0.71702 |
| EKG_SOKO | h3 | 0.95304 |
| EKG_SOKO | h4 | 0.11765 |

TABLE 7-continued

| Phenotype | position or haplotype | P-value |
|---|---|---|
| IVRT | 24801 | 0.77690 |
| IVRT | 24941 | 0.39532 |
| IVRT | 27645 | 0.70896 |
| IVRT | 32163 | 0.43803 |
| IVRT | 32614 | 0.30175 |
| IVRT | htype | 0.82984 |
| IVRT | h1 | 0.44513 |
| IVRT | h2 | 0.94243 |
| IVRT | h3 | 0.51485 |
| IVRT | h4 | 0.62191 |
| lekgcorn | 24801 | 0.00109 |
| lekgcorn | 24941 | 0.51063 |
| lekgcorn | 27645 | 0.58615 |
| lekgcorn | 32163 | 0.11029 |
| lekgcorn | 32614 | 0.11740 |
| lekgcorn | htype | 0.01731 |
| lekgcorn | h1 | 0.17533 |
| lekgcorn | h2 | 0.11259 |
| lekgcorn | h3 | 0.56312 |
| lekgcorn | h4 | 0.72089 |
| lqtd | 24801 | 0.59641 |
| lqtd | 24941 | 0.95088 |
| lqtd | 27645 | 0.98059 |
| lqtd | 32163 | 0.93415 |
| lqtd | 32614 | 0.85672 |
| lqtd | htype | 0.07182 |
| lqtd | h1 | 0.78281 |
| lqtd | h2 | 0.26660 |
| lqtd | h3 | 0.99647 |
| lqtd | h4 | 0.00131 |
| N_ANP | 24801 | 0.64328 |
| N_ANP | 24941 | 0.86943 |
| N_ANP | 27645 | 0.93129 |
| N_ANP | 32163 | 0.85780 |
| N_ANP | 32614 | 0.92505 |
| N_ANP | htype | 0.96838 |
| N_ANP | h1 | 0.82067 |
| N_ANP | h2 | 0.84195 |
| N_ANP | h3 | 0.81062 |
| N_ANP | h4 | 0.56422 |

Table 8 indicates that for the E/A ratio a significant result (using the permutation test disclosed in Churchill, G. A. and Doerge, R. W. (1994) *Genetics* 138, 963–971) was achieved for the H3 haplotype variable (p=0.0002):

TABLE 8

| H3 | n | E/A ratio mean | std dev |
|---|---|---|---|
| 0 | 209 | 0.92 | 0.23 |
| 1 | 62 | 0.97 | 0.30 |
| 2 | 9 | 1.23 | 0.43 |

A group of subjects homozygous for H3 has thus approximately 34% increased level of E/A ratio compared to a group of non-carriers for this haplotype.

Table 9 indicates that a significant association was observed between ECG criteria according to Cornell and the polymorphic variant present at position 24801 of SEQ ID NO:1 (p=0.001):

TABLE 9

| 24801 | n | Cornell ECG mean | std dev |
|---|---|---|---|
| A/A | 123 | 14.85 | 6.20 |
| A/G | 142 | 14.20 | 5.51 |
| G/G | 42 | 19.24 | 9.19 |

Systolic function was also evaluated among different SEQ ID NO:1 genotypes in the 53 subjects who had suffered a myocardial infarction prior to the echocardiographic examination. The mean values of ejection fraction were significantly different for polymorphic variants at position 32614 of SEQ ID NO:1: A/A 0.56, A/G 0.62, and G/G 0.68 (p=0.0365). When "low ejection fraction" was defined as an EF value below 50%, the prevalence was 37% for individuals with the A/A genotype compared with 20% for A/G and 11% for G/G individuals (p=ns). These data therefore are consistent with a protective effect on post-myocardial infarction left ventricular performance by the G allele at position 32614 of SEQ ID NO:1.

While the invention has been described in terms of the specific embodiments set forth above, those of skill will recognize that the essential features of the invention may be varied without undue experimentation and that such variations are within the scope of the appended claims.

What is claimed is:

1. A method of diagnosing predisposition to left ventricular diastolic heart failure in a human, said method comprising the steps of:
   a) obtaining a nucleic acid sample from the human; and
   b) detecting the presence or absence of at least one allelic variant at position 24941 of SEQ ID NO:1 in the sample, whereby the presence or absence of the at least one allelic variant is indicative of a predisposition to left ventricular diastolic heart failure in the human.

2. The method of claim 1, further comprising the step of:
   c) determining the genotype of the human at position 24941 of SEQ ID NO:1.

* * * * *

SEQUENCE LISTING

```
<160> NUMBER OF SEQ ID NOS: 51

<210> SEQ ID NO 1
<211> LENGTH: 38653
<212> TYPE: DNA
<213> ORGANISM: homo sapiens
<220> FEATURE:
<221> NAME/KEY: 5'UTR
<222> LOCATION: (1)..(26156)
<223> OTHER INFORMATION:
<221> NAME/KEY: misc_feature
<222> LOCATION: (24801)..(24801)
<223> OTHER INFORMATION: nucleotide 24801 is a single nucleotide
      polymorphism which can be A or G
<221> NAME/KEY: misc_feature
<222> LOCATION: (24941)..(24941)
<223> OTHER INFORMATION: nucleotide 24941 is a single nucleotide
      polymorphism which can be T or C
<221> NAME/KEY: exon
<222> LOCATION: (26157)..(26252)
<223> OTHER INFORMATION:
<221> NAME/KEY: Intron
```

```
<222> LOCATION: (26253)..(26401)
<223> OTHER INFORMATION:
<221> NAME/KEY: exon
<222> LOCATION: (26402)..(26543)
<223> OTHER INFORMATION:
<221> NAME/KEY: Intron
<222> LOCATION: (26544)..(27024)
<223> OTHER INFORMATION:
<221> NAME/KEY: exon
<222> LOCATION: (27025)..(27178)
<223> OTHER INFORMATION:
<221> NAME/KEY: Intron
<222> LOCATION: (27179)..(30519)
<223> OTHER INFORMATION:
<221> NAME/KEY: misc_feature
<222> LOCATION: (27645)..(27645)
<223> OTHER INFORMATION: nucleotide 27645 is a single nucleotide
      polymorphism which can be C or G
<221> NAME/KEY: exon
<222> LOCATION: (30520)..(30681)
<223> OTHER INFORMATION:
<221> NAME/KEY: Intron
<222> LOCATION: (30682)..(30894)
<223> OTHER INFORMATION:
<221> NAME/KEY: exon
<222> LOCATION: (30895)..(31027)
<223> OTHER INFORMATION:
<221> NAME/KEY: Intron
<222> LOCATION: (31028)..(31747)
<223> OTHER INFORMATION:
<221> NAME/KEY: exon
<222> LOCATION: (31748)..(31841)
<223> OTHER INFORMATION:
<221> NAME/KEY: Intron
<222> LOCATION: (31842)..(32400)
<223> OTHER INFORMATION:
<221> NAME/KEY: misc_feature
<222> LOCATION: (32163)..(32163)
<223> OTHER INFORMATION: nucleotide 32163 is a single nucleotide
      polymorphism which can be A or C
<221> NAME/KEY: exon
<222> LOCATION: (32401)..(32528)
<223> OTHER INFORMATION:
<221> NAME/KEY: Intron
<222> LOCATION: (32529)..(33414)
<223> OTHER INFORMATION:
<221> NAME/KEY: misc_feature
<222> LOCATION: (32614)..(32614)
<223> OTHER INFORMATION: nucleotide 32614 is a single nucleotide
      polymorphism which can be A or G
<221> NAME/KEY: exon
<222> LOCATION: (33415)..(33597)
<223> OTHER INFORMATION:
<221> NAME/KEY: Intron
<222> LOCATION: (33598)..(34314)
<223> OTHER INFORMATION:
<221> NAME/KEY: exon
<222> LOCATION: (34315)..(34588)
<223> OTHER INFORMATION:
<221> NAME/KEY: Intron
<222> LOCATION: (34589)..(36404)
<223> OTHER INFORMATION:
<221> NAME/KEY: exon
<222> LOCATION: (36405)..(36523)
<223> OTHER INFORMATION:
<221> NAME/KEY: Intron
<222> LOCATION: (36524)..(38341)
<223> OTHER INFORMATION:
<221> NAME/KEY: exon
<222> LOCATION: (38342)..(38653)
<223> OTHER INFORMATION:
<300> PUBLICATION INFORMATION:
<308> DATABASE ACCESSION NUMBER: Genbank/AC004923
<309> DATABASE ENTRY DATE: 1999-12-21
<313> RELEVANT RESIDUES: (1)..(38653)

<400> SEQUENCE: 1
gatccacctg atctgtatga ctcccgtact caaccagcct atgtttccta ccagcgaatt      60
```

-continued

```
tttttttttt tttttttttt tttctttttt tgagacaatc tggctctgtg gctcaggctg      120
gaatgcagtg gtgcgatctc ggctcactgc agcctcgacc tcccaggctc gggtgatcct      180
cacttctcag cctcccgagc agctggaacc acagtcgcct gccaccacca ggctcggcta      240 attttttgtat tttttgtaga dacgggtct cgccatgttg cccaggctgg tctggaactc      300
ctggactcag gcgatcctcc tgcctcggcc tgccaaagtg ctgggattac aggcgtgagc      360
caccacgccg ggccttccc cgggaatgct gtggtagagg gacccgcaga ggccccgagg      420
ctgcctgcat gtgtgtgttg ggaggatctg cgctgagggt aggtaggagt tgggcaggcc      480
aggacaggaa ggaggcagag ggcatgtccc atgcccgtgc agagggagga cacgcatggt      540
agaccaggac gaggacaagg gcaggctcag tgtgtgcaaa ggggacagtg gtttgggatt      600
tgcatgcaga tgcccgagcc tccaaaggac ctgtgggcca cagggagacc ctgggggagt      660
tcaagctgag gagtggagag ggctttgggc tggtcagcag gtgctcagag gagagggct      720 ggccctagag agaagggagg tcttgggatg gtggcccaca cctgaccctg gcccttcatc      780
aggtgattcc tgcgtggatg cctgcgggga ttcctgcgtg gattgggaa gtcctgcagc      840 attacagaat tgttacccaa cgccagggcc ttggtccaga gtcctgttgc tagatgcaca      900
gaaagcaaat cactgagatg taagtattgc cagggaagaa ggctttattc aggtgacatc      960
agccagagag acaggagacg aaactcaggt ccaccctgt ccctcttccc gactaaagtt     1020
gtaggttgat atagtctaaa aagaaagcag gagccaagga agaggaggtg gcccgcaggc     1080
cgcaggagca gcctctcatt gtccaaatgt aggtttctca agcatccggc ttgttaggaa     1140
attgggccag tttcagaatc atcagcttgt caaaagtgg gacttgggag gtgagaaggg     1200
ttgtcaggca ggaaaccctg cattctgctt tggctgagtg gatgggccc aggaggatga     1260 gcagcatggg gaagagtatg actcgtagtg ggcaccatga ggataaagag ttacaagctc     1320
ctctggcatg ggctggaggg aagggagacc ctatcgcata accacagccc cacctgcctg     1380 gagagaaagag ggaggcggcc ccgctccgtg ccaccccact gagaaagata ggacacctgg     1440
agctccagct cagcaatccc tcaatccctc aatccttcat ttcatccttg caacagtccc     1500
aggaggtttt tttttttttt tttttttaagg cagagcctcc ttctgtcacc caggccggag     1560
ttcagtgacg caatctcagc tcacggcaac ctccacctcc cgggttcaag cgattctcct     1620
gccttagcct cctgagtagc tgggattaca ggcatgcgcc accacgccag ctaattttt     1680 gtatttttag tagagacggg gtttcgccat gttagccagg ctgatcttga actcctgatt     1740
tcaggtgatc cgcctgcctc ggcctcccaa agtgctggga ttacaggtgt gagccgcctc     1800
acccagccag gaggtatcaa tggttaattc tctccactga acaaatggaa aaactgagac     1860
tcagagaggg caggaatggc cttggatgca gtgattccat ggtgtggcct gagtcagatg     1920
ccagggcccc tcggacgccc gctccacagg agaggggtga ctcagaggtg ccgtgtctgt     1980
cctcttctcc tgaatatggg tggttggtgc ggggcaggg ggtgagtcac tgcactgttt     2040
cccatgcctc ccacctcggc tctcatggtt gggagcggct gagggaggag gctgaggcag     2100
ggagagggaa gacccaggag ggaggaggca ggcgctgctt tgagggtgc cctggagcct     2160 tggcaatcct tttcctcctc gggcccggga gcccaggccc cgtctccacc agccgcaggc     2220
gacagctgtc atggtggtct acagcctggg cctggggaag ggctcagagc agtgtgcagc     2280
tgcagccttg gcctccatgg ccaccagcag catcctcagg cggcgcggcg attgcggcgg     2340
gtagcggagg gcgttgagct tctccatccc cgggctgcgc aggaggcagg cgcgatggtg     2400
```

-continued

```
ggagaaggtg tcgaaggaga acttgccatg gtaccggccc atcccactgg cacctgtaca    2460
gtggcacaga acacaggtgg tcaggcgctg gggtctcct agtcacagac agtggggcct     2520
aggcgggcta cttctcccct ctgagcctca gtttccccat ctgtccagtg ggctgatcat    2580
gaggcactgt gtgtaaaggg cttggccccg agcttggcac cagctcagta agccctgggg    2640
atgccagatg ccagggcaag ataggcgggt ggtggtcaag ggcatggatt ccagagtcag    2700
actgccgggg gttaaactct ggccctgctg caaacaatcc atgtcacctt ggactgtgcc    2760
tcagtctcct ctgtcgtggg gtgacaaggg tacctccctc ctaaggttgt ggtgggatt     2820 gagggatgt tgagacccct ggacccagta ggtgctatgt gcagtgaact ctcctcagcg     2880
tctaggttgg gaggcagacg aggcccccagg ccagggcgtt cagagcacag cctgggtgga   2940
gtggggttgg ctgggggct tcctgcagtg agtgagctcc aaggatatgc agttaataag     3000
acgaagagag tgggtggggg caagagggac ccaggcttgg ggagccttag aggtgggtgc    3060
catgcggtgt gttagggacc tgggcagagc tcaggctgtg ggagcagcag gtgggaagc    3120 cggggtgggg ccacggccac caagaagggt cagctcgggg gcctgggagc tgggggaggc    3180
tttcttgagg gagcagcagg gtcagatgtg cccacagaca gccccgactc tcctccaggg   3240
cagggaggcg ggttgaggag gctggggctg gggctgggga ggcagctagg tggggtcggg   3300
ggcagccgcc caaactcgag ccgagccagg acagcagcac aggcactgtt gtgcccctgg   3360
ctgccctcca ggaagggcat ggacccacct gaggcagctt gcctggccct gccatcgttc    3420
actgtggtgc tgagtgtgga caggtggcgg gactgcctgt cacctgctcg ggccctactg    3480
ttctctgagg aggaagtggg ctcagaaagg ggagatgtca cctgggccac agggccttca    3540
gcgtgttgct aggaccatct ctgaggcttc ctgactcaga ggccaggact ctgcagtggc    3600
atcggggctg ctctgggggg tgaggattg gcactcatcc gggcctctca gggtggggag    3660
gtgttgtact gagagctgga gggggatgg ggttagagga gcagctgccc tggagtaaag    3720
gacaccggcg gcattgctgc tgaggggcag acaccaggtc atgctgttgg ggagaagagc    3780
aaatagcatc gcagtgggca gtgtgatcat agttgtgtgg tatttttaaa aattcactaa    3840
attgtgtgtc tgtgcagaga tggtctagaa ggttccacca cagactttt tttgagatgg     3900 ggtcttactg tgttgcccag attggactca gaccctctgg ggtggggagc aggatgcggg    3960
ttctggggtg aggcctcctt gcctgtccct ctacattgag gtggggctgg ggtgctttgg    4020
cagaaatgta tgcaggtaac actattgcaa tttgaccaaa tggtaacaga agggcagggt    4080
agcaggcacc tacccactcc tccaaaaggc aggctggcca gggtcatgtg catgaagccg    4140
tcgttcccac agaagccccc gctgctggtc tgggtcagca cccgcttgac cacctgggag    4200
agaacaggat gtgcgtgagg ctgccttgag ccccatcagg atcctcagga cccagagcct    4260
gttccatgct ggactctgtg acactgatct tgcctcagaa agggtctgag gccaccatgt    4320
cagctgaagg gcctgtgatg gtacaggtgg ggcaggggggt tgtgtagcag ctcctcatga   4380
agcttccaac ttgggacatg tttcctggac atctgctcat gtgtggtcca tgctgatggc    4440
acagactctt agggctgggg gtaggggcag gaaacctagt gttgcttggg gacatggagg    4500
gtgtagtggc agcagggcag tactggacag taggaggca tcccaggaga ggggtgtcat     4560
gtgcctgctg agtggaggga ctgggaggga cagaagttgt tcaggcaaag agggcactgc    4620
agacagagtg gaggctgaag agctgtgtgg tgtgaacaca gggacatgaa acataatga     4680 tgtggtcaga tttgcacttt agaaacagaa gcttggccct tgcttgaagg tccttgagaa    4740
ggaccttctt cctcaatctg tagacttatt tgaagactga aaggaaaaaa agattggtag    4800
```

-continued

```
acactaaata gttgctgcac aaaaacttca gtatatttag ttgcaatcac cgtgaacctc   4860
tgatcacagc tgggtcaggg cttgtctgat gtggggaaag cggactgccc ccagtggatt   4920
cagacgtcac ttcatggcat gagaccagca ttacccacaa tggcagtggc agcagatgga   4980
ggagatggag cagaaggcag cagagggcgt cccaggtagt acgggcaagc caccttgtgc   5040
atgacttgtg tcttaggtgt gactgtgtgt cctgggatca gttctggtgt gtcagaaaag   5100
tttgaagcca gatgactcca ctgtcaaaaa acctctgtag agttttctaa aggtgaaagt   5160
atccagatga agcagggctc cttgaaggaa tggctgcttc tggagttgga gcaggggaga   5220
tacaagatga gcctggagct gcttgtagca ccagagggga aggaggtggt cacaacccaa   5280
gaggctggga catcttacat gggcttctga gcccgagcct cagacaaacc acgaccctt    5340
ggattacagc ccctggagtc aaataaatat acctgagtcc gtagtgacct aaataaacaa   5400
ttcaagagat gaatctttct tacagaattc caggaaatga atgtagatac tgctgttagc   5460
caagaatacg gtatccagct aagactatgc ttcgtagatg aagaaataaa gcctttccca   5520
gacaagcaaa ggctggggga atttatcact actagatcag tcctgcaaga aatgctcaaa   5580
ggagtcttaa cataaaaaca agttggtatt tgccataata cacacaaaag tacaaaactc   5640
acaggcccta taaacaatc atacaaagga ggaagagaaa ggtatcaaat ggcaatacaa    5700
caaaattcca ccaaaccaca aatggaataa gaaagaatg tataaaataa ctagataata    5760
actaacaata tgatagagca gcatacagct taattacctc cacctggtga gggtggggta   5820
ggcttagaga cttgcttcca aataataaag aaacaaacaa tagtagcttc ccagggaaac   5880
cctggcagat accgtcctga cccggtagtg aaggttccac tcactagcca cgtgtgcatc   5940
tcaggtgccc cagatgtggt gtgagaggca ggctcacctc tgtgggattc tctcctaaaa   6000
ccagtaacct ttctttaatc atgagaaata caccagatga cctgaggctg gggatgttct   6060
acaggagacc tgtccagcac tccttaagct gagagggtta ttaatgcaag gtgggaccct   6120
ggcttggatc ctggggccga agaggatgt cagtggaaaa acagcaaaat ccaaataaag    6180
tctagagtgt agttaatagt aaagcactgc tgtcactttt tttttttttt tatgggtcag   6240
gagatccttc cacctcagcc tcccgagcag ctggcattac aggtgtgcgc cactatgcgc   6300
aactaatctt aaaaaaatgt ttcatagaga cggggttttg ctatattgcc agcgctggtc   6360
tcaaactcat gagctcaagc aatcctccca ccttggcctc ccaaagtgct gagattacag   6420
gtgtgagcca ccgcgcccag ccctgccatc acttttttag ttttgaccca tctaagcacc   6480
attaaatggg ggaaattagg tgtggggtac atgggaactc tctgtaccat tttggcaact   6540
tttctgtaaa tctaaaagta tttcccaata caaagtttat ttaaaaaaag ttcaagtggc   6600
cgggcacggt ggctcatccc tgtaatccca gcactttggg aggccgaggc aggtggatca   6660
cctgaggtca gcagttcaag actagcctga ccaatgtggc aaaacccat ctctactaaa    6720
aatacaaaga attagccggg catagtggca cacgcctgta atcccagcta cacaggaggt   6780
tgaggcagga gaatcgcttg aacccgggag gcagaggttg cagtgagcca agactgtgct   6840
actgcactcc agcctgggtg acagagtgag actctgtctc aaaaaaaaaa aaaaaaagt    6900
tcaagtggag ggaatcgagg aactggctga gggccgggga aggggcggg gtgggtaggg    6960
actgctggta cctcttggtg ttttttaatc tgaggactct ggccttgggc ctcccaggct   7020
gcctctgcag cttaagcagg gtaggggat cagggctcat tcttggacct gcacctttgg    7080
gtcatccccg acacgttgcc tgtgccttca gagccaggct tgagggtca tgtggccacc    7140
```

```
aggccccgat gtgtaagaag gacaaaggca ggggctgacc tagaggaaac actggaccct   7200
agagaaggcc catacccag gaagctgccc actgaaggcc taggagagtg gggcccagac    7260
tggggacagg gttggggtgg gtgaggctca gctgcttcca ggagagtggg cagagacaga   7320
gccaagaggt ccaccatccc aaagtcctga agccactgga ttttggtgcc cccctgctg    7380
ccaccacttg tgctgcccac tgcgggctcc tgaccctgcc cagcccggcc gcaccccac    7440
ctggctgctg ttggagaagg cgtacagggc caggggcttc tcccgccggt tgatgaactc   7500
gatggcctcg tccaagctct gcacgttcac gatgggcagg atgggcccga agatctcctc   7560
ctgcatcaca ggctccatct cctgcacatc caccagcacc gtggggctg caggcaccag   7620
agacagctca gccctggggc cacagtcagg accgccccca gggtgggggt agaggtgggg   7680
acagggccac aggccagggc tctaggccag gatcccaagg tctgacttcc caaggcttca   7740
ggctttggag tgtttaggga agaaagtctc cccacagccc cccagaaggg actctagagc   7800
ttccccagcc tgctcagggc ctgtgggaca cagagaatcc cccgaccttg gtctcacagt   7860
cagggtgat gggatcttag aacccttgga gttcatgagg caacagcgtc ccagaatgtt   7920
ggcgccgcag tgtcccatga gctgctgagc cgtacggccc aggagactgg gggctcagga   7980
cgggactctc ggagtttaga acctggggat tgtgggctcg gagaatctga ggttacagcc   8040
tttcaggata gccagtggtg ggatgggagt tcatcttagc acgctgagcc ctggagccct   8100
gggatctgag ctcagcgaat ccaaggtgag ggaccagagt ttggcctcat agggccacag   8160
acttagaagc acagagacgg aatcatggca ctggagctgt ggctcaaggc cgggctctgg   8220
cagtggggcc aggtttcagg cgcgggtcca gagttgtggc ccagccttgg gccctccagt   8280
gaggaggggt cttggcccag gtgggctgtg gtaggggcag caggactcac cgatgtagcg   8340
atcgctctca tcgctctggc ccccaatggc cacacgccgc agcccagcaa tgcccgcagc   8400
cgctggaact gtttctggtt gatgatgcgg cccaggtttg gggagctctg ggggtcgtcg   8460
ccatagaaac gggtgatggt gctctgcagg gcaggcagca gcctctcctg catctcaggg   8520
ctgcatagga cgtagtcggg ggccacgcag gtctggccgg cgttgaagta gcggaaccag   8580
gccacgcggt tggccacggt ctggggggtcg cagttgtcgt ccacgtagca agggttcttg   8640
cccccagct ccagggtgac aggtgtcagg tgcttggcgg cagcagtcat aacaatcttg    8700
cccacacgag ggctccctgg gcatggaagg aaaccagagt ggccgttcag tgacctggac   8760
caggcgggat ggcccagccc acggccccgc tcctccctgg agaggtggtg gagtcagcgg   8820
gcagcagccc tcgcctggcc tttccttgtt cctcactgcc accctgcagc ccagggccct   8880
gctcatcctt catcaggacc agcccctaag cacagagtct caggagggaa tggtgcacgg   8940
ctgctatcgg ccccagggt cccctgctg agccaaaccc cttggctcct cccgcctctg     9000
cttgtgaccc tggctgaccc tgcaggggac tctttgcaaa atgctgcatg gaaccctcc    9060
ccacccatct cctttggaaa cttcggggat cccttatcac ccaaggatgg agtccagctc   9120
tgtctacggc attcaggtct ctcttctcta aacctaaacc tggaagttct gccacctgcc   9180
cagcccttt tttctgaccc ttgaggtgga ctgtcccagg ctgatgcagg cgtccccatg    9240
tcctgcctgg cttggcctca cctctcctct gtgctggcct ccaggggccc agcagtctcc   9300
gcatgcacac agccttctct gccctagccc tgtctgggcc tcaaggcctc ctctccagac   9360
ctgactcggg gaccacgctg ctgcgtctgt ggggatggcc ctggcatttc tccccttgt    9420
ggtcaaggat taaagccggc aggagccact gtgccttctc tactctcacc cctgccccat   9480
cctggcacag tgcttcctgg gctctgtggt tccttccagg gctcctttgc ctttgctggg   9540
```

-continued

```
aggcggccag gtcaatcctg ccaggccctt ccccacgact gcctcgacct gtaaggcgca   9600
gactcgcctg ccagcaccac tgtcttcctc tcgctccctc tgcccctccc tagctcaaaa   9660
actcgaagcc gggtgtggtg gctcatgcct gtgatcctg cactttagga gaccaaggca    9720
ggaggactgg ttgaggccaa gagttcgaga ccagcctgag caacagagtg agaccctgtc   9780
tttactaaaa atacaaaaaa ttagccgggc gtggtggtac atgcctgtca ccccagctac   9840
ttgggaagct gaggcatgag catcacttga acccaggagg cgcagaggtt gcagtgagcc   9900
aagattgtgc caagattgtg ccactgcctg ggtgacagag caagactctg tctcaaaaaa   9960
aaagaaaaaa aaagtgacct ctggcgtgga tttctccaag ggcttgtgtg cacattccag  10020
cctgtcccca tcctggccag cagggtgacc ctgggcagga cactgaggcc cagtccctca  10080
tctgcctgca gagagggctg tgggcaccag tagggtggtg tctaagagcc tggggggcag  10140
cagggtcacg tatgagggtc tggggacagt ggggcagag gctatggttc ctgacgctgt   10200
ggttggcaca gtgggctggc cctggacatg ggactccatc ccttcctaag gggtcctggg  10260
ggtccaggac tgctcccagc ctggtccaga gagagagaga gaggagaatt cagtctccct  10320
gtggactccc agagttaggg acaggacccc tgagcagctg tcctccccga ccccagcctg  10380
tcccgaccct cgtcccggcc tcacctgtga agaagatgta gtcgaacctg tgctctagca  10440
gctgccccgt ctcctggggc ccgcccagca ccacagcaaa gcagctctgc aaggcgggat  10500
gggtgaggct ccttctggga ccccagctcc gagaacacaa gggagcagcc cgccctgcct  10560
ggaccctgcc ctgcctccac cccgcctggc ctgacccagc cagggctcta ggagggttgg  10620
gtggaggcaa agtggggaga agggagctcc ccaaggttgg ctggcattgg caggcccagc  10680
ttggagtcca gctggcgctg gagggctga tgccagggcc aggtggaggc agacacggaa   10740
cccctgggca acaggctgcc ctcgctgctc ctcagaggga aactgaggct gacaggggcg  10800
gtgacttggt caagtttaca caactcagaa gaggcaggat tgaggtgggg actcgggtct  10860
gactgacagg cccttccatg ccaggggctg cccagccctt gagccttgcc tgttcccgct  10920
ctacctgccc ggcagccctg ctcacctggt ccacgtattg gggcagcacc tcggccagga  10980
tcttctcgac gttcttgcta atctccgatg gcttcagcac cacacagttc cctgcagggc  11040
agtgcaggga gagagctgga ggaggcgtag ccagctcctg gtctccacac acctgcaggg  11100
caggcatcag cctcacccac tttcagatgc agaacctggt tcagagaggt aacatgacgg  11160
gcccagggcc acacagcccg gggacggtgg accagacagt cctctttgcc acctgggcca  11220
gttctcccat gtcctcctgg gatccatggg tggccctgag gcctcgagcg gagaagggtg  11280
accgaagggg gcaggcccag ctctcacctg cagcgagggc tccacgagg gcaccagcg    11340 tcaggttcag cggatagttc cagggcgcaa tgatgaggac caggccaaag ggctccttcc  11400
ggatgaaggc ggagtccagc tgcgtggcct gggccggag ccgggatga aattaagtgc    11460 tcagcacccc ggcccctcag cagccagctc ccacccagag gggccaccct gtgggagcaa  11520
atatcccctg agcccctgc ccgcctcagc ccggccggct caccaggttc ttgggcacac   11580
gctcgtcctt catccaggcc cggagttcct gagggccagg gtgacctcgc cctggctgat  11640
ggcaacctca gacacctccg actcgaaggc tgactgcagg aagtgggtgg ggtcagggtg  11700
ggccaggatt cccagagttg gcaggagggc acagcctcct ccaggcaggg cctgcttcca  11760
caactcattc attcattttc attcattcgt tcactcactc actccatgtt cagtgcgtgc  11820
ttcctgtgtg aggtgctgtc tctgtgccaa acagagggac cggccctgag gccgaccttg  11880
```

-continued

```
caggggcag tcgttccatg tgaaagtgag aacgctgacg gctccattag gacgtggctg      11940
tgctagggaa atcatggagc agggtggggg tggagactgc tggagcgtgt ggctgtgggc      12000
gtgcacaggt gtgcacatgt atacatccac atgagcatgt gtgtgtgtgc tgttttttaca    12060 aagcggtcag tgcaggtctc caggcggcgg tcacattgga gcagtgacct gaagtcaagg     12120
aacaagcaag tcgtgggtac tgggaggcgg catactttgg gcagaggccc tggcggctgc     12180
aaaggccccg aggtggctgt gcgcttgctc tgctcctgtt tagcaagaag cagagtgggc     12240
aaggtgaggg ggccaggcag ccaggcaagg actcctgaga agagcaggga tgggatctga     12300
cttagggttt tgtttttttt taatttcaaa aaagtttgt tttgattttt tgcagagtgc      12360
cttgctgtgt tgcctaggta ggtcttgaac tcctggcctc aaacaatcct cccacctcag     12420
tctcccaaag agcagggtgg agattggtcc acaggagaca caggcacagc caccctagg      12480 taaatgctgt cagttcccac agcccagggg ccagggccac tgtcaggctt ctaagcagga    12540
gtgaggagac ccgaatcaat agggacattg tcctgctctc ggctagccag tgctccctgc    12600
cctctgcgcc ccaagggagg agagaccagc caggcagcag gctgcaggcc gctgagaac     12660 aggtcaggga cactggggcc aggctggctc cctggctgag gcagcgcctg aggttatggg    12720
gtgcaggctc tcccgggtca gggcagaggg ggacgggcca gtggggtgct ggatgggcca    12780
gaggaccagc gaagcccaga gaaggagatg ccctgcctga ggtcactcag cgaaccaggg    12840
gcaaggccag ggctacagct gagccccaag agggaggaag acgccacgcc cactggcacc    12900
tcctagccac tgaggctggg ggaaggtgcc ttccacacgg actttcccac agcctgtgct   12960
ctggccccat gagcctggtg gcctgcccgc cacacctcct aggtcacctg ggacctgact    13020 tgggagact gggctatttt gagccaggtt caaactctgg ctctgctctt cctggctgca    13080
tgcccttggg caagaacaca ctctctctga gcctcttctg ggggccactg ggtgtggttg    13140
cccaaccaga ttcaccaaag ggttaactga gagggtgcac gtgacgctgg gcagatgctg    13200
cctgctgagg gtggggacag gggggtgacc aggtccagag ggagggacca ggttgaatgt    13260
tctgggctac tgctgccttt gtaggccccc gctcctgcag ctgggatggg aaggcaggag    13320
gtggaatcag agccgaaggg agaaaaggga ccagacagac gtcaggtcaa gtctcatgaa   13380
ggccggcagg cggccggtgg cagaagctca gtggtggcgg gggagtcagt ccccaggag    13440 cccaatgggc tggggaagg tctgaacact acagccttca aggcaaaggg aggagatatt    13500
ttgtccagaa ataggagcc gggggcagcc cctggggcag atgtgctgag gcaggggcag    13560
gtggtgtcct gaggcagggg caggtgtcct gaggcagggg caggcaggtg catgggccct    13620
gatgggtgag gggttggggg aagtgtgttt cttgggttc tgccttggct gccactggga    13680
ttgggagggg ctgaggcccc aagccttcag ggtctagaca gaggccatga tgcctgctgt    13740
acccagagag aaggccaagg cctcacggcc tccgaggccc tacatagtgt ggcccatacc    13800
ccagacctca tctttgctgt ttcttcctct cccaccccg acagctatgc tggcctcctt    13860
gctgctcctc aagcagaaac acccagcacc tcctgcctca gggcctttgc acgtgctgtg    13920
cccgctgcca tctccccagc atccatgggg agcctcccct ccatcttcac gtctctgctc    13980
taaagccccc ttctcagaga aaccttccct gaccccaca tatacaacag caccctgatc    14040 ctggcccct ctctcccctt caccctgggt gtgtctccag ggcacatatt tcaacccaat    14100
atgctgtgta attattatct ttattattat ttttgagatg gagtctcact gtgttgccca    14160
agctggagtg cagtggtgtg accttggctc actgcaacct ccacctccca ggttcaagcg    14220
attctcatgc ctcagcctcc tgagtagctg ggattacagg tgcccaccac cacatccagc    14280
```

-continued

```
taatttttgt attgttagta gagacgggt ttcgccatgt tggccaggat ggtcttgaac   14340
tcctggcctc aagcgatccg cccacctcgg cctcccaaag tgctgggact acaggtgtga   14400
gccaccatgc ccggccttgc tgtgcaatta tttatttgct gttttattgt ctccgataga   14460
aggtcatctt cgtaggcatg ggaactgtgt tttattctct gctatatccc cagagcctag   14520
aacagtacct ggcacatagt aggtgctcag caaatagttg ctgcatgaat acagaaataa   14580
gtgactggat gaatgtgcaa gggtggctct ggcctagggg aggagctgct tttagccccg   14640
cttcatggag ggcgcaggtg tcttcatccc ctgctgtccc agctgccctc catgccccc   14700 tgccccagtg caccctctca tacccccaac cccagcccac cttgtgcagg tcctgggcca   14760
gtgcgtcgtg cagaagctgc ttgttttctt gcaggaagcg gcccaggcct ggagctgcg   14820 cagcccggaa ctcagctggc cgcgtgcgcc ccgcgtggaa ggcctcccgc agtcgccgca   14880
gcgtgtcccc aaggggtcc atcctgccag atggggtggc atgaactggg tggccagggc   14940
tgcccctcct tcatgggcac cacccagccg ccccagggtc tgggcacccc tgacctgcct   15000
gcacccacag gggcttgcag acacctctac cttatacaca cagggacc cactcagatg   15060 accccacagg gactgaggct gcctgcaacc cctttcaccc aacagtgagc actcccagac   15120
acacatgaag accctcgcac cactcccctc tgccatggac ctggaggcgg ctgcaggact   15180
gggtgtgggc ttggggacag ctgctccacc acagccccg agggtgagca ggcaggcaga   15240
gcgccatgct tcttcctgcc gcacagaaat taaccccaag ccatggcctc tgccctgccc   15300
tgatgcccct cctggaggcg gggcagcctc accctgcca gtctgaatgg tgtaagcagg   15360
agcttgatga gtagagggg tgactcactg ccaccatggc caccaccttg gagcactcca   15420
gacacagaat tctccgtctt cctctgtccc cagcctgggg gcactgccca gggaggccag   15480
gccagtgggc aatagcctct tctccctgtg cctcagcttc ctcaggaaga ggggagaac   15540 acctcgggcc tcctggaggc cctgctgccc acctgccgg ggctgtggtg ctgggaggca   15600
gaaacagctg tgggggagag gatcaggcg ggggagaggg cgttcctgcc tccgtgctgg   15660
tgccagccag agctggcagg cagggtaggg gcctagacat tcccccgagc cctgcctgtt   15720
tacttgaagt tcatcggagg agcactctga cgcactcgtt cctcggcctg gtgccaagga   15780
cccgtggtga ccctttcctc cttccctctc cgagtcccctt tcctccagat ctcagcttgg   15840
ctgatgcttc ctccaggcag cccacccaga ttatgccctc atccactgtc acagtggccc   15900
cttgactctg ctccccagcg ttctgagttg tgccatgtga taaatgtctg gttacactct   15960
acccacctcc caaccctgtc cacatctccc ttatttcccc ctcattagac tgggaggcag   16020 gccctctgt gcctacttat ttgagaccta gtgcttgaag cctctcatgt taccggtgta   16080
atgatggcac ctgccagcta atgatgagac cacacagtcg gttctgagcc cagggcccag   16140
catcggtgag cgcaaggctg tgggtgattg ttaagtggcc accttgaggg cgggacctgc   16200
tccggtctgc aggatggccc tgctggacca gtgtgctact gagagcctgg tcaggagccc   16260
caggccagcc ctcagctgga gtgattgtgg ggccaggctg aacccaccat cttcctgctc   16320
tgattgggag aagctgggca gtggcccgca cacaggacag gcaccatggt ccccataggg   16380
gatggctcgt cacgggagca ggactgagac ccaggagcca agaacgagcc tctcgagcca   16440
ccatcaggcc tgtctccggg ctctgcctct tactggttgt gggaccttgg gcaaatcact   16500
caccttctct gcctcggttt cctcatctgt gaaatgggga tgctaatggc acctggtgtc   16560
attgtgagga ttaaatgaca tcacgctgca taaaacattt gctgttgtgc ccacagaaag   16620
```

-continued

```
tactcgacaa aggtcagctc tgggtgtttt gctaagtagc ctgcaaatat ttatctccct   16680
caactccgca ctctcctggg tccttctcca ttctactctc accttcagac ttctgccagt   16740
ggtcaaaggc aaaccacgcc tgtgcctctc tcacccttg taagaatctc tgcagaaacc    16800
acaaaaatgc aaggcacgta acgtgaatgg tggactgtgg gccgggagct ctgtggggga   16860
tggagttctg cagggaacat tccagcaacc ctcctagcaa cgctgaaacc aactcaccag   16920
ggccacagga cacatctctc ccacagggca accagccctg gcattgcccc tacgggtcac   16980
tcactctgga ctgaggcccc cagggagtgc ccagggcagg accctggcaa gcggagaagc   17040
caaggccgcc ttctgcctga gattgggggg atcctgggcc tgttatctcc cgagggtgct   17100
gggcagccat tgtggacaca cagaataggg aactcctgaa tcaggcactg gctgggggtc   17160
ccccaagccc accccgcgg cactcatccc acagtgtgag gttgtaagga gtgtgatccc     17220
catgcctgcc ctcgctcatt tcaccaccac ggccgcccac tgaggaccca ctattcaccc   17280
cactgaagga gatggaggct gaggctcaga gagggccaga gcttgcctga taccacccag   17340
ctcctcacat tggaaaaccc aaatccagaa gagcagaagg ctatccacct cagctcccac   17400
ctccctcaca gtcccctggg gatgggcagc caagtccttg ggggaaggga cactgggctg   17460
gggcctggac ggcagaccca aggctgggtg gactccggta ggccagctgt gggaggggtg   17520
accggtgagg ggaggtctct tgctgttgg attccatttc ctcggcctcc ctcctcacta   17580
ttgctgccac tccccacact gcttaggttg tggggtctga gactgcctct tgcctcctgc   17640
ggctgagcca ctgaggtcca ggggctgatg ggcccaaggg tctctgggc gtggcccccc     17700
atcacaggtt gaggtgcatt tggcccagac ctgcagcttc tggggtgggg gggagttgcc   17760
acatcatttg gtgatgaaga tagcggctgt ttcctctggc ctgggggcca gggcaggacc   17820
agccacttcc tctcaaggcc acgggcctct aaaaacaata ctcaggtgcc catgtgctgg   17880
gcactatgcc agcctgggtg ctcgctgtgg gtgcccacag gctccgggaa cagagtgggg   17940
aggaacgggg ctgacatatc acagggagtg aatggctggc cgagccgctg ccccccaacct  18000
cacagcaggg accgtccctg gcagggact ccctgctcgt tcacccctg gcctatcaag     18060
tgggttggat tccagggaaa cggaggctct gcccgttctc tcattcttcc tgcctcagtt   18120
tcctcatcta caccatggc cttctaagag catcctccca gcatggcatg gtctgggggc     18180
ccaatgacct gggtttaaac tgcagcaacc acatgtgtga gtggggagac cttgggcagg   18240
ttgcttgacc tctttgtatt cacgtttccc atctgtaaaa ttgggcactg cctgtggcac   18300
ccataccact gtcgggagaa ttcaagcact gggaccccgg gaagtgctca gtatccatgg   18360
aggacggatg taccagagga gggctcaggg aggagacccc tggggcaggg gcctgaaggg   18420
gccttgatcc aaggtgggtg ttggggagac aaggacatca ccctgagacc caactgagga   18480
cagggatgtg gtgacagagg gactgaacat ggtgggtaga gggcctgggg gaccccccatc   18540
agggcagcca gaaggcgggg atcactaggc caacttcagg ggacccacag gcccaatacc   18600
gcagggtctc cgattctgat ctcctgcagt gtagcttcat taaacaaaca tgatgagagg   18660
ctgtgatttt gaactgagct cctgtactag gccccaacag accagaccaa accaaaatgg   18720
aggcactcat gccaaatgcc acatcatcaa accgaagctt taaggaagca gacagagccc   18780
aaaaccacag accagtttct ccgggaagca ggagattcca gtccacctga gccggcatca   18840
tcaggtcccc tctgccttac cccttagaaa aaagcagtcc gcttagaaaa aagcagtctg   18900
cagcgatccg gtattaggcg gtttggtgtt tcctatttt ctgtttcctc ctttctgcct    18960
tatgaacccc ctgctctgcc actgcctggt gggagctctc actccatttt gtagaatgga   19020
```

```
ggctgtccgg attcacgaat catgaataga agccaatttg atctataact aaatgtgttg   19080
tcattttgtc ttttgatggc cttaagctgg attttcatga ggcctcccaa agctcagcag   19140
cccctccctt ggggagccag ggaccagcgt atccctcat  tggtggctcg ggccaaccca   19200
gccccgggtc acaaagaggc tgaacagcct cggctccctg atgggcaca  gttcccggga   19260 tgagaagtgc ctcctgcagg cggggcgggg ctggctggcc actcctttct tggaccctga   19320
caaagtccat tgctaagaat gattcttttcc cagagtcatt catggccaca tccctgcatc   19380
agcactggga atgcaggctg gtgcccagga acggctgtt  gctggaaggg atacttgacc   19440
cctgtgggga aggggcgcac agtccttcct ggggcagctg acccagagc  tgttcccttg   19500 gttcccttgg agggtgtccg ggaatcccag gaaaaggagg cggtggcaac ccagctcgga   19560
caacggaagg gtgcctgctg ccagggggg  tgcccgggac ctcgctgcca ctccccagat   19620
ctgcctctcc tccttccgct ttctccccca gcaggcaggc agatgagctc agccaggaca   19680
cagtggcctc tgagtgcagc tgccggtggc taggcccgcc tgggctgcct gtaacccgga   19740
gttgctgagc tggactctgg cccgactgct ggcccactac agcccccagcc tccccgggat   19800 actctacctg aggctctgcc aagctgccct tcctcctggc tgtcccgctc tgcctggtgg   19860
ccctgctgtt aagaaatgtc caacgcaggg ccagtccccg ggggaggggt ggggcggagt   19920
tgccctagcc tcgtgcctga ctctggctct gggcgggctg gaggctgcaa gccaagattt   19980
caccaccgcc tccctcgggg gcctcgacat ctcctcccag accacagaga agaagtcaac   20040
gcccagaggg cgccaggcta gagccacaca gcagggctga gctccgagct gaggggcagc   20100
ctgaggagga ggaggagagg ctgtgcagca gggctgagca ctgagctgag gccagcctg    20160 aggaggagga gtggggcagt gggccctggg aatcccggtg tggggtgggg aactattatt   20220
gtattaatta tattctatta taatattatg tggaatgtta tggcccagaa tagcaaggaa   20280
gtctcgaccc cccactccca gccttccctc aatgcctccc ctaaggaata agaccactac   20340
tactcctgct gccctcctcc taccaccttg cctggtttac aagacaggag gaaagagaga   20400
aggcaaaaag ttagaaaaaa acagaagtaa gagaaatagc cagaagacct tggcgccacc   20460 acctggcccct ggtagttaaa aaaaagtgat aataatatca accccctgacc taaactactt   20520 gtgttatctg taaattccag acattgtatg agaaagcact gcaaaacttt ctgttctgtt   20580
agctgacgca tgcagccccc ggtcacgttc cccgagcttg ctcgatttat cacgacccct   20640
tcacgtggac cccttaaagt tgtaagcctt taaaaaggcc aagaatgtct ttttcaggga   20700
gctcggctct tgacgcaagt ctgctgatgc tcccagctga ataaacctct tccttcttta   20760
atccagtgtc tgaggtgttt tgtctgtggc ttgtcttgct acaccctacc caagactcag   20820
tttccccttc tgcaaaacaa agaggtcaga cccaaaggtg gctggagtct agaaatacca   20880
tcttagggac atacctcat  gcctgctcct ctcccagcgc cctgtgcttc cgtgttcctc   20940
cacaccaccc catgggccgc cccattcata gagcctgtct ttctgcagat ctaacatttt   21000
acaaacgagg aagtggggc  agagaggggg tgggatgtga acatggggcg tgtgtgtggc   21060
agagcttctt gctccagagc tgggctgca  cccgtttcgg atgtccctc  tgcctcccag   21120 gaggagtgcc tgcctctctg cttaggaccg tggtcatgat gccacgtgtc gccttggtgg   21180
ttcctgtagt cccgatcttc ctcaagttcg gcacaggcag ctgtgcctaa gcctgtccct   21240
gcctgccccc agcccgcccc ggatacacct gtcagagcca gcgtgctgtg gggatgatgt   21300
gcaagctgct gtgggtgtgg acaggcaggg gacagggtga caggtgtgga ggaagagcct   21360
```

```
cctctatgcc ccttcctggg cctgccgctg ctaccatctc cctggtgccc tgggcctccg   21420
tagctcccgg ccccggggcc tctgggccaa cgtggcacct gggaggtgct catcatggcc   21480
ccccccaccc gccagctccc tgcctacctg ggagggcggt gaggtcttct ggaccatgcc   21540
cacaccggtg gcccgtgatt agatagttag ggtgggggtg aaggactgca gagcccctgt   21600
cctctgtgtg ggatggagcc cccagccact gccagtcacg tggctcagca tgtgacagcc   21660
cagccctgcc attctctgga gctcagccag attgagcggg tgccaggcag ggctgggcag   21720
gggctgagcc tgtaggtctc agctgggagt gaggcccaga gagggcagcc actggtctaa   21780
ggccacacag caaatcaggg acccatcttg gcgggtactg gcaggtggga ggggtgtttc   21840
aggatcccga gggtcccctc cctggccagg gagctgttga agaatttccc ccaactcaca   21900
ggggccgaac ttgtcatgaa tgcaggagca acctgggagg aggcccccga agaggcctgt   21960
cctcccggga cagaactcct agccttccct gggagtgagg ctcccccaa gggaggccac    22020 acacctccca ggagggctgg gccctcccca ctctgggttg ggtgcccctc actactcctc   22080
aaagctccag aggctcagta gggcctggga gtcccatctt tgttgaggag cccagggtaa   22140
atggggagcc ctctgggtag ggcaccagga ggactcactt ttggagccag ctctggggtg   22200
aggtctgcca aggcccaggc cagccagggg gagtgggtgg agggggttgct cagggctccg   22260 ggccagacag ctgcggcccc gcctgccctg cctcctcctt gctgggctga cgcttcgcct   22320 cttttgggcct cagtgttccc atgtgagaat ggggctgact acagtcccgg gggcatctgt   22380
gggtgaatga gaggggttcgg caggcatgga tctcagcacc tggcatggag ggcgttaagt   22440
gtgaggtctg ggctcaaatc ctggtcctgt cacttacctg tgtgacctag gttagtgtct   22500
taaccccccg tgcctctgcc ttcccatctg taaaatggga cataagtgat tgtgaggctg   22560
aaacaagtta ttccatgcac gtgggcccgg aactgtgacc attccaagtg cccggccccc   22620
tctggaaggg tctgagagct accttccaga ctctaggaca ggagtgtggg cagggcatga   22680
gcatggcatc aggtggaatc attcatccat tcataattca ttcattcatt ccctcacttc   22740
tcagaaacac gcccctgagc ctggctcaca gggcctcaga cctgcccaag agcatctcac   22800
tgcctcatct gcccacgagt gaccttgaaa agaaacgtcc cctcactggg cctcagtttc   22860
cccagctgta aaatgggggc tgactctgcc tgcctcacat ggctactgcg agggtgaaac   22920
gagagccgac ctgaaggcac cgacagggca cctggttctc agtaggcgct cagagcatgt   22980
gaatgtcctc ctgcccctct ccttgccctc ctgaggaagt ggctgcccca ggccttggcc   23040
ctgaggccct ggccctgcct cccaccccct ccctggcagt cttgaaggct ggacccaccc   23100
tggctccttg aagaggcaaa gttagaggct gtaggggccc agggcccagg acacagtcag   23160
aactcacggg caacggtgaa tgcgggtcac ttgttcattt acgcactcaa caaacccttta  23220 ctgagcacct actgtgtgca gacacttcac acaattttca caattcccag acattattga   23280
ccatgctttc cagctgggcc acacagtgac aaggactcat ggggatccac aaccagcctg   23340
gcctggctcc ccgccccacg gtgcttccaa ggtgcctgga gccctcgcac aggaatgggc   23400
tggagtcttc agctctgggt gagcccttg ccaccaactc tcaggagcct caagtctcag    23460
tggaaagcag cagccacctg ggcatttgct gtgccaggca ctgggcagag cctttggcac   23520
accccaacct ggggacctcc caccatcctg tgagccagac tcagtgatca tcatccccat   23580
tggctttaat gtttaaaata ttgtggaatc acatccatgc cagggaagtg gtgtgaaggg   23640
aatcacgtgg gctgccagc acgctcctgt gtcagtgcaa tgcggggcaa caatattcca    23700
agaggttgtt tcagggagtt ccagttgaga gcaatattta ttctcttctg cttgcttttc   23760
```

-continued

```
tgcaaggaac atcgattatt ttcataatga gaactgaaag taaaggctta ttatagagaa    23820
aagcattggc aaacagtgag cacgggggga tctggccacc ccttcctggg gatgtgactg    23880
tgcactgttg caacctggat gggttggtgg aggtgctggc cctgctcaga tctctgtccc    23940
gcaggtcacc ctggtgtgtt tatctgggcc accctatcag cctcttagat agtctccagg    24000
ctccccaaga gcagctccat aaaccaccta aaaaaaaaaa tcctttctgg agagaggagg    24060
tgtatcagtc agggtttagt gcctccaggg ctgttttttg ttttttttgt ttttgtttg    24120 tttgtttgtt tgagaggtct cactctgtca cccacgctgg aatgcagtgg cacaatctca    24180
gctcactgca gcctcatcct cctgggctca gcaattctc ccacctcagc ctcctgagta    24240 gctgggcta caggtgtcca ccatcacacc aggctagttt ttgtattttt tgtagagatg    24300
ggttgggggg ggggtttgt ctcactttgt tgaggctggt cttgaactcc tgagctcaag    24360
tgatcctcct tggccagcca aagtgctggg attgcaggcg tgagccacag cgcccgaccc    24420
tctccaggtg ttttgagtag gagacattga gtgcagggaa ttggtggtac agcacaggtg    24480
atggaagagc ccaggatggg caaccatagc aaccgccaca accccaggc ccagaggaac    24540 aaggggagga agagattgca ccaggcccca gaagtttggg gtccctcagg gaaattgaga    24600
agctcggggg gcccactccc agcactttgg gggctaaggc gggtacatca cttgaggtca    24660
ggagttcgag accagcctgg gccaatatgg tgaaacccca tctctactaa aaatacaaaa    24720
atcagctggg tgtaggggca cacgcctgta attccagcta ctcacaaggc tgagtcagga    24780
gaattgcact ttctcatcat nctgtgtaat gatgctggtg tctgccatct gagaacggcc    24840
cccgccatag ccatactctc ccacctcctc cctgccctg cgcctcgggc cctgccctct    24900
cttcggctcc tttcctgtct cccacttcca gccacccacc ngcatgaatc cacctgtctg    24960
ttccccacat ctgcacttgg gcatcgtcac ctggagaaag ttctacctcc tggaagcctg    25020
aagccactgc agattcacgc ctccccccac cttcccagca atccttgcgg ggtgggaggt    25080
gtttgtcatc cagtcactca tgcacccatc cagtcacaag tattgatcac tcagtaggtg    25140
cccaatgcca tcctctgcat ttgggagagg atgtacctaa agagcagtgg gtggagggggg    25200 gtgcacaggg agggcatgga aaaccagaag ggaagtgaag ggactgcatt ctctgcaggg    25260
atggtctctt gttctgagag ctgagtggga aggaagccac ctgggaggcg cagcaggaag    25320
agcattcaaa ccagaaggaa cccaggggag agaatctgga tattttcaaa agtggccccg    25380
tggctccagc caggtcggtg gtagccagtg cttggagtg tcggcccac cacaggctcc    25440 cgctgcagcc cggatccag tgcccagcag gatggggca ggtggctctg ggccccacta    25500
catggttgtg gcaggtccc ccatgtagtt cagtggggat cacaatctcc acctcccagg    25560
acccactcaa gctcccattt gcacagccca aactggagca ggatgggac atgggaggtg    25620 ggctctggct gtagcgtccg gtggtgggag gtggggtcca ggtggtgacg ctactgtccc    25680
tgcagtgctc tttgatgagc tgtaacagca ggcttggagg tggggctggg gacgacccag    25740
gcaaccctga ggggagctta agggagccag gcaaccctgg cacttttcca aggctttgca    25800
ttaactcaat agttccgcca tggccccggg ggtagtgcca tgtatttctg ttttaccgtc    25860
gaggaaacgg aggaaaccga ggcacaaaga aatggagtta attcctaaag tcacaggggcc    25920 aggaggtggc tgagtgggga ttcgaactca cccccagag ggcacacaca ggcaggcccc    25980
tgcacacacg cgcgcgcgcg cgcgcacaca catatacaca cacacgtgtc ctggaggagg    26040
cggcccgcag ggcgggacag ggcggggcgg gggcaggtcc cggccgccgg gaggaagtgg    26100
```

-continued

```
ccgggcggtc gcagggactc cggggcgacc gccgcgagtc cgcagtagtt cgggcc atg    26159
                                                           Met
                                                             1 gag gcg gag ccg ccg ctc tac ccg atg gcg ggg gct gcg ggg ccg cag    26207
Glu Ala Glu Pro Pro Leu Tyr Pro Met Ala Gly Ala Ala Gly Pro Gln
      5                  10                  15 ggc gac gag gac ctg ctc ggg gtc ccg gac ggg ccc gag gcc ccg        26252
Gly Asp Glu Asp Leu Leu Gly Val Pro Asp Gly Pro Glu Ala Pro
 20                  25                  30 gtgagcgggg acccggagtg cgaggcgcgg gcgtccctg tgggccaggg tcccccggc    26312 gggggcgggg cgggccgggg ggcggcgggc accgggggac acgggttcgg ggcgcgatcg  26372
cgggtgcgag cggcgtgcgt ggctcgcag ctg gac gag ctg gtg ggc gcg tac    26425
                                Leu Asp Glu Leu Val Gly Ala Tyr
                                     35                  40 ccc aac tac aac gag gag gag gag gag cgc cgc tac tac cgc cgc aag   26473
Pro Asn Tyr Asn Glu Glu Glu Glu Glu Arg Arg Tyr Tyr Arg Arg Lys
                  45                  50                  55 cgc ctg ggc gtg ctc aag aac gtg ctg gct gcc agc gcc ggg ggc atg   26521
Arg Leu Gly Val Leu Lys Asn Val Leu Ala Ala Ser Ala Gly Gly Met
         60                  65                  70 ctc acc tac ggc gtc tac ctg g gtaggtgccg ctcggggacc cggggccgcc     26573
Leu Thr Tyr Gly Val Tyr Leu
                75 ccgcccgctc ccagcccggc ccgggaaaca gaaaccgcgg gccgccgcct cccgcccgct  26633 ctcacttccc ctccgctgcc ctcgcagctg cagccacggc ccccgcggc ggggggtgggg  26693 ttgggggggtc aagtagcgca gcgtccccgg gtcccagcca gagcctcggt gtgggtgggg 26753 gacggggggtc cgggctcccg gacagacctg ccaccgtcag aattggaggc cggcggagca 26813 aggcgggtgg gggtctgggc ttagctggcc aagtggccgc gggctggcag aaggcgtggc 26873 gcagcccggg aaccccgctg tcctgagggg cgctgtcagc gggaatgcct tcggtgattg  26933 gagctccctg cgaggcctgc atgccgtctt ctgctcggtg gcgcccaaag ctaggctgct  26993 ccctgcacgc cgctctctgt cctgtcccca g gc  ctc ctg cag atg cag ctg    27044
                                   Gly Leu Leu Gln Met Gln Leu
                                                            85 atc ctg cac tac gac gag acc tac cgc gag gtg aag tat ggc aac atg  27092
Ile Leu His Tyr Asp Glu Thr Tyr Arg Glu Val Lys Tyr Gly Asn Met
         90                  95                  100 ggg ctg ccc gac atc gac agc aaa atg ctg atg ggc atc aac gtg act  27140
Gly Leu Pro Asp Ile Asp Ser Lys Met Leu Met Gly Ile Asn Val Thr
        105                 110                 115 ccc atc gcc gcc ctg ctc tac aca cct gtg ctc atc ag gtgggcgcgg    27188
Pro Ile Ala Ala Leu Leu Tyr Thr Pro Val Leu Ile Arg
    120                 125                 130 ctgctcctgt gggatgctgc ggtactccca tttcggaggg gtacagaggc cggcgggcca 27248 ggaggtgtcc atctgccggg gtgtttgtgg ggcgaggaa caagggagag gttttttttct 27308 acccggaagc ctgagagtga aggggggtgaa actcggattt ggggaaggaa acaggaactt 27368 tgcctcaggg cacatttggt ttccagcaac agattcacac gggctgagct ccctcccagc 27428 ttgcctgggc ctcacgtggc accctcctcg tggcctcctt ggaggcctcc cagagccact 27488 gtggccttca gggttgggggc tgtagagtta ggggtttctg atcggtcagc aaagtccagg 27548 cacccatgcc tggcccagtc gctgtgactg gtgctgaggg ggtgtttctc acagacaggc 27608 atggctgggc aggtgcccca gagctctccc ccagatntga gccctggagg tatgtggttc 27668 agcctccccca tcaccggtcc acagtgccct ccctgatggg acctggagac cagtggacaa 27728
```

```
attaggtgaa tttgagctcc ctcatcttta aaacaaacaa acaaacaaaa caacaagaga   27788
aaactccatt taaacaaaaa tttgaaaatt taaaacatct cccgttgcac aggcaggatt   27848
agaataactg aaatcataaa aaagaaaccc catctaagcc ctccaggaaa tcggctaccc   27908
atgctgtccc accagcatgc atggattaca ttcacatcct tgtccccaga gcacgtgtgt   27968
ggacgtgccc gtgtgtgtgt gtgtgtgtgt gtgtgtgtgt gtgtgtatgc aagcgggcta   28028
tgtttgcttt tgcttgctta ctttttttt tttgagacag atacttgctc tgtcacctag    28088
actgcagtgc agtggtgtga tctcggctca ctgcaacctc tgcctccag gctcaagcga    28148 ttctcctact tcagcaccct gagtagctgg gattacaggc gcctgccacc cggttaattt   28208
ttgtactttt agtagagatg gggtttcact atgttgacca ggctggtctt aaactcctga   28268
cctcaagtga ttctcctgcc ttggcctccc aaagtgctgg gattacaggc atgagccaca   28328
gtgcccagag cttgcttcct tcttttcact gagcatatct tagcctactc tacagccttc   28388
acagttacga ctttgcaatg gtagcatctt ctgcagatac ggtggcactg aacagtggct   28448
tggaattgga cactgcagtt ccttctgtgc ttacatctgt ttccttgttt ttttttttta   28508
aattatgtgt ttatttattt tattattatt attatttgag acagagtctc actctgtcac   28568
ccaggttaga gtgcagtggc acgaacacag ctcactgcct cctcaacccc cacacactgg   28628
gctcaagcaa tcctcccacc tcagcctccc gagtagctgg gcctacaggc gcacgccatc   28688
acatctggct gatttttaaa gtatttgtag cgatggggag ttgctatgtt gctcaggcca   28748
gtctcaaatt caccogcccc agcccacaa agtgttggga ttacaggtgt gagccaccac    28808
atccagcact cccccaattt tttaaacaat tattttccct aggatacatt ttcaacaatg   28868
tctttactag gtccaagcca tacaaaaggc tttatggctt ttgaaaccta tcacttctac   28928
taatagcagt gaactcttgt ctcctgtctg cccgacactc tattttattt atttattttt   28988 attttttactt tttttttgaa atggagtctc actctatcac caggctggag tgcaatggca   29048
caatctcggc tcactccaac ctctgcctcc caggttcaag cgattttcct gcctcagcct   29108
cctgagtagc tgggattaca ggcgcccgcc accacgctca gctaattttt tgtattttta   29168
gtaaagacgg ggtttcacca tgttggccag gctggtctca aacttctgac ctcaggtgat   29228
ctgcccacct ccacctccta aagtgctggg attacaggca cgagccacca cgcccggccg   29288
tgctgggcac tttataagcg caatttcatt cccaataatt tgaggaagct gctccagtct   29348
tagacatgaa gaaaccatgg tgttaaacaa cttgcccagg tcccacaggc agtaactggc   29408
agactgaagg cttgaacccc agtagaggga ctcaaatcca catgttcacc ccctgccaaa   29468
actaccaggc tgctttccca aagggttatg ccagtgtgtg tgaccactgg ctatatgtgc   29528
cacttttttt ttgagcaatc ttgctgttgc ccaggctgga gtgcggtgac gcgatctcag   29588
ctcacggcaa cctccacctc ctgggttcaa gcgattctcc tgcctcagcc tcccaagtag   29648
atgggattac aggtgtgcac caccacaccc ggctaatttt tgtattttta gtagaggtgg   29708
ggtttcacca tgttggccag gctggtctca aacttctgac ctcaggtgat ctgcccacct   29768
ccacctccta aagtgctgga attacagatg tgagccactg tgcctggcct atatgtgcca   29828
ctttcaaacc acatcctcac cagcagtgaa tgcacatttt tactggcatt tttacttaag   29888
gagcataaat acagaaaact tgaagatacc agtagtggtt tttggcctga tcagcctcca   29948
tgggtggttg agccctcatc ctgtcactca ccaagcccct tctattgtca ctgtgtgacc   30008
ttttcccaga cccagagagg tggaaacttc ctgactgacc accatggttc ataaaagcaa   30068
```

-continued

```
tggactggag gcagggggtgc cgggactctg gctctgctgc tcccagcagt ggggcctctt    30128
cctttctctt ctcccagcct gagtcaagcc cctgggccct acagacacag tgcatgagct    30188
tgggaggaga aggggggaatg ggagaatcag agagcccaga acacgcatga gggctggtta    30248
cacccatggg tcactctcca tcctcacagt ggtgatgaga ggcctgtggt ttgggctccg    30308
tgcccatatt acagctggga aaactgaggc acagtagctt gcctgaggcc actcagcaag    30368
tctgtgtatc tgatattcca tctcagtgcc ctcgactctc tctacctcac aaagccctgt    30428
gagctgggac ctgcggttgt ggccccgttt ggcttcaggc cacagtggtc cagcaggcct    30488
gtggtgccag catctctccc actgtccgca g g ttt ttt gga acg aag tgg atg       30541
                                    Phe Phe Gly Thr Lys Trp Met
                                                        135
atg ttc ctc gct gtg ggc atc tac gcc ctc ttt gtc tcc acc aac tac        30589
Met Phe Leu Ala Val Gly Ile Tyr Ala Leu Phe Val Ser Thr Asn Tyr
    140                 145                 150
tgg gag cgc tac tac acg ctt gtg ccc tcg gct gtg gcc ctg ggc atg        30637
Trp Glu Arg Tyr Tyr Thr Leu Val Pro Ser Ala Val Ala Leu Gly Met
155                 160                 165                 170
gcc atc gtg cct ctt tgg gct tcc atg ggc aac tac atc acc ag             30681
Ala Ile Val Pro Leu Trp Ala Ser Met Gly Asn Tyr Ile Thr Arg
                175                 180
gtgagcctgg tgggcagcag ggcaggaggc tggagacctg gccaagcctc cactttattg    30741
ccaactttgg ctgggggacc acaggaagcc ccttccgccc tctgggcctc agtttcccca    30801
caccgggggct ggtctgctcc tagctctggg tgcaggacac acaggagtgg cacaggtcgg   30861
gctggggaga gccttctctc ctttgtggtc cag g atg gcg cag aag tac cat        30913
                                      Met Ala Gln Lys Tyr His
                                                        190
gag tac tcc cac tac aag gag cag gat ggg cag ggg atg aag cag cgg       30961
Glu Tyr Ser His Tyr Lys Glu Gln Asp Gly Gln Gly Met Lys Gln Arg
            195                 200                 205
cct ccg cgg ggc tcc cac gcg ccc tat ctc ctg gtc ttc caa gcc atc       31009
Pro Pro Arg Gly Ser His Ala Pro Tyr Leu Leu Val Phe Gln Ala Ile
        210                 215                 220
ttc tac agc ttc ttc cat gtgagtgcca cgtgggccat tgttgggtgg              31057
Phe Tyr Ser Phe Phe His
    225
cagggggcaga cccacgcatt ggagcccatc cacagtctca accctctagt cccactttct   31117
ttcttttatt attgttattt ttaagaggcc tggtctcact atgttgccca gatggctttg    31177
aactcctggg ctccagtgat cctcccacct tggcctccca agtagctggg actacatgcg    31237
cacaccactg tatctgcccc accttcattt ctttttcttt ctttctttt tttttggtgg     31297
gggttggggg cagggtcttg cactgttgcc caggctggag tgcagtagtg cagtcacagc    31357
tcactgcaac cttgaactgc tgggctcaag tgatcctcct acctcagcct tctgagtagc    31417
tggcatcata tgcgtgtgct accacaccca gctaattttt tatttttttgt agagatagga   31477
tcttactatg ttgcccaggc tgcccatctt cctttcttga gcccacccca gcttgctcat    31537
ccatagagat agagatctca tctgccctt tccacaatgc tggccaggag gaggtcttcc    31597
tcattgggcg gccctgtaac cacactactc ccagaactgg gaaggcccct gttcccccaa    31657
ggctgtgcct ggaccccctcc ccagaccatg cctgtgtccc ttgcctggct ctgtgcctga   31717
gtctggtccc aactgcccctt gtttctgcag ctg agc ttc gcc tgc gcc cag ctg    31771
                                  Leu Ser Phe Ala Cys Ala Gln Leu
                                      230                 235
ccc atg att tat ttc ctg aac cac tac ctg tat gac ctg aac cac acg       31819
```

```
                         -continued

Pro Met Ile Tyr Phe Leu Asn His Tyr Leu Tyr Asp Leu Asn His Thr
        240                 245                 250 ctg tac aat gtg cag agc tgc g gttagtcctt gttggggtt ggggaggagt         31871
Leu Tyr Asn Val Gln Ser Cys
    255                 260 ccacaaagcc tgcttacttc cccagcagac actgggccct cactcacagg attcagggct    31931
ggcagcccag tgccccacgg ctctggtggg caagacacag ggccctgtag gagtaagtag    31991
ttaggacatc tgacccagcc aggagagtgg gtgggcgggg aagactgcct ggagaaggca    32051
ccatctgggc tgaggctgcc agtgggatct tccttggggc caggcaaaca gtcagagctc    32111
aatcagtgca gggggtgtgc atggaaatgt gaggtccact gagccttggg gnaatagggt    32171
gggaagcagg ggaaagatgc ccctttcccg gggaacaccc agccccagtg gtccaaaccc    32231
agccccagtg gtccaaacct ccaaactgct ctctgaagga actctgccct tgctctcact    32291
ctcccgccct ccaccgctcc tccgcggcct gcgtggctcc accctggtgg ctggattgac    32351
tgtgtgccct actctctgct cacggtgccc tcaccccac ccttcccag gc  acc aac    32408
                                                      Gly Thr Asn agc cac ggg atc ctc agc ggc ttc aac aag acg gtt ctg cgg acg ctc    32456
Ser His Gly Ile Leu Ser Gly Phe Asn Lys Thr Val Leu Arg Thr Leu
    265                 270                 275 ccg cgg agc gga aac ctc att gtg gtg gag agc gtg ctc atg gca gtg    32504
Pro Arg Ser Gly Asn Leu Ile Val Val Glu Ser Val Leu Met Ala Val
280                 285                 290                 295 gct tcc tgg cca tgc tgc tgg tgc ggcccgggat ggggcagga cagtcagtga    32558
Ala Ser Trp Pro Cys Cys Trp Cys
                    300 agcagagtgt ggttctgggg accgagtctg cgagaaaggg tctggatcgg atggcntggc    32618 ctgggtcggg ttgtggcctc ggggcaggcc gtaggcctgg gagcgcgatc tgagttgggg    32678 agctagggcc gagtgctgca gagcgggcat gaggctcgga ggcggggctg aggcctgtgg    32738 tccgaggcag gcgtgggcat ccagaggcca ggggaaggag ggaacaggct tggtccacag    32798 tttcgagctg gagacaagat cttagaagac tgactgagac ctgtgagggg gttggggaca    32858 ggaccaaggg tgagggctgg aaggtgtggc tcaaactgga agtgatactg gacggcagaa    32918 ctaaggcgtt ggcatgctgc agcctggcga tggagctggg aggcaaggcc cagtccgtgg    32978 ctgtgtcagg cggggcctag tgctgggacg cggggccgaa gtctgtgggt gtgtccgagg    33038 ggcggggact agcctggaag gcggggctga ggtctggcgc ggggctgaga aggaaggttg    33098 aagtctatgg atttgtctga atgtgagttg tgaagtgtgt gtatgtgaga gagaggggat    33158 ggggccttgg gctggaggc aagaccaccg tctttcggag tgtggtggcg tggctttgtg    33218 ctgagaggcg gggccttgag ctgggataag gcaagacctg ggtctgtggg agtgtctcag    33278 gggcggggcc ctggtttggg aggcggggcc gagctgggc aaggcccagg cacgtggtgc    33338 atctgaaggg cggggctgaa gcctggaggc caggcctggg cctggctggc cgcccttca    33398 agtaatgggt tcgcag gtg ctg ggt ttg tgc gga gcc gct tac cgg ccc acg    33450
               Val Leu Gly Leu Cys Gly Ala Ala Tyr Arg Pro Thr
                   305                 310                 315 gag gag atc gat ctg cgc agc gtg ggc tgg ggc aac atc ttc cag ctg    33498
Glu Glu Ile Asp Leu Arg Ser Val Gly Trp Gly Asn Ile Phe Gln Leu
                320                 325                 330 ccc ttc aag cac gtg cgt gac tac cgc ctg cgc cac ctc gtg cct ttc    33546
Pro Phe Lys His Val Arg Asp Tyr Arg Leu Arg His Leu Val Pro Phe
            335                 340                 345 ttt atc tac agc ggc ttc gag gtg ctc ttt gcc tgc act ggt atc gcc    33594
```

```
Phe Ile Tyr Ser Gly Phe Glu Val Leu Phe Ala Cys Thr Gly Ile Ala
        350                 355                 360 ttg gtaagtacag cctgcaaagg attgcccgac aaaagacaag atagccaggt         33647
Leu aaatttgaat tcaagtaaac aaagaataat ttttaattac atatgtaagt gtgtacatgt  33707
atatcccaaa tatccccctc ctgctttctc ttccctctct taccccgtc ccccctttac   33767 cttgggcaag ttattttaac ttctctgaat cgaaatggga tagcacccac agagtgttta  33827
gttccttgtg gggtacagcc cacggtgtct agggacattc caagcatttt cacacctgcc  33887
ctcagaacct tcccctgagc cttggagcga gtcaggcag tccagggagg cagggtgtg    33947 gcctaaggaa cacctcttgt ggggagtaag agccagccct tctccccacc tggctcttac  34007
tccccgtatc gcggggggcc cctctcccca ccctggctct taggacccc atcgcagggg   34067 ggtaaggcac cccccgcga tgcggggagt aagagccaac ccctctttc ccccgactc     34127 ttaggacccc catcgcaggg gggtgaggca ccccccacga tgcggggagt aagagccaga  34187
ccctcttccc ccctggctct taggacccc atcgcagggg ggtgaggcac ccccgcgatg   34247
cggggagggc tgagactgtg gtctgggctg ttccagactt caacactcac cccttgtccc  34307 cccgcag ggc tat ggc gtg tgc tcg gtg ggg ctg gag cgg ctg gct tac   34356
        Gly Tyr Gly Val Cys Ser Val Gly Leu Glu Arg Leu Ala Tyr
            365                 370                 375 ctc ctc gtg gct tac agc ctg ggc gcc tca gcc gcc tca ctc ctg ggc   34404
Leu Leu Val Ala Tyr Ser Leu Gly Ala Ser Ala Ala Ser Leu Leu Gly
380                 385                 390 ctg ctg ggc ctg tgg ctg cca cgc ccg gtg ccc ctg gtg gcc gga gca   34452
Leu Leu Gly Leu Trp Leu Pro Arg Pro Val Pro Leu Val Ala Gly Ala
395                 400                 405                 410 ggg gtg cac ctg ctg ctc acc ttc atc ctc ttt ttc tgg gcc cct gtg   34500
Gly Val His Leu Leu Leu Thr Phe Ile Leu Phe Phe Trp Ala Pro Val
            415                 420                 425 cct cgg gtc ctg caa cac agc tgg atc ctc tat gtg gca gct gcc ctt   34548
Pro Arg Val Leu Gln His Ser Trp Ile Leu Tyr Val Ala Ala Ala Leu
            430                 435                 440 tgg ggt gtg ggc agt gcc ctg aac aag act gga ctc agc a gtgagtatag  34598
Trp Gly Val Gly Ser Ala Leu Asn Lys Thr Gly Leu Ser
445                 450                 455 ctgtgggcac tggggggggg gggcgggc agggggcttt atggctatct gtgggtggtt    34658
ggcgagacat agacatccca gggacagata tggggtccca tggtcacata ggtcctgtg   34718 gacatggcag aggcaggtgg ggcttcctgt ggacactccg ggggtggaag ggaagtctta  34778
tggacacact ggggacagat gggtagggtg tggacaccct ggagacaggt atgggggttc  34838
catgccatgg acattctgtt aataccccag agcgggcaca gggcccatc aacactggag   34898 ggtcagtgtg aagtctcgtg gctacatggg gcaggtgtgg ggctctgtgg acacccctta  34958
gggacagtgt gaaaaacaca tcagggattc ccctttca taccagggga cagggcttac   35018
cctggcatag ttttcatgac acttggagca gatgttttgg tctctgcttc acggagcatg  35078
tggtaggagc aagtggcctg ttgtacaccc atggcataga tacagacatg gcctttgta   35138 tagagaggag caggcctgca gccccaaccc agtctgctca gtaccagagt ccaggcccca  35198
ggtctgggct gctggggaac agggccctgt ttgcagaagg cagcgggtgg gcccatgttc  35258
agctccagga tgctccctga ccacagatgg gcacacgcag tgaaacacag ctagcacaca  35318
tgggcagtcc tgccgggcat ccatgtcagt gtctgttctg atgggccgaa gctgtgaaca  35378
gttttgaacg tcatccttgg gggtgtggag tagccgaggt catgcctgct gctggcaggg  35438
```

```
cggaggctgg ctctgtgtct ctgtctgtag caggggctgg agcctcatac tgcaccacag    35498
tctcttggcc gttttgccca aggatagcca attctgggca gagtccagcc tgggtatctt    35558
gaacccatgt tgtgccctgt ctggtcctgg catcccctct gcccagctcc atatcccatc    35618
tcctccggtg aaccccgggg ggtccttgtc tcttcatagc agcactgtgg gggtaaagtc    35678
accctgcagg gccccaaaac aggagtgttc atatcctgag tgcctggtga aggtgttaat    35738
agtggcccct atgatttggc aggtgccatg cccactttct cactttagaa cttcagaaca    35798
cagcacacaa taggcataag ctcatctcac cattgggaaa agcagctctg gggagttaag    35858
tacccaaatc acccacagag ccaacattac agccctgaga acgagcgtgc atcttctgac    35918
tcccaatcca ttactcttgt tgcccaccct gggaggactc actggaaagg aatcccccct    35978
ctccatgctt agcttcaggt ttgatttgca gagttggcag ctgcaaacag ttcgatctct    36038
ctagtcctgg ctgaggagga gaaacagcgc ctgcaagctt ggcactgcac acctgggttg    36098
gggacaggac atgactaagc acagagcttt cttcttttga ggccacgcat gtggtgcgga    36158
gcgggaacac ctgcatccac acagcccgag gcacctgctc ctacttctgc ttagcgtgtg    36218
agcagtgtgg tgaccagggt ctccaccagg gggcaggcca ggaccgcctc acagcacttt    36278
ctaggcgctc tctggtccgg ggctgggacc catacagggc ttagtaaagt tcgtagatgt    36338
tagctcggta gccccaggcc ccaggtgaca cctctcccct gcctgccctg tactgcctgc    36398 ctgcag ca  ctc ctg gga atc ttg tac gaa gac aag gag aga cag gac      36445
        Thr Leu Leu Gly Ile Leu Tyr Glu Asp Lys Glu Arg Gln Asp
                    460                 465 ttc atc ttc acc atc tac cac tgg tgg cag gct gtg gcc atc ttc acc      36493
Phe Ile Phe Thr Ile Tyr His Trp Trp Gln Ala Val Ala Ile Phe Thr
470                 475                 480                 485 gtg tac ctg ggc tcg agc ctg cac atg aag gtgagactgg gcagggttgg        36543
Val Tyr Leu Gly Ser Ser Leu His Met Lys
                490                 495 gggcccatg cccaatgaca ggtacttcct tagcccctgc cctggcttca cagcttccta     36603
aatgccaccc cttcccaagc cagtctctgg gccaaggccc cattcctgca gcccactggg    36663
tggcccccaa ctcagcaccc cacttactgg cccacctcca gccagtctca gtttgcccat    36723
ctctgagggg atttgtgggt gcatcacagc catcctgtgg gctgtttggt accttgttct    36783
ccagatgttg ggtctgtctc tcttcatggc ctgaagggga gcaggctcct catgctctgc    36843
tcacaaaaaa tggtggctcg gtctagcaag tcccagttgc taaacatttt ttaaaaatag    36903
aactaaaggc cgggcgcggt ggctcacgcc tgtaatccca gcactttggg aggccgaggc    36963
gagtggattg cctgaggtag ggagtttgag accagcctga ccgacatggt gaaacctcgt    37023
ctctactaaa aatacaaaaa ttagccgggc gtggtggcag gtgcctgtaa tcacagctac    37083
tcaggaggct gaggcaggag aatcacttga actgggaggc ggaggttgca gttagccgag    37143
acggggcgtt ggcactccat ccagcctaag caacaagagc gaaactccgt ctcaaaataa    37203
aaataaaaat agaactaaaa atagcaggga gtgggctggc agtagtggct cacgcctgta    37263
atcccagcat tttgagacgc tgaggtgggg gttctgagat ctggagttcg agaccagcct    37323
gggtaacagg ctgtgaaact ctgtctctac taaaaacaca aaaattagct gggcatggtg    37383
gcacgtccct gtgatcccag ctactctgga ggctgaggca caagaatggc ttgaacctgg    37443
gagatggagg ttgcagtgag ccaagatcgc gccaccgcac ttcagcctgg aggacagagc    37503
gagactctgt cttccaaaaa aaaaaaaaag gaaaaaaaaa aagaaaagc agtgagtggg     37563
```

```
ctgggcatgg tggctcacgc ctgtaatccc aacactttgg gaggctgagg caggaggatt    37623
gcttgaggcc aggagttcaa gaccagcctg ggcaacatag gagaccctgt ctctacaaaa    37683
aatttaaaaa atagctgggc gtagtggcgt gtgcctgtag ttccagctac ttgggagact    37743
gaagtgggag gatggcttga gcctggaaga ttgaggctga agtgagcgtg ccactgcgct    37803
ccagcagtgg gtgggggaag ggagggaggg ggcgcggtgg ggaaacggag cgaccgtgtc    37863
tggaaaaaag aaaagagcag gaagtatgca tacagatatg tgtgtatgta ctgggctatg    37923
gtgtgaaatc attcctgact gcgggttata gtcaaaaccc catgaaaagc atcactacag    37983
cccacgggtg tgtcagggac acagtgttgt gagccctggg aaggcagggc ctgtggccag    38043
cactttatca acactggcgc atgcacccta tgaggcaaag ggatttgcat tgtcccctta    38103
cagtgtggga cactgaggtc gccaggggcg tggcgactgt aagggacagt gctggatgtg    38163
agcctcgcct gcaggaggcg gtccaggaag catgggtgga ggggctggag aagttgaggg    38223
ccgcgtggcc cgggaggctc ccggaggagg gaagggccta tctcagcgag ggcataggc    38283 ggggaaggtg cggggcgagg cggccgcggg tccctggcat ccctctcctt acgcccag     38341
```

```
                   gct aag ctg gcg gtg ctg ctg gtg acg ctg gtg gcg gcc gcg gtc tcc      38389
                   Ala Lys Leu Ala Val Leu Leu Val Thr Leu Val Ala Ala Ala Val Ser
                                500             505                 510 tac ctg cgg atg gag cag aag ctg cgc cgg ggc gtg gcc ccg cgc cag                      38437
Tyr Leu Arg Met Glu Gln Lys Leu Arg Arg Gly Val Ala Pro Arg Gln
        515                 520                 525 ccc cgc atc ccg cgg ccc cag cac aag gtg cgc ggt tac cgc tac ttg                      38485
Pro Arg Ile Pro Arg Pro Gln His Lys Val Arg Gly Tyr Arg Tyr Leu
    530                 535                 540 gag gag gac aac tcg gac gag agc gac gcg gag ggc gag cat ggg gac                      38533
Glu Glu Asp Asn Ser Asp Glu Ser Asp Ala Glu Gly Glu His Gly Asp
545                 550                 555 ggc gcg gag gag gag gcg ccg ccc gca ggg ccc agg cct ggc ccc gag                      38581
Gly Ala Glu Glu Glu Ala Pro Pro Ala Gly Pro Arg Pro Gly Pro Glu
        560                 565                 570             575 ccc gct gga ctc ggc cgc cgg ccc tgc ccg tac gaa cag gcg cag ggg                      38629
Pro Ala Gly Leu Gly Arg Arg Pro Cys Pro Tyr Glu Gln Ala Gln Gly
                580                 585                 590 gga gac ggg ccg gag gag cag tga                                                      38653
Gly Asp Gly Pro Glu Glu Gln
            595
```

```
<210> SEQ ID NO 2
<211> LENGTH: 17
<212> TYPE: DNA
<213> ORGANISM: synthetic

<400> SEQUENCE: 2
ttgcactttc tcatcat                                                                    17

<210> SEQ ID NO 3
<211> LENGTH: 13
<212> TYPE: DNA
<213> ORGANISM: synthetic

<400> SEQUENCE: 3
ccagccaccc acc                                                                        13

<210> SEQ ID NO 4
<211> LENGTH: 14
<212> TYPE: DNA
<213> ORGANISM: synthetic
```

```
<400> SEQUENCE: 4
gctctccccc agat                                                 14

<210> SEQ ID NO 5
<211> LENGTH: 14
<212> TYPE: DNA
<213> ORGANISM: synthetic

<400> SEQUENCE: 5
actgagcctt gggg                                                 14

<210> SEQ ID NO 6
<211> LENGTH: 17
<212> TYPE: DNA
<213> ORGANISM: synthetic

<400> SEQUENCE: 6
ggtctggatc ggatggc                                              17

<210> SEQ ID NO 7
<211> LENGTH: 13
<212> TYPE: DNA
<213> ORGANISM: synthetic

<400> SEQUENCE: 7
catcattaca cag                                                  13

<210> SEQ ID NO 8
<211> LENGTH: 14
<212> TYPE: DNA
<213> ORGANISM: synthetic

<400> SEQUENCE: 8
aggtggattc atgc                                                 14

<210> SEQ ID NO 9
<211> LENGTH: 13
<212> TYPE: DNA
<213> ORGANISM: synthetic

<400> SEQUENCE: 9
cctccagggc tca                                                  13

<210> SEQ ID NO 10
<211> LENGTH: 13
<212> TYPE: DNA
<213> ORGANISM: synthetic

<400> SEQUENCE: 10
ttcccaccct att                                                  13

<210> SEQ ID NO 11
<211> LENGTH: 13
<212> TYPE: DNA
<213> ORGANISM: synthetic

<400> SEQUENCE: 11
ccgacccagg cca                                                  13

<210> SEQ ID NO 12
<211> LENGTH: 13
<212> TYPE: DNA
```

```
<213> ORGANISM: synthetic

<400> SEQUENCE: 12
catcatactg tgt                                                      13

<210> SEQ ID NO 13
<211> LENGTH: 13
<212> TYPE: DNA
<213> ORGANISM: synthetic

<400> SEQUENCE: 13
catcatgctg tgt                                                      13

<210> SEQ ID NO 14
<211> LENGTH: 13
<212> TYPE: DNA
<213> ORGANISM: synthetic

<400> SEQUENCE: 14
cccacctgca tga                                                      13

<210> SEQ ID NO 15
<211> LENGTH: 13
<212> TYPE: DNA
<213> ORGANISM: synthetic

<400> SEQUENCE: 15
cccacccgca tga                                                      13

<210> SEQ ID NO 16
<211> LENGTH: 13
<212> TYPE: DNA
<213> ORGANISM: synthetic

<400> SEQUENCE: 16
ccagatctga gcc                                                      13

<210> SEQ ID NO 17
<211> LENGTH: 13
<212> TYPE: DNA
<213> ORGANISM: synthetic

<400> SEQUENCE: 17
ccagatgtga gcc                                                      13

<210> SEQ ID NO 18
<211> LENGTH: 13
<212> TYPE: DNA
<213> ORGANISM: synthetic

<400> SEQUENCE: 18
ttggggaaat agg                                                      13

<210> SEQ ID NO 19
<211> LENGTH: 13
<212> TYPE: DNA
<213> ORGANISM: synthetic

<400> SEQUENCE: 19
ttggggcaat agg                                                      13

<210> SEQ ID NO 20
<211> LENGTH: 13
```

-continued

```
<212> TYPE: DNA
<213> ORGANISM: synthetic

<400> SEQUENCE: 20
gatggcatgg cct                                                        13

<210> SEQ ID NO 21
<211> LENGTH: 13
<212> TYPE: DNA
<213> ORGANISM: synthetic

<400> SEQUENCE: 21
gatggcgtgg cct                                                        13

<210> SEQ ID NO 22
<211> LENGTH: 13
<212> TYPE: DNA
<213> ORGANISM: synthetic

<400> SEQUENCE: 22
acacagtatg atg                                                        13

<210> SEQ ID NO 23
<211> LENGTH: 13
<212> TYPE: DNA
<213> ORGANISM: synthetic

<400> SEQUENCE: 23
acacagcatg atg                                                        13

<210> SEQ ID NO 24
<211> LENGTH: 13
<212> TYPE: DNA
<213> ORGANISM: synthetic

<400> SEQUENCE: 24
tcatgcaggt ggg                                                        13

<210> SEQ ID NO 25
<211> LENGTH: 13
<212> TYPE: DNA
<213> ORGANISM: synthetic

<400> SEQUENCE: 25
tcatgcgggt ggg                                                        13

<210> SEQ ID NO 26
<211> LENGTH: 13
<212> TYPE: DNA
<213> ORGANISM: synthetic

<400> SEQUENCE: 26
ggctcagatc tgg                                                        13

<210> SEQ ID NO 27
<211> LENGTH: 13
<212> TYPE: DNA
<213> ORGANISM: synthetic

<400> SEQUENCE: 27
ggctcacatc tgg                                                        13

<210> SEQ ID NO 28
```

-continued

```
<211> LENGTH: 13
<212> TYPE: DNA
<213> ORGANISM: synthetic

<400> SEQUENCE: 28
cctatttccc caa                                                       13

<210> SEQ ID NO 29
<211> LENGTH: 13
<212> TYPE: DNA
<213> ORGANISM: synthetic

<400> SEQUENCE: 29
cctattgccc caa                                                       13

<210> SEQ ID NO 30
<211> LENGTH: 13
<212> TYPE: DNA
<213> ORGANISM: synthetic

<400> SEQUENCE: 30
aggccatgcc atc                                                       13

<210> SEQ ID NO 31
<211> LENGTH: 13
<212> TYPE: DNA
<213> ORGANISM: synthetic

<400> SEQUENCE: 31
aggccacgcc atc                                                       13

<210> SEQ ID NO 32
<211> LENGTH: 13
<212> TYPE: DNA
<213> ORGANISM: synthetic

<400> SEQUENCE: 32
ctgtgtaatg atg                                                       13

<210> SEQ ID NO 33
<211> LENGTH: 13
<212> TYPE: DNA
<213> ORGANISM: synthetic

<400> SEQUENCE: 33
gcatgaatcc acc                                                       13

<210> SEQ ID NO 34
<211> LENGTH: 13
<212> TYPE: DNA
<213> ORGANISM: synthetic

<400> SEQUENCE: 34
tgagccctgg agg                                                       13

<210> SEQ ID NO 35
<211> LENGTH: 13
<212> TYPE: DNA
<213> ORGANISM: synthetic

<400> SEQUENCE: 35
aatagggtgg gaa                                                       13
```

```
<210> SEQ ID NO 36
<211> LENGTH: 13
<212> TYPE: DNA
<213> ORGANISM: synthetic

<400> SEQUENCE: 36
tggcctgggt cgg                                                          13

<210> SEQ ID NO 37
<211> LENGTH: 16
<212> TYPE: DNA
<213> ORGANISM: synthetic

<400> SEQUENCE: 37
atgatgagaa agtcaa                                                       16

<210> SEQ ID NO 38
<211> LENGTH: 13
<212> TYPE: DNA
<213> ORGANISM: synthetic

<400> SEQUENCE: 38
ggtgggtggc tgg                                                          13

<210> SEQ ID NO 39
<211> LENGTH: 14
<212> TYPE: DNA
<213> ORGANISM: synthetic

<400> SEQUENCE: 39
atctggggga gagc                                                         14

<210> SEQ ID NO 40
<211> LENGTH: 14
<212> TYPE: DNA
<213> ORGANISM: synthetic

<400> SEQUENCE: 40
ccccaaggct cagt                                                         14

<210> SEQ ID NO 41
<211> LENGTH: 17
<212> TYPE: DNA
<213> ORGANISM: synthetic

<400> SEQUENCE: 41
gccatccgat ccagacc                                                      17

<210> SEQ ID NO 42
<211> LENGTH: 23
<212> TYPE: DNA
<213> ORGANISM: synthetic

<400> SEQUENCE: 42
aatacaaaaa tcagctgggt gta                                               23

<210> SEQ ID NO 43
<211> LENGTH: 20
<212> TYPE: DNA
<213> ORGANISM: synthetic

<400> SEQUENCE: 43
gatgtgggga acagacaggt                                                   20
```

-continued

```
<210> SEQ ID NO 44
<211> LENGTH: 18
<212> TYPE: DNA
<213> ORGANISM: synthetic

<400> SEQUENCE: 44
tggtgctgag ggggtgtt                                                       18

<210> SEQ ID NO 45
<211> LENGTH: 21
<212> TYPE: DNA
<213> ORGANISM: synthetic

<400> SEQUENCE: 45
gatttcctgg agggcttaga t                                                   21

<210> SEQ ID NO 46
<211> LENGTH: 19
<212> TYPE: DNA
<213> ORGANISM: synthetic

<400> SEQUENCE: 46
gctctggtgg gcaagacac                                                      19

<210> SEQ ID NO 47
<211> LENGTH: 18
<212> TYPE: DNA
<213> ORGANISM: synthetic

<400> SEQUENCE: 47
cactggggct gggtgttc                                                       18

<210> SEQ ID NO 48
<211> LENGTH: 18
<212> TYPE: DNA
<213> ORGANISM: synthetic

<400> SEQUENCE: 48
gatgggggca ggacagtc                                                       18

<210> SEQ ID NO 49
<211> LENGTH: 21
<212> TYPE: DNA
<213> ORGANISM: synthetic

<400> SEQUENCE: 49
ttgtctccag ctcgaaactg t                                                   21

<210> SEQ ID NO 50
<211> LENGTH: 2282
<212> TYPE: DNA
<213> ORGANISM: homo sapiens
<220> FEATURE:
<221> NAME/KEY: CDS
<222> LOCATION: (42)..(1835)
<223> OTHER INFORMATION:

<400> SEQUENCE: 50
gactccgggg cgaccgccgc gagtccgcag tagttcgggc atg gag gcg gag ccg        56
                                            Met Glu Ala Glu Pro
                                             1               5 ccg ctc tac ccg atg gcg ggg gct gcg ggg ccg cag ggc gac gag gac       104
Pro Leu Tyr Pro Met Ala Gly Ala Ala Gly Pro Gln Gly Asp Glu Asp
             10                  15                  20
```

```
ctg ctc ggg gtc ccg gac ggg ccc gag gcc ccg ctg gac gag ctg gtg      152
Leu Leu Gly Val Pro Asp Gly Pro Glu Ala Pro Leu Asp Glu Leu Val
            25                  30                  35 ggc gcg tac ccc aac tac aac gag gag gag gag cgc cgc tac tac          200
Gly Ala Tyr Pro Asn Tyr Asn Glu Glu Glu Glu Arg Arg Tyr Tyr
        40                  45                  50 cgc cgc aag cgc ctg ggc gtg ctc aag aac gtg ctg gct gcc agc gcc      248
Arg Arg Lys Arg Leu Gly Val Leu Lys Asn Val Leu Ala Ala Ser Ala
55                  60                  65 ggg ggc atg ctc acc tac ggc gtc tac ctg ggc ctc ctg cag atg cag      296
Gly Gly Met Leu Thr Tyr Gly Val Tyr Leu Gly Leu Leu Gln Met Gln
70                  75                  80                  85 ctg atc ctg cac tac gac gag acc tac cgc gag gtg aag tat ggc aac      344
Leu Ile Leu His Tyr Asp Glu Thr Tyr Arg Glu Val Lys Tyr Gly Asn
            90                  95                  100 atg ggg ctg ccc gac atc gac agc aaa atg ctg atg ggc atc aac gtg      392
Met Gly Leu Pro Asp Ile Asp Ser Lys Met Leu Met Gly Ile Asn Val
        105                 110                 115 act ccc atc gcc gcc ctg ctc tac aca cct gtg ctc atc agg ttt ttt      440
Thr Pro Ile Ala Ala Leu Leu Tyr Thr Pro Val Leu Ile Arg Phe Phe
        120                 125                 130 gga acg aag tgg atg atg ttc ctc gct gtg ggc atc tac gcc ctc ttt      488
Gly Thr Lys Trp Met Met Phe Leu Ala Val Gly Ile Tyr Ala Leu Phe
135                 140                 145 gtc tcc acc aac tac tgg gag cgc tac tac acg ctt gtg ccc tcg gct      536
Val Ser Thr Asn Tyr Trp Glu Arg Tyr Tyr Thr Leu Val Pro Ser Ala
150                 155                 160                 165 gtg gcc ctg ggc atg gcc atc gtg cct ctt tgg gct tcc atg ggc aac      584
Val Ala Leu Gly Met Ala Ile Val Pro Leu Trp Ala Ser Met Gly Asn
            170                 175                 180 tac atc acc agg atg gcg cag aag tac cat gag tac tcc cac tac aag      632
Tyr Ile Thr Arg Met Ala Gln Lys Tyr His Glu Tyr Ser His Tyr Lys
        185                 190                 195 gag cag gat ggg cag ggg atg aag cag cgg cct ccg cgg ggc tcc cac      680
Glu Gln Asp Gly Gln Gly Met Lys Gln Arg Pro Pro Arg Gly Ser His
        200                 205                 210 gcg ccc tat ctc ctg gtc ttc caa gcc atc ttc tac agc ttc ttc cat      728
Ala Pro Tyr Leu Leu Val Phe Gln Ala Ile Phe Tyr Ser Phe Phe His
215                 220                 225 ctg agc ttc gcc tgc gcc cag ctg ccc atg att tat ttc ctg aac cac      776
Leu Ser Phe Ala Cys Ala Gln Leu Pro Met Ile Tyr Phe Leu Asn His
230                 235                 240                 245 tac ctg tat gac ctg aac cac acg ctg tac aat gtg cag agc tgc ggc      824
Tyr Leu Tyr Asp Leu Asn His Thr Leu Tyr Asn Val Gln Ser Cys Gly
            250                 255                 260 acc aac agc cac ggg atc ctc agc ggc ttc aac aag acg gtt ctg cgg      872
Thr Asn Ser His Gly Ile Leu Ser Gly Phe Asn Lys Thr Val Leu Arg
        265                 270                 275 acg ctc ccg cgg agc gga aac ctc att gtg gtg gag agc gtg ctc atg      920
Thr Leu Pro Arg Ser Gly Asn Leu Ile Val Val Glu Ser Val Leu Met
        280                 285                 290 gca gtg gcc ttc ctg gcc atg ctg ctg gtg ctg ggt ttg tgc gga gcc      968
Ala Val Ala Phe Leu Ala Met Leu Leu Val Leu Gly Leu Cys Gly Ala
295                 300                 305 gct tac cgg ccc acg gag gag atc gat ctg cgc agc gtg ggc tgg ggc      1016
Ala Tyr Arg Pro Thr Glu Glu Ile Asp Leu Arg Ser Val Gly Trp Gly
310                 315                 320                 325 aac atc ttc cag ctg ccc ttc aag cac gtg cgt gac tac cgc ctg cgc      1064
Asn Ile Phe Gln Leu Pro Phe Lys His Val Arg Asp Tyr Arg Leu Arg
```

|   |   |   |   |   |   |   |   |   |   |   |   |   |   |   |   |   |
|---|---|---|---|---|---|---|---|---|---|---|---|---|---|---|---|---|
|   |   |   | 330 |   |   |   |   | 335 |   |   |   |   | 340 |   |   |   |
| cac | ctc | gtg | cct | ttc | ttt | atc | tac | agc | ggc | ttc | gag | gtg | ctc | ttt | gcc | 1112 |
| His | Leu | Val | Pro | Phe | Phe | Ile | Tyr | Ser | Gly | Phe | Glu | Val | Leu | Phe | Ala |   |
|   |   |   | 345 |   |   |   |   | 350 |   |   |   |   | 355 |   |   |   |
| tgc | act | ggt | atc | gcc | ttg | ggc | tat | ggc | gtg | tgc | tcg | gtg | ggg | ctg | gag | 1160 |
| Cys | Thr | Gly | Ile | Ala | Leu | Gly | Tyr | Gly | Val | Cys | Ser | Val | Gly | Leu | Glu |   |
|   |   | 360 |   |   |   |   | 365 |   |   |   |   | 370 |   |   |   |   |
| cgg | ctg | gct | tac | ctc | ctc | gtg | gct | tac | agc | ctg | ggc | gcc | tca | gcc | gcc | 1208 |
| Arg | Leu | Ala | Tyr | Leu | Leu | Val | Ala | Tyr | Ser | Leu | Gly | Ala | Ser | Ala | Ala |   |
|   | 375 |   |   |   |   | 380 |   |   |   |   | 385 |   |   |   |   |   |
| tca | ctc | ctg | ggc | ctg | ctg | ggc | ctg | tgg | ctg | cca | cgc | ccg | gtg | ccc | ctg | 1256 |
| Ser | Leu | Leu | Gly | Leu | Leu | Gly | Leu | Trp | Leu | Pro | Arg | Pro | Val | Pro | Leu |   |
| 390 |   |   |   |   | 395 |   |   |   |   | 400 |   |   |   |   | 405 |   |
| gtg | gcc | gga | gca | ggg | gtg | cac | ctg | ctg | ctc | acc | ttc | atc | ctc | ttt | ttc | 1304 |
| Val | Ala | Gly | Ala | Gly | Val | His | Leu | Leu | Leu | Thr | Phe | Ile | Leu | Phe | Phe |   |
|   |   |   |   | 410 |   |   |   |   | 415 |   |   |   |   | 420 |   |   |
| tgg | gcc | cct | gtg | cct | cgg | gtc | ctg | caa | cac | agc | tgg | atc | ctc | tat | gtg | 1352 |
| Trp | Ala | Pro | Val | Pro | Arg | Val | Leu | Gln | His | Ser | Trp | Ile | Leu | Tyr | Val |   |
|   |   |   | 425 |   |   |   |   | 430 |   |   |   |   | 435 |   |   |   |
| gca | gct | gcc | ctt | tgg | ggt | gtg | ggc | agt | gcc | ctg | aac | aag | act | gga | ctc | 1400 |
| Ala | Ala | Ala | Leu | Trp | Gly | Val | Gly | Ser | Ala | Leu | Asn | Lys | Thr | Gly | Leu |   |
|   |   | 440 |   |   |   |   | 445 |   |   |   |   | 450 |   |   |   |   |
| agc | aca | ctc | ctg | gga | atc | ttg | tac | gaa | gac | aag | gag | aga | cag | gac | ttc | 1448 |
| Ser | Thr | Leu | Leu | Gly | Ile | Leu | Tyr | Glu | Asp | Lys | Glu | Arg | Gln | Asp | Phe |   |
|   | 455 |   |   |   |   | 460 |   |   |   |   | 465 |   |   |   |   |   |
| atc | ttc | acc | atc | tac | cac | tgg | tgg | cag | gct | gtg | gcc | atc | ttc | acc | gtg | 1496 |
| Ile | Phe | Thr | Ile | Tyr | His | Trp | Trp | Gln | Ala | Val | Ala | Ile | Phe | Thr | Val |   |
| 470 |   |   |   |   | 475 |   |   |   |   | 480 |   |   |   |   | 485 |   |
| tac | ctg | ggc | tcg | agc | ctg | cac | atg | aag | gct | aag | ctg | gcg | gtg | ctg | ctg | 1544 |
| Tyr | Leu | Gly | Ser | Ser | Leu | His | Met | Lys | Ala | Lys | Leu | Ala | Val | Leu | Leu |   |
|   |   |   |   | 490 |   |   |   |   | 495 |   |   |   |   | 500 |   |   |
| gtg | acg | ctg | gtg | gcg | gcc | gcg | gtc | tcc | tac | ctg | cgg | att | gag | cag | aag | 1592 |
| Val | Thr | Leu | Val | Ala | Ala | Ala | Val | Ser | Tyr | Leu | Arg | Ile | Glu | Gln | Lys |   |
|   |   |   | 505 |   |   |   |   | 510 |   |   |   |   | 515 |   |   |   |
| ctg | cgg | cgg | ggc | gtg | gcc | ccg | cgc | cag | ccc | cgc | atc | ccg | cgg | ccc | cag | 1640 |
| Leu | Arg | Arg | Gly | Val | Ala | Pro | Arg | Gln | Pro | Arg | Ile | Pro | Arg | Pro | Gln |   |
|   | 520 |   |   |   |   | 525 |   |   |   |   | 530 |   |   |   |   |   |
| cac | aag | gtg | cgc | ggt | tac | cgc | tac | ttg | gag | gag | gac | aac | tcg | gac | gag | 1688 |
| His | Lys | Val | Arg | Gly | Tyr | Arg | Tyr | Leu | Glu | Glu | Asp | Asn | Ser | Asp | Glu |   |
| 535 |   |   |   |   | 540 |   |   |   |   | 545 |   |   |   |   |   |   |
| agc | gac | gcg | gag | ggc | gag | cat | ggg | gac | ggc | gcg | gag | gag | gcg | ccg | 1736 |
| Ser | Asp | Ala | Glu | Gly | Glu | His | Gly | Asp | Gly | Ala | Glu | Glu | Ala | Pro |   |
| 550 |   |   |   |   | 555 |   |   |   |   | 560 |   |   |   |   | 565 |   |
| ccc | gca | ggg | ccc | agg | cct | ggc | ccc | gag | ccc | gct | gga | ctc | ggc | cgc | cgg | 1784 |
| Pro | Ala | Gly | Pro | Arg | Pro | Gly | Pro | Glu | Pro | Ala | Gly | Leu | Gly | Arg | Arg |   |
|   |   |   | 570 |   |   |   |   | 575 |   |   |   |   | 580 |   |   |   |
| ccc | tgc | ccg | tac | gaa | cag | gcg | cag | ggg | gga | gac | ggg | ccg | gag | gag | cag | 1832 |
| Pro | Cys | Pro | Tyr | Glu | Gln | Ala | Gln | Gly | Gly | Asp | Gly | Pro | Glu | Glu | Gln |   |
|   |   | 585 |   |   |   |   | 590 |   |   |   |   | 595 |   |   |   |   |

| | |
|---|---|
| tga ggggccgcct ggtcccggga ctcagcctcc ctcctcgccg gcctcagttt | 1885 |
| accacgtctg aggtcggggg gaccccctcc gagtcccgcg ctgtcttcaa aggcccctgt | 1945 |
| ctcccctccc cgacgttggg gacgcccctc ccagagccca ggtcacctcc gggcttccgc | 2005 |
| agccccctcc aaggcggagt ggagccttgg gaacccctcg gccaagcaca ggggttcgaa | 2065 |
| aatacagctg aaacccgcgc ggcccttagc acgcgcccca gcgccggagc acggtcaggg | 2125 |
| tcttcttgcg accggcccg ctccagatcc ccacagcttt cggccgcgga cccgggccgc | 2185 |
| gtgtgagcgc actttgcacc tcctatcccc agggtccgcc gagagccacg attttttaca | 2245 | gaaaatgagc aataaagaga ttttgtactg tcaaaaa                                    2282

<210> SEQ ID NO 51
<211> LENGTH: 597
<212> TYPE: PRT
<213> ORGANISM: homo sapiens

<400> SEQUENCE: 51

```
Met Glu Ala Glu Pro Pro Leu Tyr Pro Met Ala Gly Ala Ala Gly Pro
1               5                   10                  15

Gln Gly Asp Glu Asp Leu Leu Gly Val Pro Asp Gly Pro Glu Ala Pro
            20                  25                  30

Leu Asp Glu Leu Val Gly Ala Tyr Pro Asn Tyr Asn Glu Glu Glu Glu
        35                  40                  45

Glu Arg Arg Tyr Tyr Arg Arg Lys Arg Leu Gly Val Leu Lys Asn Val
50                  55                  60

Leu Ala Ala Ser Ala Gly Gly Met Leu Thr Tyr Gly Val Tyr Leu Gly
65                  70                  75                  80

Leu Leu Gln Met Gln Leu Ile Leu His Tyr Asp Glu Thr Tyr Arg Glu
                85                  90                  95

Val Lys Tyr Gly Asn Met Gly Leu Pro Asp Ile Asp Ser Lys Met Leu
            100                 105                 110

Met Gly Ile Asn Val Thr Pro Ile Ala Ala Leu Leu Tyr Thr Pro Val
        115                 120                 125

Leu Ile Arg Phe Phe Gly Thr Lys Trp Met Met Phe Leu Ala Val Gly
130                 135                 140

Ile Tyr Ala Leu Phe Val Ser Thr Asn Tyr Trp Glu Arg Tyr Tyr Thr
145                 150                 155                 160

Leu Val Pro Ser Ala Val Ala Leu Gly Met Ala Ile Val Pro Leu Trp
                165                 170                 175

Ala Ser Met Gly Asn Tyr Ile Thr Arg Met Ala Gln Lys Tyr His Glu
            180                 185                 190

Tyr Ser His Tyr Lys Glu Gln Asp Gly Gln Gly Met Lys Gln Arg Pro
        195                 200                 205

Pro Arg Gly Ser His Ala Pro Tyr Leu Leu Val Phe Gln Ala Ile Phe
210                 215                 220

Tyr Ser Phe Phe His Leu Ser Phe Ala Cys Ala Gln Leu Pro Met Ile
225                 230                 235                 240

Tyr Phe Leu Asn His Tyr Leu Tyr Asp Leu Asn His Thr Leu Tyr Asn
                245                 250                 255

Val Gln Ser Cys Gly Thr Asn Ser His Gly Ile Leu Ser Gly Phe Asn
            260                 265                 270

Lys Thr Val Leu Arg Thr Leu Pro Arg Ser Gly Asn Leu Ile Val Val
        275                 280                 285

Glu Ser Val Leu Met Ala Val Ala Phe Leu Ala Met Leu Leu Val Leu
290                 295                 300

Gly Leu Cys Gly Ala Ala Tyr Arg Pro Thr Glu Ile Asp Leu Arg
305                 310                 315                 320

Ser Val Gly Trp Gly Asn Ile Phe Gln Leu Pro Phe Lys His Val Arg
                325                 330                 335

Asp Tyr Arg Leu Arg His Leu Val Pro Phe Ile Tyr Ser Gly Phe
            340                 345                 350

Glu Val Leu Phe Ala Cys Thr Gly Ile Ala Leu Gly Tyr Gly Val Cys
        355                 360                 365
```

```
Ser Val Gly Leu Glu Arg Leu Ala Tyr Leu Leu Val Ala Tyr Ser Leu
    370                 375                 380

Gly Ala Ser Ala Ala Ser Leu Leu Gly Leu Leu Gly Leu Trp Leu Pro
385                 390                 395                 400

Arg Pro Val Pro Leu Val Ala Gly Ala Gly Val His Leu Leu Leu Thr
                405                 410                 415

Phe Ile Leu Phe Phe Trp Ala Pro Val Pro Arg Val Leu Gln His Ser
                420                 425                 430

Trp Ile Leu Tyr Val Ala Ala Ala Leu Trp Gly Val Gly Ser Ala Leu
            435                 440                 445

Asn Lys Thr Gly Leu Ser Thr Leu Leu Gly Ile Leu Tyr Glu Asp Lys
            450                 455                 460

Glu Arg Gln Asp Phe Ile Phe Thr Ile Tyr His Trp Trp Gln Ala Val
465                 470                 475                 480

Ala Ile Phe Thr Val Tyr Leu Gly Ser Ser Leu His Met Lys Ala Lys
                485                 490                 495

Leu Ala Val Leu Leu Val Thr Leu Val Ala Ala Val Ser Tyr Leu
                500                 505                 510

Arg Ile Glu Gln Lys Leu Arg Arg Gly Val Ala Pro Arg Gln Pro Arg
            515                 520                 525

Ile Pro Arg Pro Gln His Lys Val Arg Gly Tyr Arg Tyr Leu Glu Glu
            530                 535                 540

Asp Asn Ser Asp Glu Ser Asp Ala Glu Gly Glu His Gly Asp Gly Ala
545                 550                 555                 560

Glu Glu Glu Ala Pro Pro Ala Gly Pro Arg Pro Gly Pro Glu Pro Ala
                565                 570                 575

Gly Leu Gly Arg Arg Pro Cys Pro Tyr Glu Gln Ala Gln Gly Gly Asp
                580                 585                 590

Gly Pro Glu Glu Gln
            595
```